United States Patent
Salmeron et al.

(10) Patent No.: US 6,528,702 B1
(45) Date of Patent: Mar. 4, 2003

(54) PLANT GENES AND USES THEREOF

(75) Inventors: John Manuel Salmeron, Hillsborough, NC (US); Laura Jean Weislo, Raleigh, NC (US); Michael G. Willits, Apex, NC (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 09/519,232

(22) Filed: Mar. 6, 2000

Related U.S. Application Data

(60) Provisional application No. 60/219,338, filed on Mar. 9, 1999.

(51) Int. Cl.[7] .................. A01H 1/00; A01H 11/00; C07H 21/02; C12N 5/04; C12N 15/82
(52) U.S. Cl. .................. 800/278; 536/23.1; 536/23.6; 536/24.3; 435/70.1; 435/320.1; 435/410; 435/419; 435/468; 800/295
(58) Field of Search ................ 536/23.1, 24.3, 536/23.6; 435/6, 320.1, 419, 468, 410, 70.1; 800/295, 278

(56) References Cited

FOREIGN PATENT DOCUMENTS

| WO | WO 98/06748 | 2/1998 |
|---|---|---|
| WO | WO 98/26082 | 6/1998 |
| WO | WO 98/29537 | 7/1998 |
| WO | WO 00/28036 | 5/2000 |

OTHER PUBLICATIONS

Database ENBL–ENEST–PLN4 [online] Entry/Acc. No. AW399343, Feb. 8, 2000, ALCALA J., et al., "EST309843 L. pennelii trichome, Cornell University Lycopersicon pennelii".
Cao, H. et al., "The Arabidopsis NPR1 Gene That controls Systemic Acquired Resistance Encodes a Novel protein Containing Ankyrin Repeats," Cell, 88: pp. 57–63 (1997).
Ryals, J. et al., "The Arabidopsis NIM1 Protein Shows Homology to the Mammalian Transcription Factor Inhibitor IκB," The Plant Cell, 9: pp. 425–439 (1997).
Newman, T. et al., Genbank Accession No. T22612 (1997).
Rounsley, S.D. et al., Genbank Accession No. B26306 (1997).

*Primary Examiner*—Sean McGarry
*Assistant Examiner*—Janet Epps
(74) *Attorney, Agent, or Firm*—Mary Kakefuda; Tim Meigs

(57) ABSTRACT

Homologues of the Arabidopsis NIM1 gene, which is involved in the signal transduction cascade leading to systemic acquired resistance (SAR), are isolated from *Nicotiana tabacum* (tobacco), *Lycopersicon esculentum* (tomato), *Brassica napus* (oilseed rape), *Arabidopsis thaliana*, *Beta vulgaris* (sugarbeet), *Helianthus annuus* (sunflower), and *Solanum tuberosum* (potato). The invention further concerns transformation vectors and processes for expressing the NIM1 homologues in transgenic plants to increase SAR gene expression and enhance broad spectrum disease resistance.

10 Claims, No Drawings

SEQUENCE LISTING

<160> NUMBER OF SEQ ID NOS: 74

<210> SEQ ID NO 1
<211> LENGTH: 1767
<212> TYPE: DNA
<213> ORGANISM: Nicotiana tabacum
<220> FEATURE:
<221> NAME/KEY: CDS
<222> LOCATION: (1)..(1764)
<223> OTHER INFORMATION: Full length tobacco cDNA sequence

<400> SEQUENCE: 1

| | | | | | | | | | | | | | | | | |
|---|---|---|---|---|---|---|---|---|---|---|---|---|---|---|---|---|
| atg | aat | agt | agg | act | gcg | ttt | tct | gat | tcg | aat | gac | atc | agc | gga | | 48 |
| Met | Asp | Asn | Ser | Arg | Thr | Ala | Phe | Ser | Asp | Ser | Asn | Asp | Ile | Ser | Gly | |
| 1 | | | | 5 | | | | | 10 | | | | | 15 | | |

| agc | agt | agt | ata | tgc | tgc | atc | ggc | ggc | ggc | atg | act | gaa | ttt | ttc | tcg | 96 |
|---|---|---|---|---|---|---|---|---|---|---|---|---|---|---|---|---|
| Ser | Ser | Ser | Ile | Cys | Cys | Ile | Gly | Gly | Gly | Met | Thr | Glu | Phe | Phe | Ser | |
| | | | 20 | | | | | 25 | | | | | 30 | | | |

| ccg | gag | act | tcg | ccg | gcg | gag | atc | act | tca | ctg | aaa | cgc | cta | tcg | gaa | 144 |
|---|---|---|---|---|---|---|---|---|---|---|---|---|---|---|---|---|
| Pro | Glu | Thr | Ser | Pro | Ala | Glu | Ile | Thr | Ser | Leu | Lys | Arg | Leu | Ser | Glu | |
| | 35 | | | | | 40 | | | | | 45 | | | | | |

| aca | ctg | gaa | tct | atc | ttc | gat | gcg | tct | ttg | ccg | gag | ttt | gac | tac | ttc | 192 |
|---|---|---|---|---|---|---|---|---|---|---|---|---|---|---|---|---|
| Thr | Leu | Glu | Ser | Ile | Phe | Asp | Ala | Ser | Leu | Pro | Glu | Phe | Asp | Tyr | Phe | |
| 50 | | | | | 55 | | | | | 60 | | | | | | |

| gcc | gac | gct | aag | ctt | gtg | gtt | tcc | ggc | ccg | tgt | aag | gaa | att | ccg | gtg | 240 |
|---|---|---|---|---|---|---|---|---|---|---|---|---|---|---|---|---|
| Ala | Asp | Ala | Lys | Leu | Val | Val | Ser | Gly | Pro | Cys | Lys | Glu | Ile | Pro | Val | |
| 65 | | | | 70 | | | | | 75 | | | | | 80 | | |

| cac | cgg | tgc | att | ttg | tcg | gcg | agg | agt | ccg | ttc | ttt | aag | aat | ttg | ttc | 288 |
|---|---|---|---|---|---|---|---|---|---|---|---|---|---|---|---|---|
| His | Arg | Cys | Ile | Leu | Ser | Ala | Arg | Ser | Pro | Phe | Phe | Lys | Asn | Leu | Phe | |
| | | | | 85 | | | | | 90 | | | | | 95 | | |

| tgc | ggt | aaa | aag | gag | aag | aat | agt | agt | aag | gtg | gaa | ttg | aag | gag | gtg | 336 |
|---|---|---|---|---|---|---|---|---|---|---|---|---|---|---|---|---|
| Cys | Gly | Lys | Lys | Glu | Lys | Asn | Ser | Ser | Lys | Val | Glu | Leu | Lys | Glu | Val | |
| | | | 100 | | | | | 105 | | | | | 110 | | | |

| atg | aaa | gag | cat | gag | gtg | agc | tat | gat | gct | gta | atg | agt | gta | ttg | gct | 384 |
|---|---|---|---|---|---|---|---|---|---|---|---|---|---|---|---|---|
| Met | Lys | Glu | His | Glu | Val | Ser | Tyr | Asp | Ala | Val | Met | Ser | Val | Leu | Ala | |
| | | 115 | | | | | 120 | | | | | 125 | | | | |

| tat | ttg | tat | agt | ggt | aaa | gtt | agg | cct | tca | cct | aaa | gat | gtg | tgt | gtt | 432 |
|---|---|---|---|---|---|---|---|---|---|---|---|---|---|---|---|---|
| Tyr | Leu | Tyr | Ser | Gly | Lys | Val | Arg | Pro | Ser | Pro | Lys | Asp | Val | Cys | Val | |
| | 130 | | | | | 135 | | | | | 140 | | | | | |

| tgt | gtg | gac | aat | gac | tgc | tct | cat | gtg | gct | tgt | agg | cca | gct | gtg | gca | 480 |
|---|---|---|---|---|---|---|---|---|---|---|---|---|---|---|---|---|
| Cys | Val | Asp | Asn | Asp | Cys | Ser | His | Val | Ala | Cys | Arg | Pro | Ala | Val | Ala | |
| 145 | | | | | 150 | | | | | 155 | | | | | 160 | |

| ttc | ctg | gtt | gag | gtt | ttg | tac | aca | tca | ttt | acc | ttt | cag | atc | tct | gaa | 528 |
|---|---|---|---|---|---|---|---|---|---|---|---|---|---|---|---|---|
| Phe | Leu | Val | Glu | Val | Leu | Tyr | Thr | Ser | Phe | Thr | Phe | Gln | Ile | Ser | Glu | |
| | | | | 165 | | | | | 170 | | | | | 175 | | |

| ttg | gtt | gac | aag | ttt | cag | aga | cac | cta | ctg | gat | att | ctt | gac | aaa | act | 576 |
|---|---|---|---|---|---|---|---|---|---|---|---|---|---|---|---|---|
| Leu | Val | Asp | Lys | Phe | Gln | Arg | His | Leu | Leu | Asp | Ile | Leu | Asp | Lys | Thr | |
| | | | 180 | | | | | 185 | | | | | 190 | | | |

| gca | gca | gac | gat | gta | atg | atg | gtt | tta | tct | gtt | gca | aac | att | tgt | ggt | 624 |
|---|---|---|---|---|---|---|---|---|---|---|---|---|---|---|---|---|
| Ala | Ala | Asp | Asp | Val | Met | Met | Val | Leu | Ser | Val | Ala | Asn | Ile | Cys | Gly | |
| | | 195 | | | | | 200 | | | | | 205 | | | | |

| aaa | gca | tgc | gag | aga | ttg | ctt | tca | agc | tgc | att | gag | att | att | gtc | aag | 672 |
|---|---|---|---|---|---|---|---|---|---|---|---|---|---|---|---|---|
| Lys | Ala | Cys | Glu | Arg | Leu | Leu | Ser | Ser | Cys | Ile | Glu | Ile | Ile | Val | Lys | |
| | 210 | | | | | 215 | | | | | 220 | | | | | |

| tct | aat | gtt | gat | atc | ata | acc | ctt | gat | aaa | gcc | ttg | cct | cat | gac | att | 720 |
|---|---|---|---|---|---|---|---|---|---|---|---|---|---|---|---|---|
| Ser | Asn | Val | Asp | Ile | Ile | Thr | Leu | Asp | Lys | Ala | Leu | Pro | His | Asp | Ile | |
| 225 | | | | | 230 | | | | | 235 | | | | | 240 | |

| gta | aaa | caa | att | act | gat | tca | cga | gcg | gaa | ctt | ggt | cta | caa | ggg | cct | 768 |
|---|---|---|---|---|---|---|---|---|---|---|---|---|---|---|---|---|
| Val | Lys | Gln | Ile | Thr | Asp | Ser | Arg | Ala | Glu | Leu | Gly | Leu | Gln | Gly | Pro | |
| | | | | 245 | | | | | 250 | | | | | 255 | | |

```
gaa agc aac ggt ttt cct gat aaa cat gtt aag agg ata cat agg gca    816
Glu Ser Asn Gly Phe Pro Asp Lys His Val Lys Arg Ile His Arg Ala
            260                 265                 270 ttg gat tct gat gat gtt gaa tta cta caa atg ttg cta aga gag ggg    864
Leu Asp Ser Asp Asp Val Glu Leu Leu Gln Met Leu Leu Arg Glu Gly
            275                 280                 285 cat act acc cta gat gat gca tat gct ctc cat tat gct gta gcg tat    912
His Thr Thr Leu Asp Asp Ala Tyr Ala Leu His Tyr Ala Val Ala Tyr
            290                 295                 300 tgc gat gca aag act aca gca gaa ctt cta gat ctt gca ctt gct gat    960
Cys Asp Ala Lys Thr Thr Ala Glu Leu Leu Asp Leu Ala Leu Ala Asp
305                 310                 315                 320 att aat cat caa aat tca agg gga tac acg gtg ctg cat gtt gca gcc   1008
Ile Asn His Gln Asn Ser Arg Gly Tyr Thr Val Leu His Val Ala Ala
            325                 330                 335 atg agg aaa gag cct aaa att gta gtg tcc ctt tta acc aaa gga gct   1056
Met Arg Lys Glu Pro Lys Ile Val Val Ser Leu Leu Thr Lys Gly Ala
            340                 345                 350 aga cct tct gat ctg aca tcc gat gga aga aaa gca ctt caa atc gcc   1104
Arg Pro Ser Asp Leu Thr Ser Asp Gly Arg Lys Ala Leu Gln Ile Ala
            355                 360                 365 aag agg ctc act agg ctt gtg gat ttc agt aag tct ccg gag gaa gga   1152
Lys Arg Leu Thr Arg Leu Val Asp Phe Ser Lys Ser Pro Glu Glu Gly
            370                 375                 380 aaa tct gct tcg aat gat cgg tta tgc att gag att ctg gag caa gca   1200
Lys Ser Ala Ser Asn Asp Arg Leu Cys Ile Glu Ile Leu Glu Gln Ala
385                 390                 395                 400 gaa aga aga gac cct ctg cta gga gaa gct tct gta tct ctt gct atg   1248
Glu Arg Arg Asp Pro Leu Leu Gly Glu Ala Ser Val Ser Leu Ala Met
                405                 410                 415 gca ggc gat gat ttg cgt atg aag ctg tta tac ctt gaa aat aga gtt   1296
Ala Gly Asp Asp Leu Arg Met Lys Leu Leu Tyr Leu Glu Asn Arg Val
                420                 425                 430 ggc ctg gct aaa ctc ctt ttt cca atg gaa gct aaa gtt gca atg gac   1344
Gly Leu Ala Lys Leu Leu Phe Pro Met Glu Ala Lys Val Ala Met Asp
            435                 440                 445 att gct caa gtt gat ggc act tct gag ttc cca ctg gct agc atc ggc   1392
Ile Ala Gln Val Asp Gly Thr Ser Glu Phe Pro Leu Ala Ser Ile Gly
450                 455                 460 aaa aag atg gct aat gca cag agg aca aca gta gat ttg aac gag gct   1440
Lys Lys Met Ala Asn Ala Gln Arg Thr Thr Val Asp Leu Asn Glu Ala
465                 470                 475                 480 cct ttc aag ata aaa gag gag cac ttg aat cgg ctt aga gca ctc tct   1488
Pro Phe Lys Ile Lys Glu Glu His Leu Asn Arg Leu Arg Ala Leu Ser
                485                 490                 495 aga act gta gaa ctt gga aaa cgc ttc ttt cca cgt tgt tca gaa gtt   1536
Arg Thr Val Glu Leu Gly Lys Arg Phe Phe Pro Arg Cys Ser Glu Val
            500                 505                 510 cta aat aag atc atg gat gct gat gac ttg tct gag ata gct tac atg   1584
Leu Asn Lys Ile Met Asp Ala Asp Asp Leu Ser Glu Ile Ala Tyr Met
            515                 520                 525 ggg aat gat acg gca gaa gag cgt caa ctg aag aag caa agg tac atg   1632
Gly Asn Asp Thr Ala Glu Glu Arg Gln Leu Lys Lys Gln Arg Tyr Met
530                 535                 540 gaa ctt caa gaa att ctg act aaa gca ttc act gag gat aaa gaa gaa   1680
Glu Leu Gln Glu Ile Leu Thr Lys Ala Phe Thr Glu Asp Lys Glu Glu
545                 550                 555                 560 tat gat aag act aac aac atc tcc tca tct tgt tcc tct aca tct aag   1728
Tyr Asp Lys Thr Asn Asn Ile Ser Ser Ser Cys Ser Ser Thr Ser Lys
```

```
                        565                 570                 575
gga gta gat aag ccc aat aag ctc cct ttt agg aaa tag                              1767
Gly Val Asp Lys Pro Asn Lys Leu Pro Phe Arg Lys
            580                 585
```

<210> SEQ ID NO 2
<211> LENGTH: 588
<212> TYPE: PRT
<213> ORGANISM: Nicotiana tabacum

<400> SEQUENCE: 2

```
Met Asp Asn Ser Arg Thr Ala Phe Ser Asp Ser Asn Asp Ile Ser Gly
 1               5                  10                  15

Ser Ser Ser Ile Cys Cys Ile Gly Gly Gly Met Thr Glu Phe Phe Ser
             20                  25                  30

Pro Glu Thr Ser Pro Ala Glu Ile Thr Ser Leu Lys Arg Leu Ser Glu
         35                  40                  45

Thr Leu Glu Ser Ile Phe Asp Ala Ser Leu Pro Glu Phe Asp Tyr Phe
     50                  55                  60

Ala Asp Ala Lys Leu Val Val Ser Gly Pro Cys Lys Glu Ile Pro Val
 65                  70                  75                  80

His Arg Cys Ile Leu Ser Ala Arg Ser Pro Phe Phe Lys Asn Leu Phe
                 85                  90                  95

Cys Gly Lys Lys Glu Lys Asn Ser Ser Lys Val Glu Leu Lys Glu Val
            100                 105                 110

Met Lys Glu His Glu Val Ser Tyr Asp Ala Val Met Ser Val Leu Ala
        115                 120                 125

Tyr Leu Tyr Ser Gly Lys Val Arg Pro Ser Pro Lys Asp Val Cys Val
    130                 135                 140

Cys Val Asp Asn Asp Cys Ser His Val Ala Cys Arg Pro Ala Val Ala
145                 150                 155                 160

Phe Leu Val Glu Val Leu Tyr Thr Ser Phe Thr Phe Gln Ile Ser Glu
                165                 170                 175

Leu Val Asp Lys Phe Gln Arg His Leu Leu Asp Ile Leu Asp Lys Thr
            180                 185                 190

Ala Ala Asp Asp Val Met Met Val Leu Ser Val Ala Asn Ile Cys Gly
        195                 200                 205

Lys Ala Cys Glu Arg Leu Leu Ser Ser Cys Ile Glu Ile Val Lys
    210                 215                 220

Ser Asn Val Asp Ile Ile Thr Leu Asp Lys Ala Leu Pro His Asp Ile
225                 230                 235                 240

Val Lys Gln Ile Thr Asp Ser Arg Ala Glu Leu Gly Leu Gln Gly Pro
                245                 250                 255

Glu Ser Asn Gly Phe Pro Asp Lys His Val Lys Arg Ile His Arg Ala
            260                 265                 270

Leu Asp Ser Asp Asp Val Glu Leu Leu Gln Met Leu Leu Arg Glu Gly
        275                 280                 285

His Thr Thr Leu Asp Asp Ala Tyr Ala Leu His Tyr Ala Val Ala Tyr
    290                 295                 300

Cys Asp Ala Lys Thr Thr Ala Glu Leu Leu Asp Leu Ala Leu Ala Asp
305                 310                 315                 320

Ile Asn His Gln Asn Ser Arg Gly Tyr Thr Val Leu His Val Ala Ala
                325                 330                 335

Met Arg Lys Glu Pro Lys Ile Val Val Ser Leu Leu Thr Lys Gly Ala
            340                 345                 350
```

```
Arg Pro Ser Asp Leu Thr Ser Asp Gly Arg Lys Ala Leu Gln Ile Ala
        355                 360                 365

Lys Arg Leu Thr Arg Leu Val Asp Phe Ser Lys Ser Pro Glu Glu Gly
    370                 375                 380

Lys Ser Ala Ser Asn Asp Arg Leu Cys Ile Glu Ile Leu Glu Gln Ala
385                 390                 395                 400

Glu Arg Arg Asp Pro Leu Leu Gly Glu Ala Ser Val Ser Leu Ala Met
                405                 410                 415

Ala Gly Asp Asp Leu Arg Met Lys Leu Leu Tyr Leu Glu Asn Arg Val
            420                 425                 430

Gly Leu Ala Lys Leu Leu Phe Pro Met Glu Ala Lys Val Ala Met Asp
        435                 440                 445

Ile Ala Gln Val Asp Gly Thr Ser Glu Phe Pro Leu Ala Ser Ile Gly
    450                 455                 460

Lys Lys Met Ala Asn Ala Gln Arg Thr Thr Val Asp Leu Asn Glu Ala
465                 470                 475                 480

Pro Phe Lys Ile Lys Glu Glu His Leu Asn Arg Leu Arg Ala Leu Ser
                485                 490                 495

Arg Thr Val Glu Leu Gly Lys Arg Phe Phe Pro Arg Cys Ser Glu Val
            500                 505                 510

Leu Asn Lys Ile Met Asp Ala Asp Asp Leu Ser Glu Ile Ala Tyr Met
        515                 520                 525

Gly Asn Asp Thr Ala Glu Glu Arg Gln Leu Lys Lys Gln Arg Tyr Met
    530                 535                 540

Glu Leu Gln Glu Ile Leu Thr Lys Ala Phe Thr Glu Asp Lys Glu Glu
545                 550                 555                 560

Tyr Asp Lys Thr Asn Asn Ile Ser Ser Ser Cys Ser Ser Thr Ser Lys
                565                 570                 575

Gly Val Asp Lys Pro Asn Lys Leu Pro Phe Arg Lys
            580                 585

<210> SEQ ID NO 3
<211> LENGTH: 1731
<212> TYPE: DNA
<213> ORGANISM: Lycopersicon esculentum
<220> FEATURE:
<221> NAME/KEY: CDS
<222> LOCATION: (1)..(1728)
<223> OTHER INFORMATION: Full length tomato cDNA sequence

<400> SEQUENCE: 3 atg gat agt aga act gct ttt tcg gat tcc aat gat att agt gga agc        48
Met Asp Ser Arg Thr Ala Phe Ser Asp Ser Asn Asp Ile Ser Gly Ser
  1               5                  10                  15 agt agt ata tgc tgc atg aac gaa tcg gaa act tca ctg gca gac gtc        96
Ser Ser Ile Cys Cys Met Asn Glu Ser Glu Thr Ser Leu Ala Asp Val
             20                  25                  30 aat tcc ctc aaa cgt cta tca gaa aca cta gag tct atc ttc gat gcg       144
Asn Ser Leu Lys Arg Leu Ser Glu Thr Leu Glu Ser Ile Phe Asp Ala
         35                  40                  45 tct gcg ccg gat ttc gac ttc ttc gct gat gct aag ctt ctg gct cca       192
Ser Ala Pro Asp Phe Asp Phe Phe Ala Asp Ala Lys Leu Leu Ala Pro
     50                  55                  60 ggc ggt aag gaa att ccg gtg cat cgg tgc att ttg tcg gcg agg agt       240
Gly Gly Lys Glu Ile Pro Val His Arg Cys Ile Leu Ser Ala Arg Ser
 65                  70                  75                  80 cct ttt ttt aag aat gta ttc tgt ggg aaa gat agc agc acg aag ctg       288
```

```
            Pro Phe Phe Lys Asn Val Phe Cys Gly Lys Asp Ser Ser Thr Lys Leu
                             85                  90                  95 gaa ctc aaa gag ctg atg aaa gag tat gag gtg agt ttt gat gcc gtg             336
Glu Leu Lys Glu Leu Met Lys Glu Tyr Glu Val Ser Phe Asp Ala Val
            100                 105                 110 gtc agt gtg ctc gcc tat ttg tat agt gga aaa gtt agg cct gca tct             384
Val Ser Val Leu Ala Tyr Leu Tyr Ser Gly Lys Val Arg Pro Ala Ser
            115                 120                 125 aaa gat gtg tgt gtt tgt gtg gac aat gag tgc ttg cat gta gct tgt             432
Lys Asp Val Cys Val Cys Val Asp Asn Glu Cys Leu His Val Ala Cys
        130                 135                 140 agg cca gct gtg gcc ttc atg gtt cag gtt ttg tac gca tcc ttt acc             480
Arg Pro Ala Val Ala Phe Met Val Gln Val Leu Tyr Ala Ser Phe Thr
145                 150                 155                 160 ttt cag atc tct caa ttg gtc gac aag ttt cag aga cac cta ttg gat             528
Phe Gln Ile Ser Gln Leu Val Asp Lys Phe Gln Arg His Leu Leu Asp
                165                 170                 175 att ctt gac aaa gct gta gca gat gat gta atg atg gtt tta tcc gtt             576
Ile Leu Asp Lys Ala Val Ala Asp Asp Val Met Met Val Leu Ser Val
            180                 185                 190 gca aac att tgc ggt aaa gca tgt gaa aga tta ctt tca aga tgc att             624
Ala Asn Ile Cys Gly Lys Ala Cys Glu Arg Leu Leu Ser Arg Cys Ile
            195                 200                 205 gat att att gtc aag tct aat gtt gat atc ata acc ctt gat aag tcc             672
Asp Ile Ile Val Lys Ser Asn Val Asp Ile Ile Thr Leu Asp Lys Ser
210                 215                 220 ttg cct cat gac att gta aaa caa atc act gat tca cgt gct gaa ctt             720
Leu Pro His Asp Ile Val Lys Gln Ile Thr Asp Ser Arg Ala Glu Leu
225                 230                 235                 240 ggt ctg caa ggg cct gaa agc aat ggt ttt cct gat aaa cat gtt aag             768
Gly Leu Gln Gly Pro Glu Ser Asn Gly Phe Pro Asp Lys His Val Lys
                245                 250                 255 agg ata cat aga gca ttg gac tct gat gat gtt gaa tta cta agg atg             816
Arg Ile His Arg Ala Leu Asp Ser Asp Asp Val Glu Leu Leu Arg Met
            260                 265                 270 ttg ctt aaa gag ggg cat act act ctt gat gat gca tat gct ctc cac             864
Leu Leu Lys Glu Gly His Thr Thr Leu Asp Asp Ala Tyr Ala Leu His
            275                 280                 285 tat gct gta gca tat tgc gat gca aag act aca gca gaa ctt tta gat             912
Tyr Ala Val Ala Tyr Cys Asp Ala Lys Thr Thr Ala Glu Leu Leu Asp
        290                 295                 300 ctt tca ctt gct gat gtt aat cat caa aat cct aga gga cac acg gta             960
Leu Ser Leu Ala Asp Val Asn His Gln Asn Pro Arg Gly His Thr Val
305                 310                 315                 320 ctt cat gtt gct gcc atg agg aaa gaa cct aaa att ata gtg tcc ctt            1008
Leu His Val Ala Ala Met Arg Lys Glu Pro Lys Ile Ile Val Ser Leu
                325                 330                 335 tta acc aaa gga gct aga cct tct gat ctg aca tcc gat ggc aaa aaa            1056
Leu Thr Lys Gly Ala Arg Pro Ser Asp Leu Thr Ser Asp Gly Lys Lys
            340                 345                 350 gca ctt caa att gct aag agg ctc act agg ctt gta gat ttt acc aag            1104
Ala Leu Gln Ile Ala Lys Arg Leu Thr Arg Leu Val Asp Phe Thr Lys
            355                 360                 365 tct aca gag gaa gga aaa tct gct cca aag gat cgg tta tgc att gag            1152
Ser Thr Glu Glu Gly Lys Ser Ala Pro Lys Asp Arg Leu Cys Ile Glu
        370                 375                 380 att ctg gag caa gca gaa aga aga gat cca cta cta gga gaa gct tca            1200
Ile Leu Glu Gln Ala Glu Arg Arg Asp Pro Leu Leu Gly Glu Ala Ser
385                 390                 395                 400
```

```
tta tct ctt gct atg gca ggc gat gat ttg cgt atg aag ctg tta tac       1248
Leu Ser Leu Ala Met Ala Gly Asp Asp Leu Arg Met Lys Leu Leu Tyr
            405                 410                 415 ctt gaa aat aga gtt ggt ctg gct aaa ctc ctt ttt ccc atg gaa gca       1296
Leu Glu Asn Arg Val Gly Leu Ala Lys Leu Leu Phe Pro Met Glu Ala
            420                 425                 430 aaa gtt gca atg gac att gca caa gtt gat ggc acg tct gaa tta ccc       1344
Lys Val Ala Met Asp Ile Ala Gln Val Asp Gly Thr Ser Glu Leu Pro
            435                 440                 445 ctg gct agc atg agg aag aag ata gct gat gca cag agg aca aca gtg       1392
Leu Ala Ser Met Arg Lys Lys Ile Ala Asp Ala Gln Arg Thr Thr Val
            450                 455                 460 gat ttg aac gag gct cct ttc aag atg aaa gag gag cac ttg aat cgg       1440
Asp Leu Asn Glu Ala Pro Phe Lys Met Lys Glu Glu His Leu Asn Arg
465                 470                 475                 480 ctt agg gct ctc tct aga act gtg gaa ctt gga aaa cgg ttc ttt cca       1488
Leu Arg Ala Leu Ser Arg Thr Val Glu Leu Gly Lys Arg Phe Phe Pro
            485                 490                 495 cgt tgt tca gaa gtt cta aat aag atc atg gat gct gat gac ttg tct       1536
Arg Cys Ser Glu Val Leu Asn Lys Ile Met Asp Ala Asp Asp Leu Ser
            500                 505                 510 gag ata gct tac atg ggg aat gat aca gta gaa gag cgt caa ctg aag       1584
Glu Ile Ala Tyr Met Gly Asn Asp Thr Val Glu Glu Arg Gln Leu Lys
            515                 520                 525 aag caa agg tac atg gaa ctt caa gaa att ttg tct aaa gca ttc acg       1632
Lys Gln Arg Tyr Met Glu Leu Gln Glu Ile Leu Ser Lys Ala Phe Thr
            530                 535                 540 gag gat aaa gaa gaa ttt gct aag act aac atg tcc tca tct tgt tcc       1680
Glu Asp Lys Glu Glu Phe Ala Lys Thr Asn Met Ser Ser Ser Cys Ser
545                 550                 555                 560 tct aca tct aag gga gta gat aag ccc aat aat ctc cca ttt agg aaa       1728
Ser Thr Ser Lys Gly Val Asp Lys Pro Asn Asn Leu Pro Phe Arg Lys
            565                 570                 575 tag                                                                   1731
```

<210> SEQ ID NO 4
<211> LENGTH: 576
<212> TYPE: PRT
<213> ORGANISM: Lycopersicon esculentum

<400> SEQUENCE: 4

```
Met Asp Ser Arg Thr Ala Phe Ser Asp Ser Asn Asp Ile Ser Gly Ser
 1               5                  10                  15

Ser Ser Ile Cys Cys Met Asn Glu Ser Glu Thr Ser Leu Ala Asp Val
                20                  25                  30

Asn Ser Leu Lys Arg Leu Ser Glu Thr Leu Glu Ser Ile Phe Asp Ala
            35                  40                  45

Ser Ala Pro Asp Phe Asp Phe Ala Asp Ala Lys Leu Leu Ala Pro
        50                  55                  60

Gly Gly Lys Glu Ile Pro Val His Arg Cys Ile Leu Ser Ala Arg Ser
 65                  70                  75                  80

Pro Phe Phe Lys Asn Val Phe Cys Gly Lys Asp Ser Ser Thr Lys Leu
                85                  90                  95

Glu Leu Lys Glu Leu Met Lys Glu Tyr Glu Val Ser Phe Asp Ala Val
            100                 105                 110

Val Ser Val Leu Ala Tyr Leu Tyr Ser Gly Lys Val Arg Pro Ala Ser
        115                 120                 125

Lys Asp Val Cys Val Cys Val Asp Asn Glu Cys Leu His Val Ala Cys
```

```
        130                 135                 140
Arg Pro Ala Val Ala Phe Met Val Gln Val Leu Tyr Ala Ser Phe Thr
145                 150                 155                 160
Phe Gln Ile Ser Gln Leu Val Asp Lys Phe Gln Arg His Leu Leu Asp
                165                 170                 175
Ile Leu Asp Lys Ala Val Ala Asp Val Met Met Val Leu Ser Val
            180                 185                 190
Ala Asn Ile Cys Gly Lys Ala Cys Glu Arg Leu Leu Ser Arg Cys Ile
            195                 200                 205
Asp Ile Ile Val Lys Ser Asn Val Asp Ile Ile Thr Leu Asp Lys Ser
            210                 215                 220
Leu Pro His Asp Ile Val Lys Gln Ile Thr Asp Ser Arg Ala Glu Leu
225                 230                 235                 240
Gly Leu Gln Gly Pro Glu Ser Asn Gly Phe Pro Asp Lys His Val Lys
                245                 250                 255
Arg Ile His Arg Ala Leu Asp Ser Asp Val Glu Leu Leu Arg Met
                260                 265                 270
Leu Leu Lys Glu Gly His Thr Thr Leu Asp Asp Ala Tyr Ala Leu His
            275                 280                 285
Tyr Ala Val Ala Tyr Cys Asp Ala Lys Thr Thr Ala Glu Leu Leu Asp
290                 295                 300
Leu Ser Leu Ala Asp Val Asn His Gln Asn Pro Arg Gly His Thr Val
305                 310                 315                 320
Leu His Val Ala Ala Met Arg Lys Glu Pro Lys Ile Val Ser Leu
                325                 330                 335
Leu Thr Lys Gly Ala Arg Pro Ser Asp Leu Thr Ser Asp Gly Lys Lys
            340                 345                 350
Ala Leu Gln Ile Ala Lys Arg Leu Thr Arg Leu Val Asp Phe Thr Lys
            355                 360                 365
Ser Thr Glu Glu Gly Lys Ser Ala Pro Lys Asp Arg Leu Cys Ile Glu
370                 375                 380
Ile Leu Glu Gln Ala Glu Arg Arg Asp Pro Leu Leu Gly Glu Ala Ser
385                 390                 395                 400
Leu Ser Leu Ala Met Ala Gly Asp Asp Leu Arg Met Lys Leu Leu Tyr
                405                 410                 415
Leu Glu Asn Arg Val Gly Leu Ala Lys Leu Leu Phe Pro Met Glu Ala
            420                 425                 430
Lys Val Ala Met Asp Ile Ala Gln Val Asp Gly Thr Ser Glu Leu Pro
            435                 440                 445
Leu Ala Ser Met Arg Lys Lys Ile Ala Asp Ala Gln Arg Thr Thr Val
450                 455                 460
Asp Leu Asn Glu Ala Pro Phe Lys Met Lys Glu Glu His Leu Asn Arg
465                 470                 475                 480
Leu Arg Ala Leu Ser Arg Thr Val Glu Leu Gly Lys Arg Phe Phe Pro
                485                 490                 495
Arg Cys Ser Glu Val Leu Asn Lys Ile Met Asp Ala Asp Leu Ser
                500                 505                 510
Glu Ile Ala Tyr Met Gly Asn Asp Thr Val Glu Glu Arg Gln Leu Lys
            515                 520                 525
Lys Gln Arg Tyr Met Glu Leu Gln Glu Ile Leu Ser Lys Ala Phe Thr
            530                 535                 540
Glu Asp Lys Glu Glu Phe Ala Lys Thr Asn Met Ser Ser Ser Cys Ser
545                 550                 555                 560
```

```
Ser Thr Ser Lys Gly Val Asp Lys Pro Asn Asn Leu Pro Phe Arg Lys
            565                 570                 575

<210> SEQ ID NO 5
<211> LENGTH: 1740
<212> TYPE: DNA
<213> ORGANISM: Brassica napus
<220> FEATURE:
<221> NAME/KEY: CDS
<222> LOCATION: (1)..(1737)
<223> OTHER INFORMATION: Canola cDNA sequence

<400> SEQUENCE: 5 atg gag acc att gct rga ttt gat gat ttc tat gag atc agc agc act      48
Met Glu Thr Ile Ala Xaa Phe Asp Asp Phe Tyr Glu Ile Ser Ser Thr
  1               5                  10                  15 agc ttc cyc gcc gca ccg gcg cca acc gat aac tcc gga tca tcc acc      96
Ser Phe Xaa Ala Ala Pro Ala Pro Thr Asp Asn Ser Gly Ser Ser Thr
             20                  25                  30 gtc twc ccg acg gag ctt ytc acc aga ccc gag gta tcc gcg ttt caa     144
Val Xaa Pro Thr Glu Leu Xaa Thr Arg Pro Glu Val Ser Ala Phe Gln
         35                  40                  45 ctc ctc tcc aac agc ctc gag tcc gtc ttc gac tcg ccg gaa gcg ttc     192
Leu Leu Ser Asn Ser Leu Glu Ser Val Phe Asp Ser Pro Glu Ala Phe
     50                  55                  60 tac agc gac gcc aag ctt gtt ctc tcc gac gac aag gaa gta tcc ttc     240
Tyr Ser Asp Ala Lys Leu Val Leu Ser Asp Asp Lys Glu Val Ser Phe
 65                  70                  75                  80 cac cgt tgc att ctc tcg gcg aga agc ctc ttc ttc aag gcc gct ttg     288
His Arg Cys Ile Leu Ser Ala Arg Ser Leu Phe Phe Lys Ala Ala Leu
                 85                  90                  95 rca gcc gcc gag aag gtg cag aag tcc acc ccc gtg aag ctc gag ctg     336
Xaa Ala Ala Glu Lys Val Gln Lys Ser Thr Pro Val Lys Leu Glu Leu
            100                 105                 110 aag aca ctc gcg gcg gaa tac gac gtc ggg ttc gat tct gtg gtg gct     384
Lys Thr Leu Ala Ala Glu Tyr Asp Val Gly Phe Asp Ser Val Val Ala
        115                 120                 125 gtt ctg gcg tac gtt tac agc ggc aga gtg agg ccg cct ccg aag gga     432
Val Leu Ala Tyr Val Tyr Ser Gly Arg Val Arg Pro Pro Pro Lys Gly
    130                 135                 140 gtt tct gaa tgc gca gac gak agc tgc tgc cac gtg gcg tgc cgt ccg     480
Val Ser Glu Cys Ala Asp Xaa Ser Cys Cys His Val Ala Cys Arg Pro
145                 150                 155                 160 gct gtg gat ttc atg gtg gag gtt ctc tac ttg gct ttc gtc ttc cag     528
Ala Val Asp Phe Met Val Glu Val Leu Tyr Leu Ala Phe Val Phe Gln
                165                 170                 175 att cag gaa ctg gtt acc atg tat cag agg cat tta ctg gat gtt gta     576
Ile Gln Glu Leu Val Thr Met Tyr Gln Arg His Leu Leu Asp Val Val
            180                 185                 190 gac aaa gtt awc ata gaa gac act ttg gtc gtc ctc aag ctt gct aac     624
Asp Lys Val Xaa Ile Glu Asp Thr Leu Val Val Leu Lys Leu Ala Asn
        195                 200                 205 atc tgc ggt aaa gcg tgc aag aag cta ttc gat aag tgc aga gag atc     672
Ile Cys Gly Lys Ala Cys Lys Lys Leu Phe Asp Lys Cys Arg Glu Ile
    210                 215                 220 att gtc aag tct aac gtg gat gtt gtt act cta aag aag tca ttg cct     720
Ile Val Lys Ser Asn Val Asp Val Val Thr Leu Lys Lys Ser Leu Pro
225                 230                 235                 240 gag rac att gcc aag caa gta atc gat atc cgc aaa gag ctc ggc ttg     768
Glu Xaa Ile Ala Lys Gln Val Ile Asp Ile Arg Lys Glu Leu Gly Leu
                245                 250                 255
```

```
gag gta gct gaa cca gag aaa cat gtc tcc aac ata cac aag gcg ctt      816
Glu Val Ala Glu Pro Glu Lys His Val Ser Asn Ile His Lys Ala Leu
            260                 265                 270 gag tca gac gat ctt gac ctt gtc gtt atg ctt ttg aaa gag ggc cac      864
Glu Ser Asp Asp Leu Asp Leu Val Val Met Leu Leu Lys Glu Gly His
        275                 280                 285 acg aat cta gac gaa gcg tat gct ctc cat ttt gct gtt gcg tat tgc      912
Thr Asn Leu Asp Glu Ala Tyr Ala Leu His Phe Ala Val Ala Tyr Cys
        290                 295                 300 gat gag aag aca gcg agg aat ctc ctg gaa ctg ggg ttt gcg gat gtc      960
Asp Glu Lys Thr Ala Arg Asn Leu Leu Glu Leu Gly Phe Ala Asp Val
305                 310                 315                 320 aac cgg aga aac ccg aga ggg tac acg gta att cac gtc gct gcg atg     1008
Asn Arg Arg Asn Pro Arg Gly Tyr Thr Val Ile His Val Ala Ala Met
                325                 330                 335 agg aaa gag ccg aca ctg ata gca ttg ttg ttg acg aaa ggg gct aat     1056
Arg Lys Glu Pro Thr Leu Ile Ala Leu Leu Leu Thr Lys Gly Ala Asn
            340                 345                 350 gca tta gaa atg tct ttg gac ggg aga act gct ctg ttg atc gcg aaa     1104
Ala Leu Glu Met Ser Leu Asp Gly Arg Thr Ala Leu Leu Ile Ala Lys
        355                 360                 365 caa gtc act aag gcg gcc gag tgt tgt att ctg gag aaa ggg aag tta     1152
Gln Val Thr Lys Ala Ala Glu Cys Cys Ile Leu Glu Lys Gly Lys Leu
        370                 375                 380 gct gcc aaa ggc gga gta tgt gta gag ata ctc aag caa cca gac aac     1200
Ala Ala Lys Gly Gly Val Cys Val Glu Ile Leu Lys Gln Pro Asp Asn
385                 390                 395                 400 aca cga gaa cca ttt cct gaa gat gtt tct ccc tcc ctt gca gtg gct     1248
Thr Arg Glu Pro Phe Pro Glu Asp Val Ser Pro Ser Leu Ala Val Ala
                405                 410                 415 gct gat caa ttc aag ata agg ttg att gat ctt gaa aac aga gtt caa     1296
Ala Asp Gln Phe Lys Ile Arg Leu Ile Asp Leu Glu Asn Arg Val Gln
            420                 425                 430 atg gct cga tgt ctc tat cca atg gaa gca caa gtt gca atg gat ttc     1344
Met Ala Arg Cys Leu Tyr Pro Met Glu Ala Gln Val Ala Met Asp Phe
        435                 440                 445 gcc cga atg aag gga aca cgc gag ttt gtc gtg acg aca gca act gac     1392
Ala Arg Met Lys Gly Thr Arg Glu Phe Val Val Thr Thr Ala Thr Asp
450                 455                 460 cta cac atg gaa cct ttc aag ttc gta gaa atg cat cag agt aga cta     1440
Leu His Met Glu Pro Phe Lys Phe Val Glu Met His Gln Ser Arg Leu
465                 470                 475                 480 aca gcg ctt tct aaa act gtg gaa ttc ggg aaa cgc ttc ttc cca cgc     1488
Thr Ala Leu Ser Lys Thr Val Glu Phe Gly Lys Arg Phe Phe Pro Arg
                485                 490                 495 tgt tcg aaa gtg ctc gat gat att gtg gac tct gag gac ttg act ata     1536
Cys Ser Lys Val Leu Asp Asp Ile Val Asp Ser Glu Asp Leu Thr Ile
            500                 505                 510 ctg gct ctc gta gaa gaa gac act cct gag caa cga caa caa aag agg     1584
Leu Ala Leu Val Glu Glu Asp Thr Pro Glu Gln Arg Gln Gln Lys Arg
        515                 520                 525 cag agg ttc atg gaa ata cag gag att gtt caa atg gcg ttt agt aaa     1632
Gln Arg Phe Met Glu Ile Gln Glu Ile Val Gln Met Ala Phe Ser Lys
        530                 535                 540 gac aag gag gat ctt gga aag tcg tct ctc tca gct tcg tct tct tcc     1680
Asp Lys Glu Asp Leu Gly Lys Ser Ser Leu Ser Ala Ser Ser Ser Ser
545                 550                 555                 560 aca tcc aaa tta act ggt aaa aag agg tct att gct aaa ccc tct cac     1728
Thr Ser Lys Leu Thr Gly Lys Lys Arg Ser Ile Ala Lys Pro Ser His
```

```
                          565              570              575
cgg cgt cgg tga                                                                   1740
Arg Arg Arg
```

<210> SEQ ID NO 6
<211> LENGTH: 579
<212> TYPE: PRT
<213> ORGANISM: Brassica napus

<400> SEQUENCE: 6

```
Met Glu Thr Ile Ala Xaa Phe Asp Asp Phe Tyr Glu Ile Ser Ser Thr
  1               5                  10                  15

Ser Phe Xaa Ala Ala Pro Ala Pro Thr Asp Asn Ser Gly Ser Ser Thr
             20                  25                  30

Val Xaa Pro Thr Glu Leu Xaa Thr Arg Pro Glu Val Ser Ala Phe Gln
         35                  40                  45

Leu Leu Ser Asn Ser Leu Glu Ser Val Phe Asp Ser Pro Glu Ala Phe
     50                  55                  60

Tyr Ser Asp Ala Lys Leu Val Leu Ser Asp Asp Lys Glu Val Ser Phe
 65                  70                  75                  80

His Arg Cys Ile Leu Ser Ala Arg Ser Leu Phe Phe Lys Ala Ala Leu
                 85                  90                  95

Xaa Ala Ala Glu Lys Val Gln Lys Ser Thr Pro Val Lys Leu Glu Leu
            100                 105                 110

Lys Thr Leu Ala Ala Glu Tyr Asp Val Gly Phe Asp Ser Val Val Ala
        115                 120                 125

Val Leu Ala Tyr Val Tyr Ser Gly Arg Val Arg Pro Pro Lys Gly
    130                 135                 140

Val Ser Glu Cys Ala Asp Xaa Ser Cys Cys His Val Ala Cys Arg Pro
145                 150                 155                 160

Ala Val Asp Phe Met Val Glu Val Leu Tyr Leu Ala Phe Val Phe Gln
                165                 170                 175

Ile Gln Glu Leu Val Thr Met Tyr Gln Arg His Leu Leu Asp Val Val
            180                 185                 190

Asp Lys Val Xaa Ile Glu Asp Thr Leu Val Val Leu Lys Leu Ala Asn
        195                 200                 205

Ile Cys Gly Lys Ala Cys Lys Lys Leu Phe Asp Lys Cys Arg Glu Ile
    210                 215                 220

Ile Val Lys Ser Asn Val Asp Val Val Thr Leu Lys Lys Ser Leu Pro
225                 230                 235                 240

Glu Xaa Ile Ala Lys Gln Val Ile Asp Ile Arg Lys Glu Leu Gly Leu
                245                 250                 255

Glu Val Ala Glu Pro Glu Lys His Val Ser Asn Ile His Lys Ala Leu
            260                 265                 270

Glu Ser Asp Asp Leu Asp Leu Val Met Leu Leu Lys Glu Gly His
        275                 280                 285

Thr Asn Leu Asp Glu Ala Tyr Ala Leu His Phe Ala Val Ala Tyr Cys
    290                 295                 300

Asp Glu Lys Thr Ala Arg Asn Leu Leu Glu Leu Gly Phe Ala Asp Val
305                 310                 315                 320

Asn Arg Arg Asn Pro Arg Gly Tyr Thr Val Ile His Val Ala Ala Met
                325                 330                 335

Arg Lys Glu Pro Thr Leu Ile Ala Leu Leu Leu Thr Lys Gly Ala Asn
            340                 345                 350
```

-continued

```
Ala Leu Glu Met Ser Leu Asp Gly Arg Thr Ala Leu Leu Ile Ala Lys
            355                 360                 365

Gln Val Thr Lys Ala Ala Glu Cys Cys Ile Leu Glu Lys Gly Lys Leu
        370                 375                 380

Ala Ala Lys Gly Gly Val Cys Val Glu Ile Leu Lys Gln Pro Asp Asn
385                 390                 395                 400

Thr Arg Glu Pro Phe Pro Glu Asp Val Ser Pro Ser Leu Ala Val Ala
                405                 410                 415

Ala Asp Gln Phe Lys Ile Arg Leu Ile Asp Leu Glu Asn Arg Val Gln
            420                 425                 430

Met Ala Arg Cys Leu Tyr Pro Met Glu Ala Gln Val Ala Met Asp Phe
        435                 440                 445

Ala Arg Met Lys Gly Thr Arg Glu Phe Val Val Thr Thr Ala Thr Asp
    450                 455                 460

Leu His Met Glu Pro Phe Lys Phe Val Glu Met His Gln Ser Arg Leu
465                 470                 475                 480

Thr Ala Leu Ser Lys Thr Val Glu Phe Gly Lys Arg Phe Phe Pro Arg
                485                 490                 495

Cys Ser Lys Val Leu Asp Asp Ile Val Asp Ser Glu Asp Leu Thr Ile
            500                 505                 510

Leu Ala Leu Val Glu Glu Asp Thr Pro Glu Gln Arg Gln Gln Lys Arg
        515                 520                 525

Gln Arg Phe Met Glu Ile Gln Glu Ile Val Gln Met Ala Phe Ser Lys
    530                 535                 540

Asp Lys Glu Asp Leu Gly Lys Ser Ser Leu Ser Ala Ser Ser Ser
545                 550                 555                 560

Thr Ser Lys Leu Thr Gly Lys Lys Arg Ser Ile Ala Lys Pro Ser His
                565                 570                 575

Arg Arg Arg
```

<210> SEQ ID NO 7
<211> LENGTH: 1761
<212> TYPE: DNA
<213> ORGANISM: Arabidopsis thaliana
<220> FEATURE:
<221> NAME/KEY: CDS
<222> LOCATION: (1)..(1758)
<223> OTHER INFORMATION: AtNMLc5 cDNA sequence

<400> SEQUENCE: 7

```
atg gct act ttg act gag cca tca tca tct ttg agt ttc aca tct tct      48
Met Ala Thr Leu Thr Glu Pro Ser Ser Ser Leu Ser Phe Thr Ser Ser
  1               5                  10                  15 cat ttc tct tat ggt tct att ggg tcc aat cac ttc tca tca agc tca      96
His Phe Ser Tyr Gly Ser Ile Gly Ser Asn His Phe Ser Ser Ser Ser
             20                  25                  30 gct tct aat cct gaa gtt gtt agt cta acc aaa ctc agc tcc aat ctt     144
Ala Ser Asn Pro Glu Val Val Ser Leu Thr Lys Leu Ser Ser Asn Leu
         35                  40                  45 gag cag ctt ctt agt aat tca gat tgt gat tac agt gat gca gag atc     192
Glu Gln Leu Leu Ser Asn Ser Asp Cys Asp Tyr Ser Asp Ala Glu Ile
     50                  55                  60 att gtt gat ggt gtt cca gtt ggt gtt cat aga tgc att tta gct gca     240
Ile Val Asp Gly Val Pro Val Gly Val His Arg Cys Ile Leu Ala Ala
 65                  70                  75                  80 aga agt aag ttt ttc caa gat ttg ttt aag aaa gaa aag aaa att tcg     288
Arg Ser Lys Phe Phe Gln Asp Leu Phe Lys Lys Glu Lys Lys Ile Ser
                 85                  90                  95
```

-continued

```
aaa act gag aaa cca aag tat cag ttg aga gag atg tta cct tat gga      336
Lys Thr Glu Lys Pro Lys Tyr Gln Leu Arg Glu Met Leu Pro Tyr Gly
            100                 105                 110 gct gtt gct cat gaa gct ttc ttg tat ttc ttg agt tat ata tat act      384
Ala Val Ala His Glu Ala Phe Leu Tyr Phe Leu Ser Tyr Ile Tyr Thr
                115                 120                 125 ggg aga tta aag cct ttt cca ttg gag gtt tcg act tgt gtt gat cca      432
Gly Arg Leu Lys Pro Phe Pro Leu Glu Val Ser Thr Cys Val Asp Pro
        130                 135                 140 gtt tgt tct cat gat tgt tgt cga cct gcc att gat ttt gtt gtt caa      480
Val Cys Ser His Asp Cys Cys Arg Pro Ala Ile Asp Phe Val Val Gln
145                 150                 155                 160 ttg atg tat gct tcc tct gtt ctc caa gtg cct gag cta gtt tca tct      528
Leu Met Tyr Ala Ser Ser Val Leu Gln Val Pro Glu Leu Val Ser Ser
                165                 170                 175 ttt cag cgg cgg ctt tgt aac ttt gtg gag aag acc ctt gtt gag aat      576
Phe Gln Arg Arg Leu Cys Asn Phe Val Glu Lys Thr Leu Val Glu Asn
            180                 185                 190 gtt ctt ccc att ctt atg gtt gct ttc aat tgt aag ttg act cag ctt      624
Val Leu Pro Ile Leu Met Val Ala Phe Asn Cys Lys Leu Thr Gln Leu
        195                 200                 205 ctt gat cag tgt att gag aga gtg gcg agg tca gat ctt tac agg ttc      672
Leu Asp Gln Cys Ile Glu Arg Val Ala Arg Ser Asp Leu Tyr Arg Phe
    210                 215                 220 tgt att gaa aag gaa gtt cct ccc gaa gta gca gag aag att aaa cag      720
Cys Ile Glu Lys Glu Val Pro Pro Glu Val Ala Glu Lys Ile Lys Gln
225                 230                 235                 240 ctt cga ctt ata tcc ccg caa gac gaa gaa acc agt ccc aag att tcg      768
Leu Arg Leu Ile Ser Pro Gln Asp Glu Glu Thr Ser Pro Lys Ile Ser
                245                 250                 255 gag aaa ttg ctt gaa aga atc ggt aaa att ctc aag gcc ttg gat tca      816
Glu Lys Leu Leu Glu Arg Ile Gly Lys Ile Leu Lys Ala Leu Asp Ser
            260                 265                 270 gat gat gtt gag ctt gtg aag ctt ctt ttg act gag tca gat atc act      864
Asp Asp Val Glu Leu Val Lys Leu Leu Leu Thr Glu Ser Asp Ile Thr
        275                 280                 285 cta gat caa gcc aat ggt ctg cat tat tct gtt gtg tat agt gat ccg      912
Leu Asp Gln Ala Asn Gly Leu His Tyr Ser Val Val Tyr Ser Asp Pro
    290                 295                 300 aaa gtt gtt gcc gag att ctt gct ctg gat atg ggt gat gtg aac tac      960
Lys Val Val Ala Glu Ile Leu Ala Leu Asp Met Gly Asp Val Asn Tyr
305                 310                 315                 320 agg aat tcc cgg ggt tac acg gtt ctt cat ttt gct gcg atg cgt aga     1008
Arg Asn Ser Arg Gly Tyr Thr Val Leu His Phe Ala Ala Met Arg Arg
                325                 330                 335 gag cca tcg atc att ata tcg ctt atc gat aaa ggc gcc aat gca tct     1056
Glu Pro Ser Ile Ile Ile Ser Leu Ile Asp Lys Gly Ala Asn Ala Ser
            340                 345                 350 gag ttt aca tct gac gga cgc agc gca gtt aat ata ttg aga aga ctg     1104
Glu Phe Thr Ser Asp Gly Arg Ser Ala Val Asn Ile Leu Arg Arg Leu
        355                 360                 365 aca aat cca aag gat tat cat acc aaa aca gca aaa ggg cgt gaa tct     1152
Thr Asn Pro Lys Asp Tyr His Thr Lys Thr Ala Lys Gly Arg Glu Ser
    370                 375                 380 agt aag gcc agg cta tgc atc gat ata ttg gaa aga gaa atc agg aag     1200
Ser Lys Ala Arg Leu Cys Ile Asp Ile Leu Glu Arg Glu Ile Arg Lys
385                 390                 395                 400 aac ccc atg gtt cta gat aca cca atg tgt tcc att tct atg cct gaa     1248
Asn Pro Met Val Leu Asp Thr Pro Met Cys Ser Ile Ser Met Pro Glu
```

```
gat ctc cag atg aga ctg ttg tac cta gaa aag aga gtg ggt ctt gct      1296
Asp Leu Gln Met Arg Leu Leu Tyr Leu Glu Lys Arg Val Gly Leu Ala
            420                 425                 430 cag ttg ttc ttt cca acg gaa gct aaa gtg gct atg gac att ggt aac      1344
Gln Leu Phe Phe Pro Thr Glu Ala Lys Val Ala Met Asp Ile Gly Asn
        435                 440                 445 gta gaa ggt aca agt gag ttc aca ggg ttg tca cct cct tca agt ggg      1392
Val Glu Gly Thr Ser Glu Phe Thr Gly Leu Ser Pro Pro Ser Ser Gly
    450                 455                 460 tta acc gga aac ttg agt cag gtt gat tta aac gaa act cct cat atg      1440
Leu Thr Gly Asn Leu Ser Gln Val Asp Leu Asn Glu Thr Pro His Met
465                 470                 475                 480 caa acc caa aga ctt ctt act cgt atg gtg gct cta atg aaa aca gtt      1488
Gln Thr Gln Arg Leu Leu Thr Arg Met Val Ala Leu Met Lys Thr Val
                485                 490                 495 gag act ggt cga agg ttt ttt cca tat ggt tca gag gtt cta gat aag      1536
Glu Thr Gly Arg Arg Phe Phe Pro Tyr Gly Ser Glu Val Leu Asp Lys
            500                 505                 510 tac atg gct gag tat ata gac gac gac atc ctc gac gat ttc cat ttt      1584
Tyr Met Ala Glu Tyr Ile Asp Asp Asp Ile Leu Asp Asp Phe His Phe
        515                 520                 525 gag aag gga tct aca cat gaa aga aga ttg aaa aga atg aga tat aga      1632
Glu Lys Gly Ser Thr His Glu Arg Arg Leu Lys Arg Met Arg Tyr Arg
    530                 535                 540 gag ctt aag gat gat gtc caa aag gca tat agc aaa gac aaa gag tct      1680
Glu Leu Lys Asp Asp Val Gln Lys Ala Tyr Ser Lys Asp Lys Glu Ser
545                 550                 555                 560 aag att gcg cgg tct tgt ctt tct gct tca tct tct cct tct tct tct      1728
Lys Ile Ala Arg Ser Cys Leu Ser Ala Ser Ser Ser Pro Ser Ser Ser
                565                 570                 575 tcc ata aga gat gat ctg cac aac aca aca tga                          1761
Ser Ile Arg Asp Asp Leu His Asn Thr Thr
            580                 585
```

<210> SEQ ID NO 8
<211> LENGTH: 586
<212> TYPE: PRT
<213> ORGANISM: Arabidopsis thaliana

<400> SEQUENCE: 8

```
Met Ala Thr Leu Thr Glu Pro Ser Ser Ser Leu Ser Phe Thr Ser Ser
 1               5                  10                  15

His Phe Ser Tyr Gly Ser Ile Gly Ser Asn His Phe Ser Ser Ser Ser
                20                  25                  30

Ala Ser Asn Pro Glu Val Val Ser Leu Thr Lys Leu Ser Ser Asn Leu
            35                  40                  45

Glu Gln Leu Leu Ser Asn Ser Asp Cys Asp Tyr Ser Asp Ala Glu Ile
        50                  55                  60

Ile Val Asp Gly Val Pro Val Gly Val His Arg Cys Ile Leu Ala Ala
 65                  70                  75                  80

Arg Ser Lys Phe Phe Gln Asp Leu Phe Lys Lys Glu Lys Lys Ile Ser
                85                  90                  95

Lys Thr Glu Lys Pro Lys Tyr Gln Leu Arg Glu Met Leu Pro Tyr Gly
            100                 105                 110

Ala Val Ala His Glu Ala Phe Leu Tyr Phe Leu Ser Tyr Ile Tyr Thr
        115                 120                 125

Gly Arg Leu Lys Pro Phe Pro Leu Glu Val Ser Thr Cys Val Asp Pro
```

-continued

```
            130                 135                 140
Val Cys Ser His Asp Cys Cys Arg Pro Ala Ile Asp Phe Val Val Gln
145                 150                 155                 160
Leu Met Tyr Ala Ser Ser Val Leu Gln Val Pro Glu Leu Val Ser Ser
                165                 170                 175
Phe Gln Arg Arg Leu Cys Asn Phe Val Glu Lys Thr Leu Val Glu Asn
                180                 185                 190
Val Leu Pro Ile Leu Met Val Ala Phe Asn Cys Lys Leu Thr Gln Leu
                195                 200                 205
Leu Asp Gln Cys Ile Glu Arg Val Ala Arg Ser Asp Leu Tyr Arg Phe
                210                 215                 220
Cys Ile Glu Lys Glu Val Pro Glu Val Ala Glu Lys Ile Lys Gln
225                 230                 235                 240
Leu Arg Leu Ile Ser Pro Gln Asp Glu Thr Ser Pro Lys Ile Ser
                245                 250                 255
Glu Lys Leu Leu Glu Arg Ile Gly Lys Ile Leu Lys Ala Leu Asp Ser
                260                 265                 270
Asp Asp Val Glu Leu Val Lys Leu Leu Thr Glu Ser Asp Ile Thr
                275                 280                 285
Leu Asp Gln Ala Asn Gly Leu His Tyr Ser Val Val Tyr Ser Asp Pro
                290                 295                 300
Lys Val Val Ala Glu Ile Leu Ala Leu Asp Met Gly Asp Val Asn Tyr
305                 310                 315                 320
Arg Asn Ser Arg Gly Tyr Thr Val Leu His Phe Ala Ala Met Arg Arg
                325                 330                 335
Glu Pro Ser Ile Ile Ile Ser Leu Ile Asp Lys Gly Ala Asn Ala Ser
                340                 345                 350
Glu Phe Thr Ser Asp Gly Arg Ser Ala Val Asn Ile Leu Arg Arg Leu
                355                 360                 365
Thr Asn Pro Lys Asp Tyr His Thr Lys Thr Ala Lys Gly Arg Glu Ser
370                 375                 380
Ser Lys Ala Arg Leu Cys Ile Asp Ile Leu Glu Arg Glu Ile Arg Lys
385                 390                 395                 400
Asn Pro Met Val Leu Asp Thr Pro Met Cys Ser Ile Ser Met Pro Glu
                405                 410                 415
Asp Leu Gln Met Arg Leu Leu Tyr Leu Glu Lys Arg Val Gly Leu Ala
                420                 425                 430
Gln Leu Phe Phe Pro Thr Glu Ala Lys Val Ala Met Asp Ile Gly Asn
                435                 440                 445
Val Glu Gly Thr Ser Glu Phe Thr Gly Leu Ser Pro Pro Ser Ser Gly
450                 455                 460
Leu Thr Gly Asn Leu Ser Gln Val Asp Leu Asn Glu Thr Pro His Met
465                 470                 475                 480
Gln Thr Gln Arg Leu Leu Thr Arg Met Val Ala Leu Met Lys Thr Val
                485                 490                 495
Glu Thr Gly Arg Arg Phe Phe Pro Tyr Gly Ser Glu Val Leu Asp Lys
                500                 505                 510
Tyr Met Ala Glu Tyr Ile Asp Asp Ile Leu Asp Asp Phe His Phe
                515                 520                 525
Glu Lys Gly Ser Thr His Glu Arg Arg Leu Lys Arg Met Arg Tyr Arg
                530                 535                 540
Glu Leu Lys Asp Asp Val Gln Lys Ala Tyr Ser Lys Asp Lys Glu Ser
545                 550                 555                 560
```

```
Lys Ile Ala Arg Ser Cys Leu Ser Ala Ser Ser Ser Pro Ser Ser Ser
            565                 570                 575

Ser Ile Arg Asp Asp Leu His Asn Thr Thr
            580                 585
```

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: PCR Primer

<400> SEQUENCE: 9
agattattgt caagtctaat g                                            21

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: PCR Primer

<400> SEQUENCE: 10
ttccatgtac ctttgcttc                                               19

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: PCR Primer

<400> SEQUENCE: 11
gcggatccat ggataatagt agg                                          23

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: PCR Primer

<400> SEQUENCE: 12
gcggatccta tttcctaaaa ggg                                          23

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: PCR Primer

<400> SEQUENCE: 13
tcaaggcctt ggattcagat g                                            21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: PCR Primer

<400> SEQUENCE: 14
attaactgcg ctacgtccgt c                                            21

-continued

```
<210> SEQ ID NO 15
<211> LENGTH: 1477
<212> TYPE: DNA
<213> ORGANISM: Arabidopsis thaliana
<220> FEATURE:
<221> NAME/KEY: CDS
<222> LOCATION: (1)..(1476)
<223> OTHER INFORMATION: AtNMLc2 genomic sequence

<400> SEQUENCE: 15 atg agc aat ctt gaa gaa tct ttg aga tct cta tcg ttg gat ttc ctg      48
Met Ser Asn Leu Glu Glu Ser Leu Arg Ser Leu Ser Leu Asp Phe Leu
 1               5                  10                  15 aac cta cta atc aac ggt caa gct ttc tcc gac gtg act ttc agc gtt      96
Asn Leu Leu Ile Asn Gly Gln Ala Phe Ser Asp Val Thr Phe Ser Val
             20                  25                  30 gaa ggt cgt tta gtc cac gct cac cgt tgt atc ctc gcc gca cgg agt     144
Glu Gly Arg Leu Val His Ala His Arg Cys Ile Leu Ala Ala Arg Ser
         35                  40                  45 ctt ttc ttc cgc aaa ttc ttt tgt ggg aca gac tca cca caa cct gtc     192
Leu Phe Phe Arg Lys Phe Phe Cys Gly Thr Asp Ser Pro Gln Pro Val
     50                  55                  60 aca ggt ata gac ccg acc caa cat ggg tcc gta ccc gct agc cca aca     240
Thr Gly Ile Asp Pro Thr Gln His Gly Ser Val Pro Ala Ser Pro Thr
 65                  70                  75                  80 aga ggc tcc acg gcc cca gct gga att ata cca gtg aac tca gtc ggt     288
Arg Gly Ser Thr Ala Pro Ala Gly Ile Ile Pro Val Asn Ser Val Gly
                 85                  90                  95 tat gag gtt ttt ctg ttg cta ctt cag ttt ctt tat agc gga caa gtc     336
Tyr Glu Val Phe Leu Leu Leu Gln Phe Leu Tyr Ser Gly Gln Val
            100                 105                 110 tcc atc gtg ccg cag aaa cac gag cct aga cct aat tgt ggc gag aga     384
Ser Ile Val Pro Gln Lys His Glu Pro Arg Pro Asn Cys Gly Glu Arg
        115                 120                 125 gga tgt tgg cac act cat tgc tca gcc gcc gtt gat ctt gct ctt gat     432
Gly Cys Trp His Thr His Cys Ser Ala Ala Val Asp Leu Ala Leu Asp
    130                 135                 140 act ctc gcc gcc tct cgt tac ttc ggc gtc gag cag ctc gca ttg ctc     480
Thr Leu Ala Ala Ser Arg Tyr Phe Gly Val Glu Gln Leu Ala Leu Leu
145                 150                 155                 160 acc cag aaa caa ttg gca agc atg gtg gag aaa gcc tct atc gaa gat     528
Thr Gln Lys Gln Leu Ala Ser Met Val Glu Lys Ala Ser Ile Glu Asp
                165                 170                 175 gtg atg aaa gtt tta ata gca tca aga aag caa gac atg cat caa tta     576
Val Met Lys Val Leu Ile Ala Ser Arg Lys Gln Asp Met His Gln Leu
            180                 185                 190 tgg acc acc tgc tct cac tta gtt atg agc aat ctt gaa gaa tct ttg     624
Trp Thr Thr Cys Ser His Leu Val Met Ser Asn Leu Glu Glu Ser Leu
        195                 200                 205 aga tct cta tcg ttg gat ttc ctg aac cta cta atc aac ggt caa gct     672
Arg Ser Leu Ser Leu Asp Phe Leu Asn Leu Leu Ile Asn Gly Gln Ala
    210                 215                 220 ttc tcc gac gtg act ttc agc gtt gaa ggt cgt tta gtc cac gct cac     720
Phe Ser Asp Val Thr Phe Ser Val Glu Gly Arg Leu Val His Ala His
225                 230                 235                 240 cgt tgt atc ctc gcc gca cgg agt ctt ttc ttc cgc aaa ttc ttt tgt     768
Arg Cys Ile Leu Ala Ala Arg Ser Leu Phe Phe Arg Lys Phe Phe Cys
                245                 250                 255 ggg aca gac tca cca caa cct gtc aca ggt ata gac ccg acc caa cat     816
Gly Thr Asp Ser Pro Gln Pro Val Thr Gly Ile Asp Pro Thr Gln His
            260                 265                 270
```

-continued

```
ggg tcc gta ccc gct agc cca aca aga ggc tcc acg gcc cca gct gga      864
Gly Ser Val Pro Ala Ser Pro Thr Arg Gly Ser Thr Ala Pro Ala Gly
        275                 280                 285 att ata cca gtg aac tca gtc ggt tat gag gtt ttt ctg ttg cta ctt      912
Ile Ile Pro Val Asn Ser Val Gly Tyr Glu Val Phe Leu Leu Leu Leu
290                 295                 300 cag ttt ctt tat agc gga caa gtc tcc atc gtg ccg cag aaa cac gag      960
Gln Phe Leu Tyr Ser Gly Gln Val Ser Ile Val Pro Gln Lys His Glu
305                 310                 315                 320 cct aga cct aat tgt ggc gag aga gga tgt tgg cac act cat tgc tca     1008
Pro Arg Pro Asn Cys Gly Glu Arg Gly Cys Trp His Thr His Cys Ser
                325                 330                 335 gcc gcc gtt gat ctt gct ctt gat act ctc gcc gcc tct cgt tac ttc     1056
Ala Ala Val Asp Leu Ala Leu Asp Thr Leu Ala Ala Ser Arg Tyr Phe
            340                 345                 350 ggc gtc gag cag ctc gca ttg ctc acc cag aaa caa ttg gca agc atg     1104
Gly Val Glu Gln Leu Ala Leu Leu Thr Gln Lys Gln Leu Ala Ser Met
        355                 360                 365 gtg gag aaa gcc tct atc gaa gat gtg atg aaa gtt tta ata gca tca     1152
Val Glu Lys Ala Ser Ile Glu Asp Val Met Lys Val Leu Ile Ala Ser
370                 375                 380 aga aag caa gac atg cat caa tta tgg acc acc tgc tct cac tta gtt     1200
Arg Lys Gln Asp Met His Gln Leu Trp Thr Thr Cys Ser His Leu Val
385                 390                 395                 400 atg agc aat ctt gaa gaa tct ttg aga tct cta tcg ttg gat ttc ctg     1248
Met Ser Asn Leu Glu Glu Ser Leu Arg Ser Leu Ser Leu Asp Phe Leu
                405                 410                 415 aac cta cta atc aac ggt caa gct ttc tcc gac gtg act ttc agc gtt     1296
Asn Leu Leu Ile Asn Gly Gln Ala Phe Ser Asp Val Thr Phe Ser Val
            420                 425                 430 gaa ggt cgt tta gtc cac gct cac cgt tgt atc ctc gcc gca cgg agt     1344
Glu Gly Arg Leu Val His Ala His Arg Cys Ile Leu Ala Ala Arg Ser
        435                 440                 445 ctt ttc ttc cgc aaa ttc ttt tgt ggg aca gac tca cca caa cct gtc     1392
Leu Phe Phe Arg Lys Phe Phe Cys Gly Thr Asp Ser Pro Gln Pro Val
450                 455                 460 aca ggt ata gac ccg acc caa cat ggg tcc gta ccc gct agc cca aca     1440
Thr Gly Ile Asp Pro Thr Gln His Gly Ser Val Pro Ala Ser Pro Thr
465                 470                 475                 480 aga ggc tcc acg gcc cca gct gga att ata cca gtg a                   1477
Arg Gly Ser Thr Ala Pro Ala Gly Ile Ile Pro Val
                485                 490
```

<210> SEQ ID NO 16
<211> LENGTH: 492
<212> TYPE: PRT
<213> ORGANISM: Arabidopsis thaliana

<400> SEQUENCE: 16

```
Met Ser Asn Leu Glu Glu Ser Leu Arg Ser Leu Ser Leu Asp Phe Leu
1               5                   10                  15

Asn Leu Leu Ile Asn Gly Gln Ala Phe Ser Asp Val Thr Phe Ser Val
            20                  25                  30

Glu Gly Arg Leu Val His Ala His Arg Cys Ile Leu Ala Ala Arg Ser
        35                  40                  45

Leu Phe Phe Arg Lys Phe Phe Cys Gly Thr Asp Ser Pro Gln Pro Val
    50                  55                  60

Thr Gly Ile Asp Pro Thr Gln His Gly Ser Val Pro Ala Ser Pro Thr
65                  70                  75                  80
```

```
Arg Gly Ser Thr Ala Pro Ala Gly Ile Ile Pro Val Asn Ser Val Gly
                85                  90                  95
Tyr Glu Val Phe Leu Leu Leu Gln Phe Leu Tyr Ser Gly Gln Val
            100                 105                 110
Ser Ile Val Pro Gln Lys His Glu Pro Arg Pro Asn Cys Gly Glu Arg
            115                 120                 125
Gly Cys Trp His Thr His Cys Ser Ala Ala Val Asp Leu Ala Leu Asp
        130                 135                 140
Thr Leu Ala Ala Ser Arg Tyr Phe Gly Val Glu Gln Leu Ala Leu Leu
145                 150                 155                 160
Thr Gln Lys Gln Leu Ala Ser Met Val Glu Lys Ala Ser Ile Glu Asp
                165                 170                 175
Val Met Lys Val Leu Ile Ala Ser Arg Lys Gln Asp Met His Gln Leu
            180                 185                 190
Trp Thr Thr Cys Ser His Leu Val Met Ser Asn Leu Glu Glu Ser Leu
        195                 200                 205
Arg Ser Leu Ser Leu Asp Phe Leu Asn Leu Leu Ile Asn Gly Gln Ala
        210                 215                 220
Phe Ser Asp Val Thr Phe Ser Val Glu Gly Arg Leu Val His Ala His
225                 230                 235                 240
Arg Cys Ile Leu Ala Ala Arg Ser Leu Phe Phe Arg Lys Phe Phe Cys
                245                 250                 255
Gly Thr Asp Ser Pro Gln Pro Val Thr Gly Ile Asp Pro Thr Gln His
                260                 265                 270
Gly Ser Val Pro Ala Ser Pro Thr Arg Gly Ser Thr Ala Pro Ala Gly
            275                 280                 285
Ile Ile Pro Val Asn Ser Val Gly Tyr Glu Val Phe Leu Leu Leu
            290                 295                 300
Gln Phe Leu Tyr Ser Gly Gln Val Ser Ile Val Pro Gln Lys His Glu
305                 310                 315                 320
Pro Arg Pro Asn Cys Gly Glu Arg Gly Cys Trp His Thr His Cys Ser
                325                 330                 335
Ala Ala Val Asp Leu Ala Leu Asp Thr Leu Ala Ala Ser Arg Tyr Phe
            340                 345                 350
Gly Val Glu Gln Leu Ala Leu Leu Thr Gln Lys Gln Leu Ala Ser Met
            355                 360                 365
Val Glu Lys Ala Ser Ile Glu Asp Val Met Lys Val Leu Ile Ala Ser
            370                 375                 380
Arg Lys Gln Asp Met His Gln Leu Trp Thr Thr Cys Ser His Leu Val
385                 390                 395                 400
Met Ser Asn Leu Glu Glu Ser Leu Arg Ser Leu Ser Leu Asp Phe Leu
                405                 410                 415
Asn Leu Leu Ile Asn Gly Gln Ala Phe Ser Asp Val Thr Phe Ser Val
                420                 425                 430
Glu Gly Arg Leu Val His Ala His Arg Cys Ile Leu Ala Ala Arg Ser
            435                 440                 445
Leu Phe Phe Arg Lys Phe Phe Cys Gly Thr Asp Ser Pro Gln Pro Val
            450                 455                 460
Thr Gly Ile Asp Pro Thr Gln His Gly Ser Val Pro Ala Ser Pro Thr
465                 470                 475                 480
Arg Gly Ser Thr Ala Pro Ala Gly Ile Ile Pro Val
                485                 490
```

```
<210> SEQ ID NO 17
<211> LENGTH: 1804
<212> TYPE: DNA
<213> ORGANISM: Arabidopsis thaliana
<220> FEATURE:
<221> NAME/KEY: CDS
<222> LOCATION: (1)..(1803)
<223> OTHER INFORMATION: AtNMLc4-1 genomic sequence

<400> SEQUENCE: 17 atg gct gca act gca ata gag cca tct tca tct ata agt ttc aca tct      48
Met Ala Ala Thr Ala Ile Glu Pro Ser Ser Ser Ile Ser Phe Thr Ser
 1               5                  10                  15 tct cac tta tca aac cct tct cct gtt gtt act act tat cac tca gct      96
Ser His Leu Ser Asn Pro Ser Pro Val Val Thr Thr Tyr His Ser Ala
             20                  25                  30 gct aat ctt gaa gag ctc agc tct aac ttg gag cag ctt ctc act aat     144
Ala Asn Leu Glu Glu Leu Ser Ser Asn Leu Glu Gln Leu Leu Thr Asn
         35                  40                  45 cca gat tgc gat tac act gac gca gag atc atc att gaa gaa gaa gct     192
Pro Asp Cys Asp Tyr Thr Asp Ala Glu Ile Ile Ile Glu Glu Glu Ala
     50                  55                  60 aac cct gtg agt gtt cat aga tgt gtt tta gct gct agg agc aag ttt     240
Asn Pro Val Ser Val His Arg Cys Val Leu Ala Ala Arg Ser Lys Phe
 65                  70                  75                  80 ttt ctt gat ctg ttt aag aaa gat aaa gat agt agt gag aag aaa cct     288
Phe Leu Asp Leu Phe Lys Lys Asp Lys Asp Ser Ser Glu Lys Lys Pro
                 85                  90                  95 aag tat caa atg aaa gat tta tta cca tat gga aat gtg gga cgt gag     336
Lys Tyr Gln Met Lys Asp Leu Leu Pro Tyr Gly Asn Val Gly Arg Glu
            100                 105                 110 gca ttt ctg cat ttc ttg agc tat atc tac act ggg agg tta aag cct     384
Ala Phe Leu His Phe Leu Ser Tyr Ile Tyr Thr Gly Arg Leu Lys Pro
        115                 120                 125 ttt cct atc gag gtt tca act tgt gtt gat tca gtt tgt gct cat gat     432
Phe Pro Ile Glu Val Ser Thr Cys Val Asp Ser Val Cys Ala His Asp
    130                 135                 140 tct tgt aaa ccg gcc att gat ttt gct gtt gag ttg atg tat gct tca     480
Ser Cys Lys Pro Ala Ile Asp Phe Ala Val Glu Leu Met Tyr Ala Ser
145                 150                 155                 160 ttt gtg ttc caa atc ccg gat ctt gtt tcg tca ttt cag cgg aag ctt     528
Phe Val Phe Gln Ile Pro Asp Leu Val Ser Ser Phe Gln Arg Lys Leu
                165                 170                 175 cgt aac tat gtt gag aag tca cta gta gag aat gtt ctt cct atc ctc     576
Arg Asn Tyr Val Glu Lys Ser Leu Val Glu Asn Val Leu Pro Ile Leu
            180                 185                 190 tta gtt gcg ttt cat tgt gat ttg aca cag ctt ctt gat caa tgc att     624
Leu Val Ala Phe His Cys Asp Leu Thr Gln Leu Leu Asp Gln Cys Ile
        195                 200                 205 gag aga gtg gcg aga tca gac tta gac aga ttc tgt atc gaa aag gag     672
Glu Arg Val Ala Arg Ser Asp Leu Asp Arg Phe Cys Ile Glu Lys Glu
    210                 215                 220 ctt cct tta gaa gta ttg gaa aaa atc aaa cag ctt cga gtt aag tcg     720
Leu Pro Leu Glu Val Leu Glu Lys Ile Lys Gln Leu Arg Val Lys Ser
225                 230                 235                 240 gtg aac ata ccc gag gtg gag gat aaa tcg ata gag aga aca ggg aaa     768
Val Asn Ile Pro Glu Val Glu Asp Lys Ser Ile Glu Arg Thr Gly Lys
                245                 250                 255 gta ctc aag gca ttg gat tca gat gat gta gaa ctc gtg aag ctt ctt     816
Val Leu Lys Ala Leu Asp Ser Asp Asp Val Glu Leu Val Lys Leu Leu
            260                 265                 270
```

```
ttg act gag tca gat ata act cta gac caa gcc aat ggt cta cat tat      864
Leu Thr Glu Ser Asp Ile Thr Leu Asp Gln Ala Asn Gly Leu His Tyr
        275                 280                 285 gca gtg gca tac agt gat ccg aaa gtt gtg aca cag gtt ctt gat cta      912
Ala Val Ala Tyr Ser Asp Pro Lys Val Val Thr Gln Val Leu Asp Leu
        290                 295                 300 gat atg gct gat gtt aat ttc aga aat tcc agg ggg tat acg gtt ctt      960
Asp Met Ala Asp Val Asn Phe Arg Asn Ser Arg Gly Tyr Thr Val Leu
305                 310                 315                 320 cat att gct gct atg cgt aga gag cca aca att atc ata cca ctt att     1008
His Ile Ala Ala Met Arg Arg Glu Pro Thr Ile Ile Ile Pro Leu Ile
                325                 330                 335 caa aaa gga gct aat gct tca gat ttc acg ttt gat gga cgc agt gcg     1056
Gln Lys Gly Ala Asn Ala Ser Asp Phe Thr Phe Asp Gly Arg Ser Ala
        340                 345                 350 gta aat ata tgt agg aga ctc act agg ccg aaa gat tat cat acc aaa     1104
Val Asn Ile Cys Arg Arg Leu Thr Arg Pro Lys Asp Tyr His Thr Lys
        355                 360                 365 acc tca agg aaa gaa cct agt aaa tac cgc tta tgc atc gat atc ttg     1152
Thr Ser Arg Lys Glu Pro Ser Lys Tyr Arg Leu Cys Ile Asp Ile Leu
        370                 375                 380 gaa agg gaa att aga agg aat cca ttg gtt agt ggg gat aca ccc act     1200
Glu Arg Glu Ile Arg Arg Asn Pro Leu Val Ser Gly Asp Thr Pro Thr
385                 390                 395                 400 tgt tcc cat tcg atg ccc gag gat ctc caa atg agg ttg tta tac tta     1248
Cys Ser His Ser Met Pro Glu Asp Leu Gln Met Arg Leu Leu Tyr Leu
                405                 410                 415 gaa aag cga tgg gac ttg cgt cag ttg ttc ttc cca gca gaa gcc aat     1296
Glu Lys Arg Trp Asp Leu Arg Gln Leu Phe Phe Pro Ala Glu Ala Asn
                420                 425                 430 gtg gct atg gac gtt gct aat gtt gaa ggg aca agc gag tgc aca ggt     1344
Val Ala Met Asp Val Ala Asn Val Glu Gly Thr Ser Glu Cys Thr Gly
        435                 440                 445 ctt cta act cca cct cca tca aat gat aca act gaa aac ttg ggt aaa     1392
Leu Leu Thr Pro Pro Pro Ser Asn Asp Thr Thr Glu Asn Leu Gly Lys
        450                 455                 460 gtc gat tta aat gaa acg cct tat gtg caa acg aaa aga atg ctt aca     1440
Val Asp Leu Asn Glu Thr Pro Tyr Val Gln Thr Lys Arg Met Leu Thr
465                 470                 475                 480 cgt atg aaa gcc ctc atg aaa aca ggt aaa agc tta agg aaa tgt act     1488
Arg Met Lys Ala Leu Met Lys Thr Gly Lys Ser Leu Arg Lys Cys Thr
                485                 490                 495 ttc aag ttt tat tct ctg acc aca aga ttg act gat tcg aaa ccg ttc     1536
Phe Lys Phe Tyr Ser Leu Thr Thr Arg Leu Thr Asp Ser Lys Pro Phe
                500                 505                 510 aac aac gca gtt gag aca ggt cgg aga tac ttc cca tct tgt tat gag     1584
Asn Asn Ala Val Glu Thr Gly Arg Arg Tyr Phe Pro Ser Cys Tyr Glu
        515                 520                 525 gtt ctg gat aag tac atg gat cag tat atg gac gaa gaa atc cct gat     1632
Val Leu Asp Lys Tyr Met Asp Gln Tyr Met Asp Glu Glu Ile Pro Asp
        530                 535                 540 atg tcg tat ccc gag aaa ggc act gtg aaa gag aga aga cag aag agg     1680
Met Ser Tyr Pro Glu Lys Gly Thr Val Lys Glu Arg Arg Gln Lys Arg
545                 550                 555                 560 atg aga tat aac gag ctg aag aac gac gtt aaa aaa gca tat agc aaa     1728
Met Arg Tyr Asn Glu Leu Lys Asn Asp Val Lys Lys Ala Tyr Ser Lys
                565                 570                 575 gac aaa gtc gcg cgg tct tgt ctt tct tct tca tca cca gct tct tct     1776
Asp Lys Val Ala Arg Ser Cys Leu Ser Ser Ser Ser Pro Ala Ser Ser
```

-continued

```
                      580             585             590
ctt aga gaa gcc tta gag aat cca aca t                              1804
Leu Arg Glu Ala Leu Glu Asn Pro Thr
            595             600
```

<210> SEQ ID NO 18
<211> LENGTH: 601
<212> TYPE: PRT
<213> ORGANISM: Arabidopsis thaliana

<400> SEQUENCE: 18

```
Met Ala Ala Thr Ala Ile Glu Pro Ser Ser Ile Ser Phe Thr Ser
 1               5                  10                  15

Ser His Leu Ser Asn Pro Ser Pro Val Val Thr Thr Tyr His Ser Ala
                20                  25                  30

Ala Asn Leu Glu Glu Leu Ser Ser Asn Leu Glu Gln Leu Leu Thr Asn
            35                  40                  45

Pro Asp Cys Asp Tyr Thr Asp Ala Glu Ile Ile Glu Glu Ala
     50                  55                  60

Asn Pro Val Ser Val His Arg Cys Val Leu Ala Ala Arg Ser Lys Phe
 65                  70                  75                  80

Phe Leu Asp Leu Phe Lys Lys Asp Lys Asp Ser Ser Glu Lys Lys Pro
                 85                  90                  95

Lys Tyr Gln Met Lys Asp Leu Leu Pro Tyr Gly Asn Val Gly Arg Glu
                100                 105                 110

Ala Phe Leu His Phe Leu Ser Tyr Ile Tyr Thr Gly Arg Leu Lys Pro
            115                 120                 125

Phe Pro Ile Glu Val Ser Thr Cys Val Asp Ser Val Cys Ala His Asp
     130                 135                 140

Ser Cys Lys Pro Ala Ile Asp Phe Ala Val Glu Leu Met Tyr Ala Ser
145                 150                 155                 160

Phe Val Phe Gln Ile Pro Asp Leu Val Ser Ser Phe Gln Arg Lys Leu
                165                 170                 175

Arg Asn Tyr Val Glu Lys Ser Leu Val Glu Asn Val Leu Pro Ile Leu
                180                 185                 190

Leu Val Ala Phe His Cys Asp Leu Thr Gln Leu Leu Asp Gln Cys Ile
            195                 200                 205

Glu Arg Val Ala Arg Ser Asp Leu Asp Arg Phe Cys Ile Glu Lys Glu
     210                 215                 220

Leu Pro Leu Glu Val Leu Glu Lys Ile Lys Gln Leu Arg Val Lys Ser
225                 230                 235                 240

Val Asn Ile Pro Glu Val Glu Asp Lys Ser Ile Glu Arg Thr Gly Lys
                245                 250                 255

Val Leu Lys Ala Leu Asp Ser Asp Val Glu Leu Val Lys Leu Leu
                260                 265                 270

Leu Thr Glu Ser Asp Ile Thr Leu Asp Gln Ala Asn Gly Leu His Tyr
            275                 280                 285

Ala Val Ala Tyr Ser Asp Pro Lys Val Val Thr Gln Val Leu Asp Leu
     290                 295                 300

Asp Met Ala Asp Val Asn Phe Arg Asn Ser Arg Gly Tyr Thr Val Leu
305                 310                 315                 320

His Ile Ala Ala Met Arg Arg Glu Pro Thr Ile Ile Pro Leu Ile
                325                 330                 335

Gln Lys Gly Ala Asn Ala Ser Asp Phe Thr Phe Asp Gly Arg Ser Ala
            340                 345                 350
```

```
Val Asn Ile Cys Arg Arg Leu Thr Arg Pro Lys Asp Tyr His Thr Lys
            355                 360                 365

Thr Ser Arg Lys Glu Pro Ser Lys Tyr Arg Leu Cys Ile Asp Ile Leu
    370                 375                 380

Glu Arg Glu Ile Arg Arg Asn Pro Leu Val Ser Gly Asp Thr Pro Thr
385                 390                 395                 400

Cys Ser His Ser Met Pro Glu Asp Leu Gln Met Arg Leu Leu Tyr Leu
                405                 410                 415

Glu Lys Arg Trp Asp Leu Arg Gln Leu Phe Phe Pro Ala Glu Ala Asn
            420                 425                 430

Val Ala Met Asp Val Ala Asn Val Glu Gly Thr Ser Glu Cys Thr Gly
        435                 440                 445

Leu Leu Thr Pro Pro Ser Asn Asp Thr Thr Glu Asn Leu Gly Lys
    450                 455                 460

Val Asp Leu Asn Glu Thr Pro Tyr Val Gln Thr Lys Arg Met Leu Thr
465                 470                 475                 480

Arg Met Lys Ala Leu Met Lys Thr Gly Lys Ser Leu Arg Lys Cys Thr
                485                 490                 495

Phe Lys Phe Tyr Ser Leu Thr Thr Arg Leu Thr Asp Ser Lys Pro Phe
            500                 505                 510

Asn Asn Ala Val Glu Thr Gly Arg Arg Tyr Phe Pro Ser Cys Tyr Glu
        515                 520                 525

Val Leu Asp Lys Tyr Met Asp Gln Tyr Met Asp Glu Ile Pro Asp
    530                 535                 540

Met Ser Tyr Pro Glu Lys Gly Thr Val Lys Glu Arg Arg Gln Lys Arg
545                 550                 555                 560

Met Arg Tyr Asn Glu Leu Lys Asn Asp Val Lys Lys Ala Tyr Ser Lys
                565                 570                 575

Asp Lys Val Ala Arg Ser Cys Leu Ser Ser Ser Pro Ala Ser Ser
            580                 585                 590

Leu Arg Glu Ala Leu Glu Asn Pro Thr
    595                 600

<210> SEQ ID NO 19
<211> LENGTH: 1803
<212> TYPE: DNA
<213> ORGANISM: Arabidopsis thaliana
<220> FEATURE:
<221> NAME/KEY: CDS
<222> LOCATION: (1)..(1803)
<223> OTHER INFORMATION: AtNMLc4-2 genomic sequence

<400> SEQUENCE: 19 atg gcc acc acc acc acc acc acc gct aga ttc tct gat tca tac        48
Met Ala Thr Thr Thr Thr Thr Thr Ala Arg Phe Ser Asp Ser Tyr
1               5                   10                  15 gag ttc agc aac aca agc ggc aat agc ttc ttc gcc gcc gag tca tct    96
Glu Phe Ser Asn Thr Ser Gly Asn Ser Phe Phe Ala Ala Glu Ser Ser
                20                  25                  30 ctt gat tat ccg acg gaa ttt ctc acg cca ccg gag gta tca gct ctt    144
Leu Asp Tyr Pro Thr Glu Phe Leu Thr Pro Pro Glu Val Ser Ala Leu
            35                  40                  45 aaa ctt ctg tct aac tgc ctc gag tct gtt ttc gac tcg ccg gag acg    192
Lys Leu Leu Ser Asn Cys Leu Glu Ser Val Phe Asp Ser Pro Glu Thr
        50                  55                  60 ttc tac agc gat gct aag cta gtt ctc gcc ggc ggc cgg gaa gtt tct    240
Phe Tyr Ser Asp Ala Lys Leu Val Leu Ala Gly Gly Arg Glu Val Ser
```

-continued

```
               65                  70                  75                  80
ttt cac cgt tgt att ctt tcc gcg aga att cct gtc ttc aaa agc gct      288
Phe His Arg Cys Ile Leu Ser Ala Arg Ile Pro Val Phe Lys Ser Ala
                 85                  90                  95 tta gcc acc gtg aag gaa caa aaa tcc tcc acc acc gtg aag ctc cag      336
Leu Ala Thr Val Lys Glu Gln Lys Ser Ser Thr Thr Val Lys Leu Gln
            100                 105                 110 ctg aaa gag atc gcc aga gat tac gaa gtc ggc ttt gac tcg gtt gtg      384
Leu Lys Glu Ile Ala Arg Asp Tyr Glu Val Gly Phe Asp Ser Val Val
            115                 120                 125 gcg gtt ttg gcg tat gtt tac agc ggc aga gtg agg tcc ccg ccg aag      432
Ala Val Leu Ala Tyr Val Tyr Ser Gly Arg Val Arg Ser Pro Pro Lys
            130                 135                 140 gga gct tct gct tgc gta gac gac gat tgt tgc cac gtg gct tgc cgg      480
Gly Ala Ser Ala Cys Val Asp Asp Asp Cys Cys His Val Ala Cys Arg
145                 150                 155                 160 tca aag gtg gat ttc atg gtg gag gtt ctt tat ctg tct ttc gtt ttc      528
Ser Lys Val Asp Phe Met Val Glu Val Leu Tyr Leu Ser Phe Val Phe
                165                 170                 175 cag att caa gaa tta gtt act ctg tat gag agg cag ttc ttg gaa att      576
Gln Ile Gln Glu Leu Val Thr Leu Tyr Glu Arg Gln Phe Leu Glu Ile
            180                 185                 190 gta gac aaa gtt gta gtc gaa gac atc ttg gtt ata ttc aag ctt gat      624
Val Asp Lys Val Val Val Glu Asp Ile Leu Val Ile Phe Lys Leu Asp
            195                 200                 205 act cta tgt ggt aca aca tac aag aag ctt ttg gat aga tgc ata gaa      672
Thr Leu Cys Gly Thr Thr Tyr Lys Lys Leu Leu Asp Arg Cys Ile Glu
    210                 215                 220 att atc gtg aag tct gat ata gaa cta gtt agt ctt gag aag tct tta      720
Ile Ile Val Lys Ser Asp Ile Glu Leu Val Ser Leu Glu Lys Ser Leu
225                 230                 235                 240 cct caa cac att ttc aag caa atc ata gac atc cgc gaa gcg ctc tgt      768
Pro Gln His Ile Phe Lys Gln Ile Ile Asp Ile Arg Glu Ala Leu Cys
                245                 250                 255 cta gag cca cct aaa cta gaa agg cat gtc aag aac ata tac aag gcg      816
Leu Glu Pro Pro Lys Leu Glu Arg His Val Lys Asn Ile Tyr Lys Ala
            260                 265                 270 cta gac tca gat gat gtt gag ctt gtc aag atg ctt ttg cta gaa gga      864
Leu Asp Ser Asp Asp Val Glu Leu Val Lys Met Leu Leu Leu Glu Gly
            275                 280                 285 cac acc aat ctc gat gag gcg tat gct ctt cat ttt gct atc gct cac      912
His Thr Asn Leu Asp Glu Ala Tyr Ala Leu His Phe Ala Ile Ala His
            290                 295                 300 tgc gct gtg aag acc gcg tat gat ctc ctc gag ctt gag ctt gcg gat      960
Cys Ala Val Lys Thr Ala Tyr Asp Leu Leu Glu Leu Glu Leu Ala Asp
305                 310                 315                 320 gtt aac ctt aga aat ccg agg gga tac act gtg ctt cat gtt gct gcg     1008
Val Asn Leu Arg Asn Pro Arg Gly Tyr Thr Val Leu His Val Ala Ala
            325                 330                 335 atg cgg aag gag ccg aag ttg ata ata tct ttg tta atg aaa ggg gca     1056
Met Arg Lys Glu Pro Lys Leu Ile Ile Ser Leu Leu Met Lys Gly Ala
            340                 345                 350 aat att tta gac aca aca ttg gat ggt aga acc gct tta gtg att gta     1104
Asn Ile Leu Asp Thr Thr Leu Asp Gly Arg Thr Ala Leu Val Ile Val
            355                 360                 365 aaa cga ctc act aaa gcg gat gac tac aaa act agt acg gag gac ggt     1152
Lys Arg Leu Thr Lys Ala Asp Asp Tyr Lys Thr Ser Thr Glu Asp Gly
    370                 375                 380 acg cct tct ctg aaa ggc gga tta tgc ata gag gta ctt gag cat gaa     1200
```

```
Thr Pro Ser Leu Lys Gly Gly Leu Cys Ile Glu Val Leu His Glu
385                 390                 395                 400 caa aaa cta gaa tat ttg tcg cct ata gag gct tca ctt tct ctt cca      1248
Gln Lys Leu Glu Tyr Leu Ser Pro Ile Glu Ala Ser Leu Ser Leu Pro
                405                 410                 415 gta act cca gag gag ttg agg atg agg ttg ctc tat tat gaa aac cga      1296
Val Thr Pro Glu Glu Leu Arg Met Arg Leu Leu Tyr Tyr Glu Asn Arg
            420                 425                 430 gtt gca ctt gct cga ctt ctc ttt cca gtg gaa act gaa act gta cag      1344
Val Ala Leu Ala Arg Leu Leu Phe Pro Val Glu Thr Glu Thr Val Gln
        435                 440                 445 ggt att gcc aaa ttg gag gaa aca tgc gag ttt aca gct tct agt ctc      1392
Gly Ile Ala Lys Leu Glu Glu Thr Cys Glu Phe Thr Ala Ser Ser Leu
    450                 455                 460 gag cct gat cat cac att ggt gaa aag cgg aca tca cta gac cta aat      1440
Glu Pro Asp His His Ile Gly Glu Lys Arg Thr Ser Leu Asp Leu Asn
465                 470                 475                 480 atg gcg ccg ttc caa atc cat gag aag cat ttg agt aga cta aga gca      1488
Met Ala Pro Phe Gln Ile His Glu Lys His Leu Ser Arg Leu Arg Ala
                485                 490                 495 ctt tgt aaa acc gtg gaa ctg ggg aaa cgc tac ttc aaa cga tgt tcg      1536
Leu Cys Lys Thr Val Glu Leu Gly Lys Arg Tyr Phe Lys Arg Cys Ser
            500                 505                 510 ctt gat cac ttt atg gat act gag gac ttg aat cat ctt gct agc gta      1584
Leu Asp His Phe Met Asp Thr Glu Asp Leu Asn His Leu Ala Ser Val
        515                 520                 525 gaa gaa gat act cct gag aaa cgg cta caa aag aag caa agg tac atg      1632
Glu Glu Asp Thr Pro Glu Lys Arg Leu Gln Lys Lys Gln Arg Tyr Met
    530                 535                 540 gaa cta caa gag act ctg atg aag acc ttt agt gag gac aag gag gaa      1680
Glu Leu Gln Glu Thr Leu Met Lys Thr Phe Ser Glu Asp Lys Glu Glu
545                 550                 555                 560 tgt gga aag tct tcc aca ccg aaa cca acc tct gcg gtg agg tct aat      1728
Cys Gly Lys Ser Ser Thr Pro Lys Pro Thr Ser Ala Val Arg Ser Asn
                565                 570                 575 aga aaa ctc tct cac cgg cgc cta aaa gtg gac aaa cgg gat ttt ttg      1776
Arg Lys Leu Ser His Arg Arg Leu Lys Val Asp Lys Arg Asp Phe Leu
            580                 585                 590 aaa cga cct tac ggg aac ggg gat taa                                  1803
Lys Arg Pro Tyr Gly Asn Gly Asp
        595                 600

<210> SEQ ID NO 20
<211> LENGTH: 600
<212> TYPE: PRT
<213> ORGANISM: Arabidopsis thaliana

<400> SEQUENCE: 20

Met Ala Thr Thr Thr Thr Thr Thr Ala Arg Phe Ser Asp Ser Tyr
1               5                   10                  15

Glu Phe Ser Asn Thr Ser Gly Asn Ser Phe Ala Ala Glu Ser Ser
                20                  25                  30

Leu Asp Tyr Pro Thr Glu Phe Leu Thr Pro Pro Glu Val Ser Ala Leu
            35                  40                  45

Lys Leu Leu Ser Asn Cys Leu Glu Ser Val Phe Asp Ser Pro Glu Thr
        50                  55                  60

Phe Tyr Ser Asp Ala Lys Leu Val Leu Ala Gly Gly Arg Glu Val Ser
65                  70                  75                  80

Phe His Arg Cys Ile Leu Ser Ala Arg Ile Pro Val Phe Lys Ser Ala
```

-continued

```
                85                  90                  95
Leu Ala Thr Val Lys Glu Gln Lys Ser Ser Thr Val Lys Leu Gln
            100                 105                 110
Leu Lys Glu Ile Ala Arg Asp Tyr Glu Val Gly Phe Asp Ser Val Val
            115                 120                 125
Ala Val Leu Ala Tyr Val Tyr Ser Gly Arg Val Arg Ser Pro Pro Lys
130                 135                 140
Gly Ala Ser Ala Cys Val Asp Asp Cys Cys His Val Ala Cys Arg
145                 150                 155                 160
Ser Lys Val Asp Phe Met Val Glu Val Leu Tyr Leu Ser Phe Val Phe
                165                 170                 175
Gln Ile Gln Glu Leu Val Thr Leu Tyr Glu Arg Gln Phe Leu Glu Ile
            180                 185                 190
Val Asp Lys Val Val Glu Asp Ile Leu Val Ile Phe Lys Leu Asp
            195                 200                 205
Thr Leu Cys Gly Thr Thr Tyr Lys Lys Leu Leu Asp Arg Cys Ile Glu
    210                 215                 220
Ile Ile Val Lys Ser Asp Ile Glu Leu Val Ser Leu Glu Lys Ser Leu
225                 230                 235                 240
Pro Gln His Ile Phe Lys Gln Ile Ile Asp Ile Arg Glu Ala Leu Cys
                245                 250                 255
Leu Glu Pro Pro Lys Leu Glu Arg His Val Lys Asn Ile Tyr Lys Ala
            260                 265                 270
Leu Asp Ser Asp Asp Val Glu Leu Val Lys Met Leu Leu Glu Gly
            275                 280                 285
His Thr Asn Leu Asp Glu Ala Tyr Ala Leu His Phe Ala Ile Ala His
    290                 295                 300
Cys Ala Val Lys Thr Ala Tyr Asp Leu Leu Glu Leu Glu Leu Ala Asp
305                 310                 315                 320
Val Asn Leu Arg Asn Pro Arg Gly Tyr Thr Val Leu His Val Ala Ala
                325                 330                 335
Met Arg Lys Glu Pro Lys Leu Ile Ile Ser Leu Leu Met Lys Gly Ala
            340                 345                 350
Asn Ile Leu Asp Thr Thr Leu Asp Gly Arg Thr Ala Leu Val Ile Val
    355                 360                 365
Lys Arg Leu Thr Lys Ala Asp Asp Tyr Lys Thr Ser Thr Glu Asp Gly
    370                 375                 380
Thr Pro Ser Leu Lys Gly Gly Leu Cys Ile Glu Val Leu Glu His Glu
385                 390                 395                 400
Gln Lys Leu Glu Tyr Leu Ser Pro Ile Glu Ala Ser Leu Ser Leu Pro
                405                 410                 415
Val Thr Pro Glu Glu Leu Arg Met Arg Leu Leu Tyr Tyr Glu Asn Arg
            420                 425                 430
Val Ala Leu Ala Arg Leu Leu Phe Pro Val Glu Thr Glu Thr Val Gln
            435                 440                 445
Gly Ile Ala Lys Leu Glu Glu Thr Cys Glu Phe Thr Ala Ser Ser Leu
    450                 455                 460
Glu Pro Asp His His Ile Gly Glu Lys Arg Thr Ser Leu Asp Leu Asn
465                 470                 475                 480
Met Ala Pro Phe Gln Ile His Glu Lys His Leu Ser Arg Leu Arg Ala
                485                 490                 495
Leu Cys Lys Thr Val Glu Leu Gly Lys Arg Tyr Phe Lys Arg Cys Ser
            500                 505                 510
```

```
Leu Asp His Phe Met Asp Thr Glu Asp Leu Asn His Leu Ala Ser Val
        515                 520                 525

Glu Glu Asp Thr Pro Glu Lys Arg Leu Gln Lys Lys Gln Arg Tyr Met
530                 535                 540

Glu Leu Gln Glu Thr Leu Met Lys Thr Phe Ser Glu Asp Lys Glu Glu
545                 550                 555                 560

Cys Gly Lys Ser Ser Thr Pro Lys Pro Thr Ser Ala Val Arg Ser Asn
                565                 570                 575

Arg Lys Leu Ser His Arg Arg Leu Lys Val Asp Lys Arg Asp Phe Leu
            580                 585                 590

Lys Arg Pro Tyr Gly Asn Gly Asp
        595                 600

<210> SEQ ID NO 21
<211> LENGTH: 28
<212> TYPE: DNA
<213> ORGANISM: Artificial Sequence
<220> FEATURE:
<223> OTHER INFORMATION: Description of Artificial Sequence: PCR primer
      NIM1A

<400> SEQUENCE: 21
gakattattg tcaagtctaa tgtwgata                                          28

<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence: PCR primer
      NIM1B

<400> SEQUENCE: 22
aytkgaytck gatgatrttg artta                                             25

<210> SEQ ID NO 23
<211> LENGTH: 27
<212> TYPE: DNA
<213> ORGANISM: Artificial Sequence
<220> FEATURE:
<223> OTHER INFORMATION: Description of Artificial Sequence: PCR primer
      NIM1C

<400> SEQUENCE: 23
taaytcaaya tcatcmgart cmartgc                                           27

<210> SEQ ID NO 24
<211> LENGTH: 28
<212> TYPE: DNA
<213> ORGANISM: Artificial Sequence
<220> FEATURE:
<223> OTHER INFORMATION: Description of Artificial Sequence: PCR primer
      NIM1D
<220> FEATURE:
<221> NAME/KEY: misc_feature
<222> LOCATION: (1)..(28)
<223> OTHER INFORMATION: n = a, t, c or g

<400> SEQUENCE: 24
gttkagcmag nscaactcta ttttcaag                                          28

<210> SEQ ID NO 25
<211> LENGTH: 32
<212> TYPE: DNA
```

```
<213> ORGANISM: Artificial Sequence
<220> FEATURE:
<223> OTHER INFORMATION: Description of Artificial Sequence: PCR primer
      NIM2A

<400> SEQUENCE: 25
tgcatwgara twrttgtsaa gtctratgtw ga                                32

<210> SEQ ID NO 26
<211> LENGTH: 27
<212> TYPE: DNA
<213> ORGANISM: Artificial Sequence
<220> FEATURE:
<223> OTHER INFORMATION: Description of Artificial Sequence: PCR primer
      NIM2B

<400> SEQUENCE: 26
ggcaytggay tcwgatgatg ttgaryt                                      27

<210> SEQ ID NO 27
<211> LENGTH: 27
<212> TYPE: DNA
<213> ORGANISM: Artificial Sequence
<220> FEATURE:
<223> OTHER INFORMATION: Description of Artificial Sequence: PCR primer
      NIM2C

<400> SEQUENCE: 27
arytcaacat catcwgartc cartgcc                                      27

<210> SEQ ID NO 28
<211> LENGTH: 31
<212> TYPE: DNA
<213> ORGANISM: Artificial Sequence
<220> FEATURE:
<223> OTHER INFORMATION: Description of Artificial Sequence: PCR primer
      NIM2D

<400> SEQUENCE: 28
agttkagcma gdccaactck attttcaarr t                                 31

<210> SEQ ID NO 29
<211> LENGTH: 659
<212> TYPE: DNA
<213> ORGANISM: Nicotiana tabacum
<220> FEATURE:
<221> NAME/KEY: CDS
<222> LOCATION: (1)..(657)
<223> OTHER INFORMATION: Tobacco A

<400> SEQUENCE: 29 tgc atg gag att att gtc aag tct aat gtt gat atc ata acc ctt gat     48
Cys Met Glu Ile Ile Val Lys Ser Asn Val Asp Ile Ile Thr Leu Asp
 1               5                  10                  15 aag gcc ttg cct cat gac att gta aaa caa att acc gat tca cga gca     96
Lys Ala Leu Pro His Asp Ile Val Lys Gln Ile Thr Asp Ser Arg Ala
             20                  25                  30 gaa ctt ggt cta caa ggg cct gaa agc aat ggt ttt cct gat aaa cat    144
Glu Leu Gly Leu Gln Gly Pro Glu Ser Asn Gly Phe Pro Asp Lys His
         35                  40                  45 gtt aag agg ata cat agg gca tta gat tct gat gat gtt gaa tta ctg    192
Val Lys Arg Ile His Arg Ala Leu Asp Ser Asp Asp Val Glu Leu Leu
     50                  55                  60 cag atg ttg cta aga gag ggg cat act act cta gat gat gca tat gct    240
Gln Met Leu Leu Arg Glu Gly His Thr Thr Leu Asp Asp Ala Tyr Ala
 65                  70                  75                  80
```

```
ctc cac tat gct gta gca tat tgc gat gca aag act aca gca gaa ctt    288
Leu His Tyr Ala Val Ala Tyr Cys Asp Ala Lys Thr Thr Ala Glu Leu
                85                  90                  95 cta gat ctt gca ctt gct gat gtt aat cat caa aat tca aga gga tac    336
Leu Asp Leu Ala Leu Ala Asp Val Asn His Gln Asn Ser Arg Gly Tyr
            100                 105                 110 aca gtg ctg cat gtt gca gcc atg agg aaa gag cct aaa att ata gtg    384
Thr Val Leu His Val Ala Ala Met Arg Lys Glu Pro Lys Ile Ile Val
            115                 120                 125 tcc ctt tta acc aaa gga gct aga cct tct gat ctg aca tcc gat ggc    432
Ser Leu Leu Thr Lys Gly Ala Arg Pro Ser Asp Leu Thr Ser Asp Gly
        130                 135                 140 aga aaa gca ctt caa att gcc aag agg ctc act agg ctt gtg gat ttc    480
Arg Lys Ala Leu Gln Ile Ala Lys Arg Leu Thr Arg Leu Val Asp Phe
145                 150                 155                 160 agt aag tct cca gag gaa gga aaa tct gct tcg aag gat cgg tta tgc    528
Ser Lys Ser Pro Glu Glu Gly Lys Ser Ala Ser Lys Asp Arg Leu Cys
                165                 170                 175 att gag att ctg gag caa gca gaa aga aga gat cca ctg cta gga gaa    576
Ile Glu Ile Leu Glu Gln Ala Glu Arg Arg Asp Pro Leu Leu Gly Glu
            180                 185                 190 gct tct gta tct ctt gct atg gcg ggc gat gat ttg cgt atg aag ctg    624
Ala Ser Val Ser Leu Ala Met Ala Gly Asp Asp Leu Arg Met Lys Leu
            195                 200                 205 tta tac ctt gaa aat aga gtt ggc ctt gct caa ct                     659
Leu Tyr Leu Glu Asn Arg Val Gly Leu Ala Gln
        210                 215

<210> SEQ ID NO 30
<211> LENGTH: 219
<212> TYPE: PRT
<213> ORGANISM: Nicotiana tabacum

<400> SEQUENCE: 30

Cys Met Glu Ile Ile Val Lys Ser Asn Val Asp Ile Ile Thr Leu Asp
  1               5                  10                  15

Lys Ala Leu Pro His Asp Ile Val Lys Gln Ile Thr Asp Ser Arg Ala
                 20                  25                  30

Glu Leu Gly Leu Gln Gly Pro Glu Ser Asn Gly Phe Pro Asp Lys His
             35                  40                  45

Val Lys Arg Ile His Arg Ala Leu Asp Ser Asp Val Glu Leu Leu
     50                  55                  60

Gln Met Leu Leu Arg Glu Gly His Thr Thr Leu Asp Asp Ala Tyr Ala
 65                  70                  75                  80

Leu His Tyr Ala Val Ala Tyr Cys Asp Ala Lys Thr Thr Ala Glu Leu
                 85                  90                  95

Leu Asp Leu Ala Leu Ala Asp Val Asn His Gln Asn Ser Arg Gly Tyr
            100                 105                 110

Thr Val Leu His Val Ala Ala Met Arg Lys Glu Pro Lys Ile Ile Val
            115                 120                 125

Ser Leu Leu Thr Lys Gly Ala Arg Pro Ser Asp Leu Thr Ser Asp Gly
        130                 135                 140

Arg Lys Ala Leu Gln Ile Ala Lys Arg Leu Thr Arg Leu Val Asp Phe
145                 150                 155                 160

Ser Lys Ser Pro Glu Glu Gly Lys Ser Ala Ser Lys Asp Arg Leu Cys
                165                 170                 175

Ile Glu Ile Leu Glu Gln Ala Glu Arg Arg Asp Pro Leu Leu Gly Glu
```

```
                    180               185               190
Ala Ser Val Ser Leu Ala Met Ala Gly Asp Asp Leu Arg Met Lys Leu
            195               200               205
Leu Tyr Leu Glu Asn Arg Val Gly Leu Ala Gln
        210               215

<210> SEQ ID NO 31
<211> LENGTH: 498
<212> TYPE: DNA
<213> ORGANISM: Nicotiana tabacum
<220> FEATURE:
<221> NAME/KEY: CDS
<222> LOCATION: (2)..(496)
<223> OTHER INFORMATION: Tobacco B

<400> SEQUENCE: 31 g gca ctg gat tct gat gat gtt gag ctg gtc aag ctt cta ctc aac gag        49
  Ala Leu Asp Ser Asp Asp Val Glu Leu Val Lys Leu Leu Leu Asn Glu
      1               5                   10                  15 tct gag ata agc tta gat gaa gcc tac gct ctt cat tat gct gtt gca          97
Ser Glu Ile Ser Leu Asp Glu Ala Tyr Ala Leu His Tyr Ala Val Ala
                20                  25                  30 tat tgt gat ccc aag gtt gtg act gag gtt ctt gga ctg ggt gtt gct         145
Tyr Cys Asp Pro Lys Val Val Thr Glu Val Leu Gly Leu Gly Val Ala
        35                  40                  45 gat gtc aat cta cgt aat act cgc ggt tac act gtg ctt cac att gct         193
Asp Val Asn Leu Arg Asn Thr Arg Gly Tyr Thr Val Leu His Ile Ala
    50                  55                  60 gcc atg cgt aag gag cca gca ata att gta tcg ctt ttg act aag gga         241
Ala Met Arg Lys Glu Pro Ala Ile Ile Val Ser Leu Leu Thr Lys Gly
65                  70                  75                  80 gct cat gtg tca gag att aca ttg gat ggg caa agt gct gtt agt atc         289
Ala His Val Ser Glu Ile Thr Leu Asp Gly Gln Ser Ala Val Ser Ile
                85                  90                  95 tgt agg agg cta act agg cct aag gag tac cat gca aaa aca gaa caa         337
Cys Arg Arg Leu Thr Arg Pro Lys Glu Tyr His Ala Lys Thr Glu Gln
            100                 105                 110 ggc cag gaa gca aac aaa gat cgg gta tgt att gat gtt ttg gag aga         385
Gly Gln Glu Ala Asn Lys Asp Arg Val Cys Ile Asp Val Leu Glu Arg
        115                 120                 125 gag atg cgt cgc aac cca atg gct gga gat gca ttg ctt tct tcc caa         433
Glu Met Arg Arg Asn Pro Met Ala Gly Asp Ala Leu Leu Ser Ser Gln
    130                 135                 140 atg ttg gcc gat gat ctg cac atg aaa ctg cac tat ttt gaa aat cga         481
Met Leu Ala Asp Asp Leu His Met Lys Leu His Tyr Phe Glu Asn Arg
145                 150                 155                 160 gtt gga ctt gct caa ct                                                  498
Val Gly Leu Ala Gln
                165

<210> SEQ ID NO 32
<211> LENGTH: 165
<212> TYPE: PRT
<213> ORGANISM: Nicotiana tabacum

<400> SEQUENCE: 32

Ala Leu Asp Ser Asp Asp Val Glu Leu Val Lys Leu Leu Leu Asn Glu
  1               5                  10                  15

Ser Glu Ile Ser Leu Asp Glu Ala Tyr Ala Leu His Tyr Ala Val Ala
                20                  25                  30

Tyr Cys Asp Pro Lys Val Val Thr Glu Val Leu Gly Leu Gly Val Ala
```

```
                      35                  40                      45

Asp Val Asn Leu Arg Asn Thr Arg Gly Tyr Thr Val Leu His Ile Ala
             50                  55                  60

Ala Met Arg Lys Glu Pro Ala Ile Ile Val Ser Leu Leu Thr Lys Gly
 65                  70                  75                  80

Ala His Val Ser Glu Ile Thr Leu Asp Gly Gln Ser Ala Val Ser Ile
                     85                  90                  95

Cys Arg Arg Leu Thr Arg Pro Lys Glu Tyr His Ala Lys Thr Glu Gln
                 100                 105                 110

Gly Gln Glu Ala Asn Lys Asp Arg Val Cys Ile Asp Val Leu Glu Arg
             115                 120                 125

Glu Met Arg Arg Asn Pro Met Ala Gly Asp Ala Leu Leu Ser Ser Gln
 130                 135                 140

Met Leu Ala Asp Asp Leu His Met Lys Leu His Tyr Phe Glu Asn Arg
145                 150                 155                 160

Val Gly Leu Ala Gln
             165

<210> SEQ ID NO 33
<211> LENGTH: 498
<212> TYPE: DNA
<213> ORGANISM: Nicotiana tabacum
<220> FEATURE:
<221> NAME/KEY: CDS
<222> LOCATION: (2)..(496)
<223> OTHER INFORMATION: Tobacco C

<400> SEQUENCE: 33 g gca ctg gac tcw gat gat gtt gag ttt gtc aag ctt cta ctg agt gag        49
  Ala Leu Asp Xaa Asp Asp Val Glu Phe Val Lys Leu Leu Leu Ser Glu
    1               5                  10                  15 tct aac ata agc tta gat gaa gcc tac gct ctt cat tat gct gtg gca          97
Ser Asn Ile Ser Leu Asp Glu Ala Tyr Ala Leu His Tyr Ala Val Ala
             20                  25                  30 tat tgt gat ccc aag gtt gtg act gag gtt ctt gga ctg ggt gtt gcg        145
Tyr Cys Asp Pro Lys Val Val Thr Glu Val Leu Gly Leu Gly Val Ala
         35                  40                  45 gat gtc aac cta cgt aat act cgt ggt tac act gtg ctt cac att gct        193
Asp Val Asn Leu Arg Asn Thr Arg Gly Tyr Thr Val Leu His Ile Ala
     50                  55                  60 tcc atg cgt aag gag cca gca gta att gta tcg ctt ttg act aag gga        241
Ser Met Arg Lys Glu Pro Ala Val Ile Val Ser Leu Leu Thr Lys Gly
 65                  70                  75                  80 gct cgt gca tca gag act aca ttg gat ggg cag agt gct gtt agt atc        289
Ala Arg Ala Ser Glu Thr Thr Leu Asp Gly Gln Ser Ala Val Ser Ile
                 85                  90                  95 tgt agg agg ctg act agg cct aag gag tac cat gca aaa aca gaa caa        337
Cys Arg Arg Leu Thr Arg Pro Lys Glu Tyr His Ala Lys Thr Glu Gln
             100                 105                 110 ggc cag gaa gca aac aaa gat cgg gta tgt att gat gtt ttg gag aga        385
Gly Gln Glu Ala Asn Lys Asp Arg Val Cys Ile Asp Val Leu Glu Arg
         115                 120                 125 gag atg cgt cgc aac cca atg gct gga gat gca ttg ttt tct tcc cca        433
Glu Met Arg Arg Asn Pro Met Ala Gly Asp Ala Leu Phe Ser Ser Pro
 130                 135                 140 atg ttg gcc gat gat ctg cac atg aaa ctg cac tac ctt gaa aat aga        481
Met Leu Ala Asp Asp Leu His Met Lys Leu His Tyr Leu Glu Asn Arg
145                 150                 155                 160 gtt ggc ctg gct caa ct                                                  498
```

Val Gly Leu Ala Gln
165

<210> SEQ ID NO 34
<211> LENGTH: 165
<212> TYPE: PRT
<213> ORGANISM: Nicotiana tabacum

<400> SEQUENCE: 34

```
Ala Leu Asp Xaa Asp Val Glu Phe Val Lys Leu Leu Ser Glu
 1               5                  10                  15

Ser Asn Ile Ser Leu Asp Glu Ala Tyr Ala Leu His Tyr Ala Val Ala
                 20                  25                  30

Tyr Cys Asp Pro Lys Val Val Thr Glu Val Leu Gly Leu Gly Val Ala
             35                  40                  45

Asp Val Asn Leu Arg Asn Thr Arg Gly Tyr Thr Val Leu His Ile Ala
         50                  55                  60

Ser Met Arg Lys Glu Pro Ala Val Ile Val Ser Leu Leu Thr Lys Gly
 65                  70                  75                  80

Ala Arg Ala Ser Glu Thr Thr Leu Asp Gly Gln Ser Ala Val Ser Ile
                 85                  90                  95

Cys Arg Arg Leu Thr Arg Pro Lys Glu Tyr His Ala Lys Thr Glu Gln
            100                 105                 110

Gly Gln Glu Ala Asn Lys Asp Arg Val Cys Ile Asp Val Leu Glu Arg
        115                 120                 125

Glu Met Arg Arg Asn Pro Met Ala Gly Asp Ala Leu Phe Ser Ser Pro
    130                 135                 140

Met Leu Ala Asp Asp Leu His Met Lys Leu His Tyr Leu Glu Asn Arg
145                 150                 155                 160

Val Gly Leu Ala Gln
                165
```

<210> SEQ ID NO 35
<211> LENGTH: 399
<212> TYPE: DNA
<213> ORGANISM: Nicotiana tabacum
<220> FEATURE:
<221> NAME/KEY: CDS
<222> LOCATION: (1)..(399)
<223> OTHER INFORMATION: Tobacco D

<400> SEQUENCE: 35

```
act gat tcg gat gat gtt gag tta ctt aag tta ctt ctt gaa gag tct     48
Thr Asp Ser Asp Asp Val Glu Leu Leu Lys Leu Leu Leu Glu Glu Ser
 1               5                  10                  15 aat gtc act tta gac gat gct tgt gct ctt cat tat gca gct gct tat     96
Asn Val Thr Leu Asp Asp Ala Cys Ala Leu His Tyr Ala Ala Ala Tyr
                 20                  25                  30 tgt aac tcc aag gtt gtg aat gag gtc ctc gag ctg gat tta gct gat    144
Cys Asn Ser Lys Val Val Asn Glu Val Leu Glu Leu Asp Leu Ala Asp
             35                  40                  45 gtc aat ctt cag aac tcc cga gga tat aac gtc ctt cac gtt gct gct    192
Val Asn Leu Gln Asn Ser Arg Gly Tyr Asn Val Leu His Val Ala Ala
         50                  55                  60 aga aga aag gag cca tca ata ata atg gga cta ctt gaa aaa gga gca    240
Arg Arg Lys Glu Pro Ser Ile Ile Met Gly Leu Leu Glu Lys Gly Ala
 65                  70                  75                  80 tct ttc ttg aat act aca cgg gat gga aac aca gca cta tct atc tgt    288
Ser Phe Leu Asn Thr Thr Arg Asp Gly Asn Thr Ala Leu Ser Ile Cys
                 85                  90                  95
```

```
cgg aga ttg act cgg cca aag gat tat aat gag cca aca aag caa ggg      336
Arg Arg Leu Thr Arg Pro Lys Asp Tyr Asn Glu Pro Thr Lys Gln Gly
            100                 105                 110 aaa gaa act aat aag gac cgc ata tgc att gat att ttg gag aga gag      384
Lys Glu Thr Asn Lys Asp Arg Ile Cys Ile Asp Ile Leu Glu Arg Glu
        115                 120                 125 acg aat agg aat cct                                                   399
Thr Asn Arg Asn Pro
    130

<210> SEQ ID NO 36
<211> LENGTH: 133
<212> TYPE: PRT
<213> ORGANISM: Nicotiana tabacum

<400> SEQUENCE: 36

Thr Asp Ser Asp Asp Val Glu Leu Leu Lys Leu Leu Glu Glu Ser
 1               5                  10                  15

Asn Val Thr Leu Asp Asp Ala Cys Ala Leu His Tyr Ala Ala Tyr
            20                  25                  30

Cys Asn Ser Lys Val Val Asn Glu Val Leu Glu Leu Asp Leu Ala Asp
        35                  40                  45

Val Asn Leu Gln Asn Ser Arg Gly Tyr Asn Val Leu His Val Ala Ala
 50                  55                  60

Arg Arg Lys Glu Pro Ser Ile Ile Met Gly Leu Leu Glu Lys Gly Ala
65                   70                  75                  80

Ser Phe Leu Asn Thr Thr Arg Asp Gly Asn Thr Ala Leu Ser Ile Cys
            85                  90                  95

Arg Arg Leu Thr Arg Pro Lys Asp Tyr Asn Glu Pro Thr Lys Gln Gly
            100                 105                 110

Lys Glu Thr Asn Lys Asp Arg Ile Cys Ile Asp Ile Leu Glu Arg Glu
        115                 120                 125

Thr Asn Arg Asn Pro
    130

<210> SEQ ID NO 37
<211> LENGTH: 498
<212> TYPE: DNA
<213> ORGANISM: Lycopersicon esculentum
<220> FEATURE:
<221> NAME/KEY: CDS
<222> LOCATION: (2)..(496)
<223> OTHER INFORMATION: Tomato A

<400> SEQUENCE: 37 g gca ttg gat tct gat gat gtt gag tta cta agg atg ttg ctt aaa gag    49
  Ala Leu Asp Ser Asp Asp Val Glu Leu Leu Arg Met Leu Leu Lys Glu
   1               5                  10                  15 ggg cat act act ctt gat gat gca tat gct ctc cac tat gct gta gca      97
Gly His Thr Thr Leu Asp Asp Ala Tyr Ala Leu His Tyr Ala Val Ala
             20                  25                  30 tat tgc gat gca aag act aca gca gaa ctt tta gat ctt tca ctt gct     145
Tyr Cys Asp Ala Lys Thr Thr Ala Glu Leu Leu Asp Leu Ser Leu Ala
         35                  40                  45 gat gtt aat cat caa aat cct aga gga cac acg gta ctt cat gtt gct     193
Asp Val Asn His Gln Asn Pro Arg Gly His Thr Val Leu His Val Ala
 50                  55                  60 gcc atg agg aaa gaa cct aaa att ata gtg tcc ctt tta acc aaa gga     241
Ala Met Arg Lys Glu Pro Lys Ile Ile Val Ser Leu Leu Thr Lys Gly
65                   70                  75                  80
```

```
gct aga cct tct gat ctg aca tcc gat ggc aaa aaa gca ctt caa att        289
Ala Arg Pro Ser Asp Leu Thr Ser Asp Gly Lys Lys Ala Leu Gln Ile
            85                  90                  95 gct aag agg ctc act agg ctt gta gat ttt acc aag tct aca gag gaa        337
Ala Lys Arg Leu Thr Arg Leu Val Asp Phe Thr Lys Ser Thr Glu Glu
            100                 105                 110 gga aaa tct gct cca aag gat cgg tta tgc att gag att ctg gag caa        385
Gly Lys Ser Ala Pro Lys Asp Arg Leu Cys Ile Glu Ile Leu Glu Gln
        115                 120                 125 gca gaa aga aga gat cca cta cta gga gaa gct tca tta tct ctt gct        433
Ala Glu Arg Arg Asp Pro Leu Leu Gly Glu Ala Ser Leu Ser Leu Ala
    130                 135                 140 atg gca ggc gat gat ttg cgt atg aag ctg tta tac ctt gaa aat aga        481
Met Ala Gly Asp Asp Leu Arg Met Lys Leu Leu Tyr Leu Glu Asn Arg
145                 150                 155                 160 gtt ggc ctt gct aaa ct                                                 498
Val Gly Leu Ala Lys
                165

<210> SEQ ID NO 38
<211> LENGTH: 165
<212> TYPE: PRT
<213> ORGANISM: Lycopersicon esculentum

<400> SEQUENCE: 38

Ala Leu Asp Ser Asp Val Glu Leu Arg Met Leu Leu Lys Glu
1               5                   10                  15

Gly His Thr Thr Leu Asp Asp Ala Tyr Ala Leu His Tyr Ala Val Ala
                20                  25                  30

Tyr Cys Asp Ala Lys Thr Thr Ala Glu Leu Leu Asp Leu Ser Leu Ala
            35                  40                  45

Asp Val Asn His Gln Asn Pro Arg Gly His Thr Val Leu His Val Ala
        50                  55                  60

Ala Met Arg Lys Glu Pro Lys Ile Ile Val Ser Leu Leu Thr Lys Gly
65                  70                  75                  80

Ala Arg Pro Ser Asp Leu Thr Ser Asp Gly Lys Lys Ala Leu Gln Ile
                85                  90                  95

Ala Lys Arg Leu Thr Arg Leu Val Asp Phe Thr Lys Ser Thr Glu Glu
            100                 105                 110

Gly Lys Ser Ala Pro Lys Asp Arg Leu Cys Ile Glu Ile Leu Glu Gln
        115                 120                 125

Ala Glu Arg Arg Asp Pro Leu Leu Gly Glu Ala Ser Leu Ser Leu Ala
    130                 135                 140

Met Ala Gly Asp Asp Leu Arg Met Lys Leu Leu Tyr Leu Glu Asn Arg
145                 150                 155                 160

Val Gly Leu Ala Lys
                165

<210> SEQ ID NO 39
<211> LENGTH: 498
<212> TYPE: DNA
<213> ORGANISM: Beta vulgaris
<220> FEATURE:
<221> NAME/KEY: CDS
<222> LOCATION: (2)..(496)
<223> OTHER INFORMATION: Sugarbeet

<400> SEQUENCE: 39 g gca ttg gat tct gat gat gtt gag tta gtc aga atg ctt tta aaa gag     49
```

```
Ala Leu Asp Ser Asp Val Glu Leu Val Arg Met Leu Leu Lys Glu
 1               5                  10                  15 cgc cat aca act cta gat gat gca tat gcc ctt cac tat gct gtg gca    97
Arg His Thr Thr Leu Asp Asp Ala Tyr Ala Leu His Tyr Ala Val Ala
             20                  25                  30 cat tgt gat gcc aag acc acc acg gag ctt ctt gag ctt ggg ctt gca   145
His Cys Asp Ala Lys Thr Thr Thr Glu Leu Leu Glu Leu Gly Leu Ala
         35                  40                  45 gat gtt aat ctt aga aat cta agg ggt cac act gtg cta cat gtg gca   193
Asp Val Asn Leu Arg Asn Leu Arg Gly His Thr Val Leu His Val Ala
     50                  55                  60 gcc atg aga aaa gag cct aag ata att gta tcc ttg tta acc aag gga   241
Ala Met Arg Lys Glu Pro Lys Ile Ile Val Ser Leu Leu Thr Lys Gly
 65                  70                  75                  80 gcc cat ccg tct gat ata aca tca gat gat aaa aaa gca ctg cag ata   289
Ala His Pro Ser Asp Ile Thr Ser Asp Asp Lys Lys Ala Leu Gln Ile
                 85                  90                  95 gca aag aga cta aca aaa gct gtg gac ttc tat aaa act aca gaa caa   337
Ala Lys Arg Leu Thr Lys Ala Val Asp Phe Tyr Lys Thr Thr Glu Gln
            100                 105                 110 gga aaa gat gca cca aag gat cgg ttg tgc att gaa ata ctg gag caa   385
Gly Lys Asp Ala Pro Lys Asp Arg Leu Cys Ile Glu Ile Leu Glu Gln
        115                 120                 125 gct gaa aga aga gaa cca ttg cta gga gaa ggt tct gtt tct ctt gca   433
Ala Glu Arg Arg Glu Pro Leu Leu Gly Glu Gly Ser Val Ser Leu Ala
    130                 135                 140 aag gca gga gat gat ctg cgt atg aag cta tta tac ctt gaa aat cga   481
Lys Ala Gly Asp Asp Leu Arg Met Lys Leu Leu Tyr Leu Glu Asn Arg
145                 150                 155                 160 gtt ggc ctt gct caa ct                                            498
Val Gly Leu Ala Gln
                165

<210> SEQ ID NO 40
<211> LENGTH: 165
<212> TYPE: PRT
<213> ORGANISM: Beta vulgaris

<400> SEQUENCE: 40

Ala Leu Asp Ser Asp Val Glu Leu Val Arg Met Leu Leu Lys Glu
 1               5                  10                  15

Arg His Thr Thr Leu Asp Asp Ala Tyr Ala Leu His Tyr Ala Val Ala
             20                  25                  30

His Cys Asp Ala Lys Thr Thr Thr Glu Leu Leu Glu Leu Gly Leu Ala
         35                  40                  45

Asp Val Asn Leu Arg Asn Leu Arg Gly His Thr Val Leu His Val Ala
     50                  55                  60

Ala Met Arg Lys Glu Pro Lys Ile Ile Val Ser Leu Leu Thr Lys Gly
 65                  70                  75                  80

Ala His Pro Ser Asp Ile Thr Ser Asp Asp Lys Lys Ala Leu Gln Ile
                 85                  90                  95

Ala Lys Arg Leu Thr Lys Ala Val Asp Phe Tyr Lys Thr Thr Glu Gln
            100                 105                 110

Gly Lys Asp Ala Pro Lys Asp Arg Leu Cys Ile Glu Ile Leu Glu Gln
        115                 120                 125

Ala Glu Arg Arg Glu Pro Leu Leu Gly Glu Gly Ser Val Ser Leu Ala
    130                 135                 140

Lys Ala Gly Asp Asp Leu Arg Met Lys Leu Leu Tyr Leu Glu Asn Arg
```

```
                145                 150                 155                 160
Val Gly Leu Ala Gln
                165

<210> SEQ ID NO 41
<211> LENGTH: 498
<212> TYPE: DNA
<213> ORGANISM: Helianthus annuus
<220> FEATURE:
<221> NAME/KEY: CDS
<222> LOCATION: (2)..(496)
<223> OTHER INFORMATION: Sunflower A

<400> SEQUENCE: 41 g gca ttg gat tct gat gat gtt gag yta gtc aca atg tta tta cga gaa      49
  Ala Leu Asp Ser Asp Asp Val Glu Xaa Val Thr Met Leu Leu Arg Glu
   1               5                  10                  15 ggt cat act tca tta gac ggt tct tgc gct ctt cat tac gct gtt gcg        97
Gly His Thr Ser Leu Asp Gly Ser Cys Ala Leu His Tyr Ala Val Ala
                20                  25                  30 tac gca gat gct aaa acg aca acc gaa tta ctg gat tta gca ctt gct       145
Tyr Ala Asp Ala Lys Thr Thr Thr Glu Leu Leu Asp Leu Ala Leu Ala
            35                  40                  45 gac gta aat cat aaa aac tcg agg ggt ttt acc gta ctt cat gtt gcc       193
Asp Val Asn His Lys Asn Ser Arg Gly Phe Thr Val Leu His Val Ala
        50                  55                  60 gct atg aga aaa gag ccg agt att atc gtt tcg ctt ctt acg aaa ggg       241
Ala Met Arg Lys Glu Pro Ser Ile Ile Val Ser Leu Leu Thr Lys Gly
 65                  70                  75                  80 gcc cga ccc tcg gat ctc acc cct gat ggg aga aaa gca cta cag att       289
Ala Arg Pro Ser Asp Leu Thr Pro Asp Gly Arg Lys Ala Leu Gln Ile
                85                  90                  95 tcg aag agg ttg acc aga gcg gtt gac tat tac aag tca aac gag gat       337
Ser Lys Arg Leu Thr Arg Ala Val Asp Tyr Tyr Lys Ser Asn Glu Asp
            100                 105                 110 gat aaa gag tca acg aaa ggt cgt ttg tgt att gag ata ttg gaa caa       385
Asp Lys Glu Ser Thr Lys Gly Arg Leu Cys Ile Glu Ile Leu Glu Gln
        115                 120                 125 gcc gaa aga aga aat cca ttg tta ggt gaa gct tcg gct tct ctt gca       433
Ala Glu Arg Arg Asn Pro Leu Leu Gly Glu Ala Ser Ala Ser Leu Ala
130                 135                 140 atg gcc gga gat gat ttg cgt gga aag ttg ttg tac ctt gaa aat cga       481
Met Ala Gly Asp Asp Leu Arg Gly Lys Leu Leu Tyr Leu Glu Asn Arg
145                 150                 155                 160 gtt ggc ctg gct caa ct                                                498
Val Gly Leu Ala Gln
                165

<210> SEQ ID NO 42
<211> LENGTH: 165
<212> TYPE: PRT
<213> ORGANISM: Helianthus annuus

<400> SEQUENCE: 42

Ala Leu Asp Ser Asp Asp Val Glu Xaa Val Thr Met Leu Leu Arg Glu
 1               5                  10                  15

Gly His Thr Ser Leu Asp Gly Ser Cys Ala Leu His Tyr Ala Val Ala
                20                  25                  30

Tyr Ala Asp Ala Lys Thr Thr Thr Glu Leu Leu Asp Leu Ala Leu Ala
            35                  40                  45

Asp Val Asn His Lys Asn Ser Arg Gly Phe Thr Val Leu His Val Ala
```

```
                        50                   55                    60
Ala Met Arg Lys Glu Pro Ser Ile Ile Val Ser Leu Leu Thr Lys Gly
 65                   70                   75                    80

Ala Arg Pro Ser Asp Leu Thr Pro Asp Gly Arg Lys Ala Leu Gln Ile
                    85                   90                    95

Ser Lys Arg Leu Thr Arg Ala Val Asp Tyr Tyr Lys Ser Asn Glu Asp
                  100                  105                  110

Asp Lys Glu Ser Thr Lys Gly Arg Leu Cys Ile Glu Ile Leu Glu Gln
              115                  120                  125

Ala Glu Arg Arg Asn Pro Leu Leu Gly Glu Ala Ser Ala Ser Leu Ala
          130                  135                  140

Met Ala Gly Asp Asp Leu Arg Gly Lys Leu Leu Tyr Leu Glu Asn Arg
145                  150                  155                  160

Val Gly Leu Ala Gln
              165

<210> SEQ ID NO 43
<211> LENGTH: 498
<212> TYPE: DNA
<213> ORGANISM: Helianthus annuus
<220> FEATURE:
<221> NAME/KEY: CDS
<222> LOCATION: (2)..(496)
<223> OTHER INFORMATION: Sunflower B

<400> SEQUENCE: 43 g gca ttg gac tct gat gat gtt gag ctt gtg aaa atg att tta gac gaa        49
  Ala Leu Asp Ser Asp Asp Val Glu Leu Val Lys Met Ile Leu Asp Glu
    1               5                  10                  15 tcc aaa atc acg tta gat gaa gcc tgc gct ctt cat tat gcg gtc atg          97
Ser Lys Ile Thr Leu Asp Glu Ala Cys Ala Leu His Tyr Ala Val Met
              20                  25                  30 tat tgt aat caa gaa gtt gct aag gag att ctt aac tta aac cgt gcg         145
Tyr Cys Asn Gln Glu Val Ala Lys Glu Ile Leu Asn Leu Asn Arg Ala
          35                  40                  45 gat gtt aat ctt aga aac tca cga gat tac acc gtg ctt cat gtt gct         193
Asp Val Asn Leu Arg Asn Ser Arg Asp Tyr Thr Val Leu His Val Ala
      50                  55                  60 gcc atg cgt aaa gaa cca tca ctt att gtt tcg att cta agc aaa ggc         241
Ala Met Arg Lys Glu Pro Ser Leu Ile Val Ser Ile Leu Ser Lys Gly
 65                  70                  75                  80 gcg tgt gca tcg gat act act ttt gat gga caa agt gcg gtt agt att         289
Ala Cys Ala Ser Asp Thr Thr Phe Asp Gly Gln Ser Ala Val Ser Ile
                    85                  90                  95 tgc agg aga cga aca agg ccc aag gat tat tat gtg aaa acc gaa cac         337
Cys Arg Arg Arg Thr Arg Pro Lys Asp Tyr Tyr Val Lys Thr Glu His
                100                  105                  110 ggg caa gaa aca aat aaa gat cgt ata tgc atc gat gtt ttg gag cgg         385
Gly Gln Glu Thr Asn Lys Asp Arg Ile Cys Ile Asp Val Leu Glu Arg
              115                  120                  125 gaa ata aag agg aat ccg atg ata ggc gat gtt tcc gtg tgt tct tca         433
Glu Ile Lys Arg Asn Pro Met Ile Gly Asp Val Ser Val Cys Ser Ser
          130                  135                  140 gca gtg gct gat gat ttg cat atg aat tta ctc tac ttt gaa aat cga         481
Ala Val Ala Asp Asp Leu His Met Asn Leu Leu Tyr Phe Glu Asn Arg
145                  150                  155                  160 gtt ggc ctt gct caa ct                                                    498
Val Gly Leu Ala Gln
              165
```

```
<210> SEQ ID NO 44
<211> LENGTH: 165
<212> TYPE: PRT
<213> ORGANISM: Helianthus annuus

<400> SEQUENCE: 44

Ala Leu Asp Ser Asp Asp Val Glu Leu Val Lys Met Ile Leu Asp Glu
  1               5                  10                  15

Ser Lys Ile Thr Leu Asp Glu Ala Cys Ala Leu His Tyr Ala Val Met
                 20                  25                  30

Tyr Cys Asn Gln Glu Val Ala Lys Glu Ile Leu Asn Leu Asn Arg Ala
             35                  40                  45

Asp Val Asn Leu Arg Asn Ser Arg Asp Tyr Thr Val Leu His Val Ala
         50                  55                  60

Ala Met Arg Lys Glu Pro Ser Leu Ile Val Ser Ile Leu Ser Lys Gly
 65                  70                  75                  80

Ala Cys Ala Ser Asp Thr Thr Phe Asp Gly Gln Ser Ala Val Ser Ile
                 85                  90                  95

Cys Arg Arg Arg Thr Arg Pro Lys Asp Tyr Tyr Val Lys Thr Glu His
            100                 105                 110

Gly Gln Glu Thr Asn Lys Asp Arg Ile Cys Ile Asp Val Leu Glu Arg
        115                 120                 125

Glu Ile Lys Arg Asn Pro Met Ile Gly Asp Val Ser Val Cys Ser Ser
130                 135                 140

Ala Val Ala Asp Asp Leu His Met Asn Leu Leu Tyr Phe Glu Asn Arg
145                 150                 155                 160

Val Gly Leu Ala Gln
                165

<210> SEQ ID NO 45
<211> LENGTH: 653
<212> TYPE: DNA
<213> ORGANISM: Solanum tuberosum
<220> FEATURE:
<221> NAME/KEY: CDS
<222> LOCATION: (1)..(651)
<223> OTHER INFORMATION: Potato A

<400> SEQUENCE: 45 gak att att gtc aag tct aat gtt gat atc ata acc ctt gat aag tcc      48
Xaa Ile Ile Val Lys Ser Asn Val Asp Ile Ile Thr Leu Asp Lys Ser
  1               5                  10                  15 ttg cct cat gac atc gta aaa caa atc act gat tca cgt gct gaa ctt     96
Leu Pro His Asp Ile Val Lys Gln Ile Thr Asp Ser Arg Ala Glu Leu
                 20                  25                  30 ggt cta caa ggg cct gaa agc aat ggt ttt cct gat aaa cat gtt aag    144
Gly Leu Gln Gly Pro Glu Ser Asn Gly Phe Pro Asp Lys His Val Lys
             35                  40                  45 agg ata cat agg gca ttg gac tct gat gat gtt gag tta cta agg atg    192
Arg Ile His Arg Ala Leu Asp Ser Asp Asp Val Glu Leu Leu Arg Met
         50                  55                  60 ttg ctt aaa gaa ggg cat act act ctc gat gat gca tat gct ctc cac    240
Leu Leu Lys Glu Gly His Thr Thr Leu Asp Asp Ala Tyr Ala Leu His
 65                  70                  75                  80 tat gct gta gca tat tgc gat gca aag act aca gca gaa ctt tta gat    288
Tyr Ala Val Ala Tyr Cys Asp Ala Lys Thr Thr Ala Glu Leu Leu Asp
                 85                  90                  95 ctt tca ctt gct gat gtt aat cat caa aat cct aga gga tac acg gta    336
Leu Ser Leu Ala Asp Val Asn His Gln Asn Pro Arg Gly Tyr Thr Val
```

| | | | | | | | | | | | | | | | | |
|---|---|---|---|---|---|---|---|---|---|---|---|---|---|---|---|---|
| | | | | 100 | | | | | 105 | | | | | 110 | | |
| ctt | cat | gtt | gct | gcc | atg | agg | aaa | gag | cct | aaa | att | ata | gtg | tcc | ctt | 384 |
| Leu | His | Val | Ala | Ala | Met | Arg | Lys | Glu | Pro | Lys | Ile | Ile | Val | Ser | Leu | |
| | | 115 | | | | | 120 | | | | | 125 | | | | |
| tta | acc | aaa | gga | gct | aga | cct | tct | gat | ctg | aca | tct | gat | ggc | aaa | aaa | 432 |
| Leu | Thr | Lys | Gly | Ala | Arg | Pro | Ser | Asp | Leu | Thr | Ser | Asp | Gly | Lys | Lys | |
| | 130 | | | | | 135 | | | | | 140 | | | | | |
| gca | ctt | caa | att | gct | aag | agg | ctc | act | agg | ctt | gtg | gat | ttt | act | aag | 480 |
| Ala | Leu | Gln | Ile | Ala | Lys | Arg | Leu | Thr | Arg | Leu | Val | Asp | Phe | Thr | Lys | |
| 145 | | | | | 150 | | | | | 155 | | | | | 160 | |
| tct | aca | gag | gaa | gga | aaa | tct | gct | cca | aaa | gat | cgg | tta | tgc | att | gag | 528 |
| Ser | Thr | Glu | Glu | Gly | Lys | Ser | Ala | Pro | Lys | Asp | Arg | Leu | Cys | Ile | Glu | |
| | | | | 165 | | | | | 170 | | | | | 175 | | |
| att | ctg | gag | caa | gca | gaa | aga | aga | gat | cca | cta | cta | gga | gaa | gct | tca | 576 |
| Ile | Leu | Glu | Gln | Ala | Glu | Arg | Arg | Asp | Pro | Leu | Leu | Gly | Glu | Ala | Ser | |
| | | | 180 | | | | | 185 | | | | | 190 | | | |
| tta | tct | ctt | gct | atg | gca | ggc | gat | gat | ttg | cgt | atg | aag | ctg | tta | tac | 624 |
| Leu | Ser | Leu | Ala | Met | Ala | Gly | Asp | Asp | Leu | Arg | Met | Lys | Leu | Leu | Tyr | |
| | | 195 | | | | | 200 | | | | | 205 | | | | |
| ctt | gaa | aat | cga | gtt | ggc | ctk | gct | caa | ct | | | | | | | 653 |
| Leu | Glu | Asn | Arg | Val | Gly | Xaa | Ala | Gln | | | | | | | | |
| | 210 | | | | | 215 | | | | | | | | | | |

<210> SEQ ID NO 46
<211> LENGTH: 217
<212> TYPE: PRT
<213> ORGANISM: Solanum tuberosum

<400> SEQUENCE: 46

Xaa Ile Ile Val Lys Ser Asn Val Asp Ile Ile Thr Leu Asp Lys Ser
 1               5                   10                  15

Leu Pro His Asp Ile Val Lys Gln Ile Thr Asp Ser Arg Ala Glu Leu
             20                  25                  30

Gly Leu Gln Gly Pro Glu Ser Asn Gly Phe Pro Asp Lys His Val Lys
         35                  40                  45

Arg Ile His Arg Ala Leu Asp Ser Asp Val Glu Leu Leu Arg Met
     50                  55                  60

Leu Leu Lys Glu Gly His Thr Thr Leu Asp Asp Ala Tyr Ala Leu His
 65                  70                  75                  80

Tyr Ala Val Ala Tyr Cys Asp Ala Lys Thr Thr Ala Glu Leu Leu Asp
                 85                  90                  95

Leu Ser Leu Ala Asp Val Asn His Gln Asn Pro Arg Gly Tyr Thr Val
             100                 105                 110

Leu His Val Ala Ala Met Arg Lys Glu Pro Lys Ile Ile Val Ser Leu
         115                 120                 125

Leu Thr Lys Gly Ala Arg Pro Ser Asp Leu Thr Ser Asp Gly Lys Lys
     130                 135                 140

Ala Leu Gln Ile Ala Lys Arg Leu Thr Arg Leu Val Asp Phe Thr Lys
145                 150                 155                 160

Ser Thr Glu Glu Gly Lys Ser Ala Pro Lys Asp Arg Leu Cys Ile Glu
                 165                 170                 175

Ile Leu Glu Gln Ala Glu Arg Arg Asp Pro Leu Leu Gly Glu Ala Ser
             180                 185                 190

Leu Ser Leu Ala Met Ala Gly Asp Asp Leu Arg Met Lys Leu Leu Tyr
         195                 200                 205

Leu Glu Asn Arg Val Gly Xaa Ala Gln
     210                 215

```
<210> SEQ ID NO 47
<211> LENGTH: 498
<212> TYPE: DNA
<213> ORGANISM: Solanum tuberosum
<220> FEATURE:
<221> NAME/KEY: CDS
<222> LOCATION: (2)..(496)
<223> OTHER INFORMATION: Potato B

<400> SEQUENCE: 47 g gca ttg gat tca gat gat gtt gag ttt gtc aag ctt cta ctt aat gag       49
  Ala Leu Asp Ser Asp Asp Val Glu Phe Val Lys Leu Leu Leu Asn Glu
   1               5                  10                  15 tct gac ata agt tta gat gga gcc tac gct ctt cat tac gct gtt gca         97
Ser Asp Ile Ser Leu Asp Gly Ala Tyr Ala Leu His Tyr Ala Val Ala
             20                  25                  30 tat tgt gac ccc aag gtt gtt act gag gtt ctt gga ctg ggt gtt gca        145
Tyr Cys Asp Pro Lys Val Val Thr Glu Val Leu Gly Leu Gly Val Ala
         35                  40                  45 aat gtc aac ctt cgg aat aca cgt ggt tac act gtg ctt cac att gct        193
Asn Val Asn Leu Arg Asn Thr Arg Gly Tyr Thr Val Leu His Ile Ala
 50                  55                  60 gcc atg cgt aag gaa ccc tca atc att gta tca ctt ttg act aag gga        241
Ala Met Arg Lys Glu Pro Ser Ile Ile Val Ser Leu Leu Thr Lys Gly
 65                  70                  75                  80 gct cat gca tca gaa att aca ttg gat ggg cag agt gct gtt ggc atc        289
Ala His Ala Ser Glu Ile Thr Leu Asp Gly Gln Ser Ala Val Gly Ile
                 85                  90                  95 tgt agg agg ctg agt agg cct aag gag tac cat gca aaa aca gaa caa        337
Cys Arg Arg Leu Ser Arg Pro Lys Glu Tyr His Ala Lys Thr Glu Gln
            100                 105                 110 ggc cag gaa gca aac aaa gat cgg gta tgt att gat gtt ttg gag aga        385
Gly Gln Glu Ala Asn Lys Asp Arg Val Cys Ile Asp Val Leu Glu Arg
        115                 120                 125 gag atg cgt cac aac cca atg acc gga gat gca tta ttt tct tcc ccc        433
Glu Met Arg His Asn Pro Met Thr Gly Asp Ala Leu Phe Ser Ser Pro
    130                 135                 140 atg ttg gcc gat gat ctg ccc atg aaa ctg ctc tac ctt gaa aat cga        481
Met Leu Ala Asp Asp Leu Pro Met Lys Leu Leu Tyr Leu Glu Asn Arg
145                 150                 155                 160 gtt ggc ctt gct aaa ct                                                 498
Val Gly Leu Ala Lys
                165

<210> SEQ ID NO 48
<211> LENGTH: 165
<212> TYPE: PRT
<213> ORGANISM: Solanum tuberosum

<400> SEQUENCE: 48

Ala Leu Asp Ser Asp Asp Val Glu Phe Val Lys Leu Leu Leu Asn Glu
 1               5                  10                  15

Ser Asp Ile Ser Leu Asp Gly Ala Tyr Ala Leu His Tyr Ala Val Ala
             20                  25                  30

Tyr Cys Asp Pro Lys Val Val Thr Glu Val Leu Gly Leu Gly Val Ala
         35                  40                  45

Asn Val Asn Leu Arg Asn Thr Arg Gly Tyr Thr Val Leu His Ile Ala
 50                  55                  60

Ala Met Arg Lys Glu Pro Ser Ile Ile Val Ser Leu Leu Thr Lys Gly
 65                  70                  75                  80
```

```
Ala His Ala Ser Glu Ile Thr Leu Asp Gly Gln Ser Ala Val Gly Ile
                85                  90                  95

Cys Arg Arg Leu Ser Arg Pro Lys Glu Tyr His Ala Lys Thr Glu Gln
            100                 105                 110

Gly Gln Glu Ala Asn Lys Asp Arg Val Cys Ile Asp Val Leu Glu Arg
        115                 120                 125

Glu Met Arg His Asn Pro Met Thr Gly Asp Ala Leu Phe Ser Ser Pro
    130                 135                 140

Met Leu Ala Asp Asp Leu Pro Met Lys Leu Leu Tyr Leu Glu Asn Arg
145                 150                 155                 160

Val Gly Leu Ala Lys
                165

<210> SEQ ID NO 49
<211> LENGTH: 477
<212> TYPE: DNA
<213> ORGANISM: Solanum tuberosum
<220> FEATURE:
<221> NAME/KEY: CDS
<222> LOCATION: (2)..(475)
<223> OTHER INFORMATION: Potato C

<400> SEQUENCE: 49 g gca ctg gac tct gat gat gtt gag ttt gtc aag ctt cta ctt aat gag      49
  Ala Leu Asp Ser Asp Asp Val Glu Phe Val Lys Leu Leu Leu Asn Glu
   1               5                  10                  15 tct gac ata agt tta gat gga gcc tac gct ctt cat tac gct gtt gca        97
Ser Asp Ile Ser Leu Asp Gly Ala Tyr Ala Leu His Tyr Ala Val Ala
             20                  25                  30 tat tgt gac ccc aag gtt gtt act gag gtt ctt gga ctg ggt gtt gct       145
Tyr Cys Asp Pro Lys Val Val Thr Glu Val Leu Gly Leu Gly Val Ala
         35                  40                  45 aat gtc aac ctt cgg aat aca cgt ggt tac act gtg ctt cac att gct       193
Asn Val Asn Leu Arg Asn Thr Arg Gly Tyr Thr Val Leu His Ile Ala
     50                  55                  60 gcc atg cgt aag gaa ccc tca atc att gta tca ctt ttg act aag gga       241
Ala Met Arg Lys Glu Pro Ser Ile Ile Val Ser Leu Leu Thr Lys Gly
 65                  70                  75                  80 gct cat gca tca gaa att aca ttg gat ggg cag agt gct gtt agc atc       289
Ala His Ala Ser Glu Ile Thr Leu Asp Gly Gln Ser Ala Val Ser Ile
                 85                  90                  95 tgt agg agg ctg act agg cct aag gag tac cat gca aaa aca gaa caa       337
Cys Arg Arg Leu Thr Arg Pro Lys Glu Tyr His Ala Lys Thr Glu Gln
            100                 105                 110 ggc cag gaa gca aac aaa gat cgg gta tgt att gat gtt ttg gag aga       385
Gly Gln Glu Ala Asn Lys Asp Arg Val Cys Ile Asp Val Leu Glu Arg
        115                 120                 125 gag atg cgt cgc aac cca atg acc gga gat gca tta ttt tct tcc ccc       433
Glu Met Arg Arg Asn Pro Met Thr Gly Asp Ala Leu Phe Ser Ser Pro
    130                 135                 140 atg aaa cag ctc tac ctt gaa aat aga gtt ggc ctt gct aaa ct            477
Met Lys Gln Leu Tyr Leu Glu Asn Arg Val Gly Leu Ala Lys
145                 150                 155

<210> SEQ ID NO 50
<211> LENGTH: 158
<212> TYPE: PRT
<213> ORGANISM: Solanum tuberosum

<400> SEQUENCE: 50
```

```
Ala Leu Asp Ser Asp Asp Val Glu Phe Val Lys Leu Leu Asn Glu
  1               5                  10                  15

Ser Asp Ile Ser Leu Asp Gly Ala Tyr Ala Leu His Tyr Ala Val Ala
             20                  25                  30

Tyr Cys Asp Pro Lys Val Val Thr Glu Val Leu Gly Leu Gly Val Ala
         35                  40                  45

Asn Val Asn Leu Arg Asn Thr Arg Gly Tyr Thr Val Leu His Ile Ala
     50                  55                  60

Ala Met Arg Lys Glu Pro Ser Ile Ile Val Ser Leu Leu Thr Lys Gly
 65                  70                  75                  80

Ala His Ala Ser Glu Ile Thr Leu Asp Gly Gln Ser Ala Val Ser Ile
                 85                  90                  95

Cys Arg Arg Leu Thr Arg Pro Lys Glu Tyr His Ala Lys Thr Glu Gln
                100                 105                 110

Gly Gln Glu Ala Asn Lys Asp Arg Val Cys Ile Asp Val Leu Glu Arg
            115                 120                 125

Glu Met Arg Arg Asn Pro Met Thr Gly Asp Ala Leu Phe Ser Ser Pro
130                 135                 140

Met Lys Gln Leu Tyr Leu Glu Asn Arg Val Gly Leu Ala Lys
145                 150                 155
```

<210> SEQ ID NO 51
<211> LENGTH: 501
<212> TYPE: DNA
<213> ORGANISM: Brassica napus
<220> FEATURE:
<221> NAME/KEY: CDS
<222> LOCATION: (2)..(499)
<223> OTHER INFORMATION: Canola A

<400> SEQUENCE: 51

```
g gca ttg gat tct gat gat gtt gag ttt gtg aag ttg ctt ttg act gag      49
  Ala Leu Asp Ser Asp Asp Val Glu Phe Val Lys Leu Leu Leu Thr Glu
    1               5                  10                  15 tca gat atc act cta gat gaa gcc aat ggt ctt cat tac tca gtg gtg       97
Ser Asp Ile Thr Leu Asp Glu Ala Asn Gly Leu His Tyr Ser Val Val
             20                  25                  30 tat agt gat ccc aaa gtt gtt gcc gag att ctt act ctt gat atg ggt      145
Tyr Ser Asp Pro Lys Val Val Ala Glu Ile Leu Thr Leu Asp Met Gly
         35                  40                  45 gat gtc aac cac aga aac tca cgt ggc tac acg gtt ctt cat ctc gca      193
Asp Val Asn His Arg Asn Ser Arg Gly Tyr Thr Val Leu His Leu Ala
     50                  55                  60 gcc atg cgc aaa gag ccg tcc atc atc ata tct ctt ctc aag aga ggt      241
Ala Met Arg Lys Glu Pro Ser Ile Ile Ile Ser Leu Leu Lys Arg Gly
 65                  70                  75                  80 gcc aat gcg tct ggc ttc acg tgt gat gga cgc agt gcg gtt aat ata      289
Ala Asn Ala Ser Gly Phe Thr Cys Asp Gly Arg Ser Ala Val Asn Ile
                 85                  90                  95 tgt aga aga ttg aca act cca aag gat tat cat acg aaa aca gct gcg      337
Cys Arg Arg Leu Thr Thr Pro Lys Asp Tyr His Thr Lys Thr Ala Ala
                100                 105                 110 aaa ggg agg gaa gct agt aaa gca cgg tta tgt ata gat ctc ttg gaa      385
Lys Gly Arg Glu Ala Ser Lys Ala Arg Leu Cys Ile Asp Leu Leu Glu
            115                 120                 125 aga gaa gta agg agg aac cct atg gtt gtt gat tca cca atg tgt tcc      433
Arg Glu Val Arg Arg Asn Pro Met Val Val Asp Ser Pro Met Cys Ser
130                 135                 140 ctt tct atg cct gaa gat ctc caa atg aga ctg tta tac ctt gaa aat      481
```

```
Leu Ser Met Pro Glu Asp Leu Gln Met Arg Leu Leu Tyr Leu Glu Asn
145                 150                 155                 160 cga gtt ggc ctt gct caa ct                                          501
Arg Val Gly Leu Ala Gln
                165
```

<210> SEQ ID NO 52
<211> LENGTH: 166
<212> TYPE: PRT
<213> ORGANISM: Brassica napus

<400> SEQUENCE: 52

```
Ala Leu Asp Ser Asp Asp Val Glu Phe Val Lys Leu Leu Leu Thr Glu
1               5                   10                  15

Ser Asp Ile Thr Leu Asp Glu Ala Asn Gly Leu His Tyr Ser Val Val
                20                  25                  30

Tyr Ser Asp Pro Lys Val Val Ala Glu Ile Leu Thr Leu Asp Met Gly
            35                  40                  45

Asp Val Asn His Arg Asn Ser Arg Gly Tyr Thr Val Leu His Leu Ala
        50                  55                  60

Ala Met Arg Lys Glu Pro Ser Ile Ile Ile Ser Leu Leu Lys Arg Gly
65                  70                  75                  80

Ala Asn Ala Ser Gly Phe Thr Cys Asp Gly Arg Ser Ala Val Asn Ile
                85                  90                  95

Cys Arg Arg Leu Thr Thr Pro Lys Asp Tyr His Thr Lys Thr Ala Ala
            100                 105                 110

Lys Gly Arg Glu Ala Ser Lys Ala Arg Leu Cys Ile Asp Leu Leu Glu
        115                 120                 125

Arg Glu Val Arg Arg Asn Pro Met Val Val Asp Ser Pro Met Cys Ser
    130                 135                 140

Leu Ser Met Pro Glu Asp Leu Gln Met Arg Leu Leu Tyr Leu Glu Asn
145                 150                 155                 160

Arg Val Gly Leu Ala Gln
                165
```

<210> SEQ ID NO 53
<211> LENGTH: 501
<212> TYPE: DNA
<213> ORGANISM: Brassica napus
<220> FEATURE:
<221> NAME/KEY: CDS
<222> LOCATION: (2)..(499)
<223> OTHER INFORMATION: Canola B

<400> SEQUENCE: 53

```
g gca ttg gat tct gat gat gtt gag ttt gtg aag ctt ctt ttg acc gag    49
  Ala Leu Asp Ser Asp Asp Val Glu Phe Val Lys Leu Leu Leu Thr Glu
  1               5                   10                  15 tca gat atc act cta gat gaa gcc aat ggt ctt cat tac tca gtg gtg    97
Ser Asp Ile Thr Leu Asp Glu Ala Asn Gly Leu His Tyr Ser Val Val
                20                  25                  30 tat agt gat ccc aaa gtt gtt gcc gag att ctt act ctt gat atg ggt   145
Tyr Ser Asp Pro Lys Val Val Ala Glu Ile Leu Thr Leu Asp Met Gly
            35                  40                  45 gat gtt aac cac aga aac tca cgt ggc tac acg gtt ctg cat ctc gca   193
Asp Val Asn His Arg Asn Ser Arg Gly Tyr Thr Val Leu His Leu Ala
        50                  55                  60 gcc atg cgc aaa gag ccg tcc atc atc ata tct ctt ctc aag aaa ggt   241
Ala Met Arg Lys Glu Pro Ser Ile Ile Ile Ser Leu Leu Lys Lys Gly
65                  70                  75                  80
```

```
gcc aat gcg tct ggc ttc acc tgt gat gga cgc agt gcg gtt aat ata      289
Ala Asn Ala Ser Gly Phe Thr Cys Asp Gly Arg Ser Ala Val Asn Ile
                85                  90                  95 tgt aga aga ttg aca act cca aag gat tat cat act aaa aca gct gcg      337
Cys Arg Arg Leu Thr Thr Pro Lys Asp Tyr His Thr Lys Thr Ala Ala
        100                 105                 110 aaa ggg agg gaa gct agt aaa gca cgg tta tgt ata gat ctc ttg gaa      385
Lys Gly Arg Glu Ala Ser Lys Ala Arg Leu Cys Ile Asp Leu Leu Glu
            115                 120                 125 aga gaa gta agg agg aac cct atg gtt gtt gag tca cca atg tgt tct      433
Arg Glu Val Arg Arg Asn Pro Met Val Val Glu Ser Pro Met Cys Ser
        130                 135                 140 ctt tct atg cct gaa gat ctc caa atg aga ctg tta tac ctt gaa aat      481
Leu Ser Met Pro Glu Asp Leu Gln Met Arg Leu Leu Tyr Leu Glu Asn
145                 150                 155                 160 cga gtt ggc ctg gct caa ct                                            501
Arg Val Gly Leu Ala Gln
                165

<210> SEQ ID NO 54
<211> LENGTH: 166
<212> TYPE: PRT
<213> ORGANISM: Brassica napus

<400> SEQUENCE: 54

Ala Leu Asp Ser Asp Asp Val Glu Phe Val Lys Leu Leu Thr Glu
1               5                   10                  15

Ser Asp Ile Thr Leu Asp Glu Ala Asn Gly Leu His Tyr Ser Val Val
                20                  25                  30

Tyr Ser Asp Pro Lys Val Val Ala Glu Ile Leu Thr Leu Asp Met Gly
            35                  40                  45

Asp Val Asn His Arg Asn Ser Arg Gly Tyr Thr Val Leu His Leu Ala
        50                  55                  60

Ala Met Arg Lys Glu Pro Ser Ile Ile Ser Leu Leu Lys Lys Gly
65                  70                  75                  80

Ala Asn Ala Ser Gly Phe Thr Cys Asp Gly Arg Ser Ala Val Asn Ile
                85                  90                  95

Cys Arg Arg Leu Thr Thr Pro Lys Asp Tyr His Thr Lys Thr Ala Ala
            100                 105                 110

Lys Gly Arg Glu Ala Ser Lys Ala Arg Leu Cys Ile Asp Leu Leu Glu
        115                 120                 125

Arg Glu Val Arg Arg Asn Pro Met Val Val Glu Ser Pro Met Cys Ser
    130                 135                 140

Leu Ser Met Pro Glu Asp Leu Gln Met Arg Leu Leu Tyr Leu Glu Asn
145                 150                 155                 160

Arg Val Gly Leu Ala Gln
                165

<210> SEQ ID NO 55
<211> LENGTH: 498
<212> TYPE: DNA
<213> ORGANISM: Brassica napus
<220> FEATURE:
<221> NAME/KEY: CDS
<222> LOCATION: (2)..(496)
<223> OTHER INFORMATION: Canola C

<400> SEQUENCE: 55 g gca ctg gat tct gat gat gtt gag ctt gtg aag ctt ctt ttg acc gag   49
```

```
  Ala Leu Asp Ser Asp Val Glu Leu Val Lys Leu Leu Leu Thr Glu
   1               5                  10                  15 tca gat atc act cta gat gaa gcc aat ggt ctg cat tac tca gtg gtg      97
Ser Asp Ile Thr Leu Asp Glu Ala Asn Gly Leu His Tyr Ser Val Val
                20                  25                  30 tat agt gat ccc aaa gtt gtt gca gag ata ctt gcc ctt ggt tta ggt     145
Tyr Ser Asp Pro Lys Val Val Ala Glu Ile Leu Ala Leu Gly Leu Gly
            35                  40                  45 gat gtc aat cac aga aac tca cgt ggc tac tcg gtt ctt cat ttc gct     193
Asp Val Asn His Arg Asn Ser Arg Gly Tyr Ser Val Leu His Phe Ala
        50                  55                  60 gcc atg cgt aga gag cct tcc atc atc ata tct ctt ctc aag gaa ggc     241
Ala Met Arg Arg Glu Pro Ser Ile Ile Ile Ser Leu Leu Lys Glu Gly
 65                  70                  75                  80 gcc aat gcg tct agc ttc act ttt gat gga cgc agt gcg gtt aat ata     289
Ala Asn Ala Ser Ser Phe Thr Phe Asp Gly Arg Ser Ala Val Asn Ile
                85                  90                  95 tgt agg aga ctg aca act cca aag gat tat cat aca aag aca tcc aaa     337
Cys Arg Arg Leu Thr Thr Pro Lys Asp Tyr His Thr Lys Thr Ser Lys
            100                 105                 110 aag agg gaa gct agt aaa gca agg ctg tgc ata gat ctc ttg gaa aga     385
Lys Arg Glu Ala Ser Lys Ala Arg Leu Cys Ile Asp Leu Leu Glu Arg
        115                 120                 125 gag gtt agg agg aac cct atg ctt gct gat acg cca atg tgt tca ctt     433
Glu Val Arg Arg Asn Pro Met Leu Ala Asp Thr Pro Met Cys Ser Leu
    130                 135                 140 act atg cct gaa gat ctc caa atg aga ctg tta tac ctt gaa aat cga     481
Thr Met Pro Glu Asp Leu Gln Met Arg Leu Leu Tyr Leu Glu Asn Arg
145                 150                 155                 160 gtt ggt ctt gct aaa ct                                               498
Val Gly Leu Ala Lys
                165

<210> SEQ ID NO 56
<211> LENGTH: 165
<212> TYPE: PRT
<213> ORGANISM: Brassica napus

<400> SEQUENCE: 56

Ala Leu Asp Ser Asp Val Glu Leu Val Lys Leu Leu Leu Thr Glu
 1               5                  10                  15

Ser Asp Ile Thr Leu Asp Glu Ala Asn Gly Leu His Tyr Ser Val Val
                20                  25                  30

Tyr Ser Asp Pro Lys Val Val Ala Glu Ile Leu Ala Leu Gly Leu Gly
            35                  40                  45

Asp Val Asn His Arg Asn Ser Arg Gly Tyr Ser Val Leu His Phe Ala
        50                  55                  60

Ala Met Arg Arg Glu Pro Ser Ile Ile Ile Ser Leu Leu Lys Glu Gly
 65                  70                  75                  80

Ala Asn Ala Ser Ser Phe Thr Phe Asp Gly Arg Ser Ala Val Asn Ile
                85                  90                  95

Cys Arg Arg Leu Thr Thr Pro Lys Asp Tyr His Thr Lys Thr Ser Lys
            100                 105                 110

Lys Arg Glu Ala Ser Lys Ala Arg Leu Cys Ile Asp Leu Leu Glu Arg
        115                 120                 125

Glu Val Arg Arg Asn Pro Met Leu Ala Asp Thr Pro Met Cys Ser Leu
    130                 135                 140

Thr Met Pro Glu Asp Leu Gln Met Arg Leu Leu Tyr Leu Glu Asn Arg
```

<210> SEQ ID NO 57
<211> LENGTH: 498
<212> TYPE: DNA
<213> ORGANISM: Brassica napus
<220> FEATURE:
<221> NAME/KEY: CDS
<222> LOCATION: (2)..(496)
<223> OTHER INFORMATION: Canola D

<400> SEQUENCE: 57

```
g gca ctg gac tct gat gat gtt gag ctt gtc aag atg ctt ttg aca gaa      49
  Ala Leu Asp Ser Asp Asp Val Glu Leu Val Lys Met Leu Leu Thr Glu
    1               5                  10                  15 gga cac acg agt cta gac gac gcc tac gct ctt cac tac gct gtt gca        97
Gly His Thr Ser Leu Asp Asp Ala Tyr Ala Leu His Tyr Ala Val Ala
             20                  25                  30 cat tcc gat gtg aag acg gcc tct gat ctc ata gac ctt gag ctt gcg       145
His Ser Asp Val Lys Thr Ala Ser Asp Leu Ile Asp Leu Glu Leu Ala
         35                  40                  45 gat gtt gac cat aga aac ctg agg ggg tac acg gcg ctt cac gtt gct       193
Asp Val Asp His Arg Asn Leu Arg Gly Tyr Thr Ala Leu His Val Ala
     50                  55                  60 gcg atg agg aac gag ccg aag ctg atg gtt tat tta ttg act aaa ggt       241
Ala Met Arg Asn Glu Pro Lys Leu Met Val Tyr Leu Leu Thr Lys Gly
 65                  70                  75                  80 gcg aat gcg tcg gag aca acg ttt gac ggt aga acg gct ctt gtg att       289
Ala Asn Ala Ser Glu Thr Thr Phe Asp Gly Arg Thr Ala Leu Val Ile
                 85                  90                  95 gca aaa aga ctc act aaa gct tct gag tat aat gct agt acg gag caa       337
Ala Lys Arg Leu Thr Lys Ala Ser Glu Tyr Asn Ala Ser Thr Glu Gln
            100                 105                 110 ggg aag cct tct ctg aaa gga ggg cta tgc ata gag gta cta gag cat       385
Gly Lys Pro Ser Leu Lys Gly Gly Leu Cys Ile Glu Val Leu Glu His
        115                 120                 125 gcg cgg aaa cta ggt agg ttg cct aga gat ggt tta cct tct ctt cca       433
Ala Arg Lys Leu Gly Arg Leu Pro Arg Asp Gly Leu Pro Ser Leu Pro
    130                 135                 140 gct act cct gat gaa ctg agg atg agg ttg ctc tac ctt gaa aat cga       481
Ala Thr Pro Asp Glu Leu Arg Met Arg Leu Leu Tyr Leu Glu Asn Arg
145                 150                 155                 160 gtt ggc ctg gct caa ct                                                498
Val Gly Leu Ala Gln
                165
```

<210> SEQ ID NO 58
<211> LENGTH: 165
<212> TYPE: PRT
<213> ORGANISM: Brassica napus

<400> SEQUENCE: 58

```
Ala Leu Asp Ser Asp Asp Val Glu Leu Val Lys Met Leu Leu Thr Glu
  1               5                  10                  15

Gly His Thr Ser Leu Asp Asp Ala Tyr Ala Leu His Tyr Ala Val Ala
             20                  25                  30

His Ser Asp Val Lys Thr Ala Ser Asp Leu Ile Asp Leu Glu Leu Ala
         35                  40                  45

Asp Val Asp His Arg Asn Leu Arg Gly Tyr Thr Ala Leu His Val Ala
```

```
              50                  55                  60
Ala Met Arg Asn Glu Pro Lys Leu Met Val Tyr Leu Leu Thr Lys Gly
 65                  70                  75                  80

Ala Asn Ala Ser Glu Thr Thr Phe Asp Gly Arg Thr Ala Leu Val Ile
                 85                  90                  95

Ala Lys Arg Leu Thr Lys Ala Ser Glu Tyr Asn Ala Ser Thr Glu Gln
            100                 105                 110

Gly Lys Pro Ser Leu Lys Gly Gly Leu Cys Ile Glu Val Leu Glu His
        115                 120                 125

Ala Arg Lys Leu Gly Arg Leu Pro Arg Asp Gly Leu Pro Ser Leu Pro
    130                 135                 140

Ala Thr Pro Asp Glu Leu Arg Met Arg Leu Leu Tyr Leu Glu Asn Arg
145                 150                 155                 160

Val Gly Leu Ala Gln
                165

<210> SEQ ID NO 59
<211> LENGTH: 31
<212> TYPE: DNA
<213> ORGANISM: Artificial Sequence
<220> FEATURE:
<223> OTHER INFORMATION: Description of Artificial Sequence: PCR primer
      NIM3A

<400> SEQUENCE: 59
tagatgawgc mtaygctcty caytatgctg t                                         31

<210> SEQ ID NO 60
<211> LENGTH: 32
<212> TYPE: DNA
<213> ORGANISM: Artificial Sequence
<220> FEATURE:
<223> OTHER INFORMATION: Description of Artificial Sequence: PCR primer
      NIM3B

<400> SEQUENCE: 60
ggctcyttmc kcatggcagc aayrtgaags ac                                        32

<210> SEQ ID NO 61
<211> LENGTH: 148
<212> TYPE: DNA
<213> ORGANISM: Lycopersicon esculentum
<220> FEATURE:
<221> NAME/KEY: CDS
<222> LOCATION: (4)..(147)
<223> OTHER INFORMATION: Tomato B

<400> SEQUENCE: 61 tag atg atg cat atg ctc ttc att atg ctg ttg cat att gtg acc cca           48
    Met Met His Met Leu Phe Ile Met Leu Leu His Ile Val Thr Pro
     1               5                  10                  15 agg ttg ttg ctg agg ttc ttg gac tgg gtg ttg cta atg tca acc ttc           96
Arg Leu Leu Leu Arg Phe Leu Asp Trp Val Leu Leu Met Ser Thr Phe
                 20                  25                  30 gga atg cac gtg gtt aca ctg tcc ttc acg ttg ctg cca tgc gga aag          144
Gly Met His Val Val Thr Leu Ser Phe Thr Leu Leu Pro Cys Gly Lys
             35                  40                  45 agc c                                                                    148
Ser

<210> SEQ ID NO 62
<211> LENGTH: 48
```

```
<212> TYPE: PRT
<213> ORGANISM: Lycopersicon esculentum

<400> SEQUENCE: 62

Met Met His Met Leu Phe Ile Met Leu Leu His Ile Val Thr Pro Arg
 1               5                  10                  15

Leu Leu Leu Arg Phe Leu Asp Trp Val Leu Leu Met Ser Thr Phe Gly
            20                  25                  30

Met His Val Val Thr Leu Ser Phe Thr Leu Leu Pro Cys Gly Lys Ser
        35                  40                  45

<210> SEQ ID NO 63
<211> LENGTH: 2296
<212> TYPE: DNA
<213> ORGANISM: Beta vulgaris
<220> FEATURE:
<221> NAME/KEY: CDS
<222> LOCATION: (113)..(1927)
<223> OTHER INFORMATION: full-length Sugarbeet cDNA sequence

<400> SEQUENCE: 63
```

| | | |
|---|---|---|
| cacacacaca cccgacgccg tatgcgtatc cattctctct cctcaacctc cctttgactt | 60 | |
| cctcttactc caccatcttc aatgtcgtcg atttccaatc tctaacattc ac atg aca<br>                                                                                                                                                        Met Thr<br>                                                                                                                                                          1 | 118 | |

```
acc acc tcc aca aca atg gtg atc gat tct cgc acc gct ttc tcc gat      166
Thr Thr Ser Thr Thr Met Val Ile Asp Ser Arg Thr Ala Phe Ser Asp
        5                  10                  15 tcc aac gac atc agc aat ggc agt agc atc tgc tgc gtc gcc gca aca      214
Ser Asn Asp Ile Ser Asn Gly Ser Ser Ile Cys Cys Val Ala Ala Thr
 20                  25                  30 aca act aca aca aca acc gcc gca gaa aac tct ctc tcc ttt act ccc      262
Thr Thr Thr Thr Thr Thr Ala Ala Glu Asn Ser Leu Ser Phe Thr Pro
 35                  40                  45                  50 gac gcc gcc gct ctt ctc cgc ctc tct gaa aac ctc gac tcg ctt ttc      310
Asp Ala Ala Ala Leu Leu Arg Leu Ser Glu Asn Leu Asp Ser Leu Phe
                55                  60                  65 caa ccc tcg ctt tct ctc tcc gac tcc gac tct ttc gcc gac gct aaa      358
Gln Pro Ser Leu Ser Leu Ser Asp Ser Asp Ser Phe Ala Asp Ala Lys
            70                  75                  80 atc gtc gtt tcc ggt gat tcg cgt gaa gtc gcc gtt cat cgg tgt gtt      406
Ile Val Val Ser Gly Asp Ser Arg Glu Val Ala Val His Arg Cys Val
        85                  90                  95 ctc tcg tct cgg agc tcg ttc ttt cgg tcc gct ttt gct tcg aaa cga      454
Leu Ser Ser Arg Ser Ser Phe Phe Arg Ser Ala Phe Ala Ser Lys Arg
100                 105                 110 gag aag gag aag gag agg gat aaa gag aga gtg gtg aag ctt gag ctt      502
Glu Lys Glu Lys Glu Arg Asp Lys Glu Arg Val Val Lys Leu Glu Leu
115                 120                 125                 130 aag gat tta gct ggt gat ttt gag gtt gga ttt gat tcg gtt gtt gcg      550
Lys Asp Leu Ala Gly Asp Phe Glu Val Gly Phe Asp Ser Val Val Ala
                135                 140                 145 gtt tta ggt tat ttg tat agt ggc aaa gtt agg aat ttg cct aga gga      598
Val Leu Gly Tyr Leu Tyr Ser Gly Lys Val Arg Asn Leu Pro Arg Gly
            150                 155                 160 att tgt gtt tgt gtt gat gag gat tgc tct cat gaa gct tgt cgt cct      646
Ile Cys Val Cys Val Asp Glu Asp Cys Ser His Glu Ala Cys Arg Pro
        165                 170                 175 gct gtt gat ttt gtt gtt gag gtt ctc tat ttg tct cac aaa ttc gag      694
Ala Val Asp Phe Val Val Glu Val Leu Tyr Leu Ser His Lys Phe Glu
    180                 185                 190
```

```
att gtc gaa ttg gtt tcg ctt tat cag agg cac cta ctg gat att ctt      742
Ile Val Glu Leu Val Ser Leu Tyr Gln Arg His Leu Leu Asp Ile Leu
195                 200                 205                 210 gac aag att gca cca gat gac gtt cta gta gtg tta tct gtc gct gag      790
Asp Lys Ile Ala Pro Asp Asp Val Leu Val Val Leu Ser Val Ala Glu
            215                 220                 225 atg tgt gga aat gcg tgt gac gga ttg ctg gca agg tgt att gac aag      838
Met Cys Gly Asn Ala Cys Asp Gly Leu Leu Ala Arg Cys Ile Asp Lys
                230                 235                 240 att gtg agg tcc gat att gac gta acc acc att gat aaa tcc ttg ccg      886
Ile Val Arg Ser Asp Ile Asp Val Thr Thr Ile Asp Lys Ser Leu Pro
            245                 250                 255 cag aat gtt gtg aaa cag ata atc gac acg cga aag gaa ctt ggg ttt      934
Gln Asn Val Val Lys Gln Ile Ile Asp Thr Arg Lys Glu Leu Gly Phe
260                 265                 270 act gaa cct ggg cgt gtt gag ttt cct gat aag cat gtg aag aga ata      982
Thr Glu Pro Gly Arg Val Glu Phe Pro Asp Lys His Val Lys Arg Ile
275                 280                 285                 290 cac aga gct ttg gaa tcc gat gat gta gag tta gtc aga atg ctt tta     1030
His Arg Ala Leu Glu Ser Asp Asp Val Glu Leu Val Arg Met Leu Leu
                295                 300                 305 aaa gag cgc cat aca act cta gat gat gca tat gcc ctt cac tat gct     1078
Lys Glu Arg His Thr Thr Leu Asp Asp Ala Tyr Ala Leu His Tyr Ala
            310                 315                 320 gtg gca cat tgt gat gcc aag acc acc acg gag ctt ctt gag ctt ggg     1126
Val Ala His Cys Asp Ala Lys Thr Thr Thr Glu Leu Leu Glu Leu Gly
                325                 330                 335 ctt gca gat gtt aat ctt aga aat cta agg ggt cac act gtg cta cat     1174
Leu Ala Asp Val Asn Leu Arg Asn Leu Arg Gly His Thr Val Leu His
            340                 345                 350 gtg gca gcc atg aga aaa gag cct aag ata att gta tcc ttg tta acc     1222
Val Ala Ala Met Arg Lys Glu Pro Lys Ile Ile Val Ser Leu Leu Thr
355                 360                 365                 370 aag gga gcc cat ccg tct gat ata aca tca gat gat aaa aaa gca ctg     1270
Lys Gly Ala His Pro Ser Asp Ile Thr Ser Asp Asp Lys Lys Ala Leu
                375                 380                 385 cag ata gca aag aga cta aca aaa gct gtg gac ttc tat aaa act aca     1318
Gln Ile Ala Lys Arg Leu Thr Lys Ala Val Asp Phe Tyr Lys Thr Thr
            390                 395                 400 gaa caa gga aaa gat gca cca aag gat cgg ttg tgc att gaa ata ctg     1366
Glu Gln Gly Lys Asp Ala Pro Lys Asp Arg Leu Cys Ile Glu Ile Leu
                405                 410                 415 gag caa gct gaa aga aga gaa cca ttg cta gga gaa ggt tct gtt tct     1414
Glu Gln Ala Glu Arg Arg Glu Pro Leu Leu Gly Glu Gly Ser Val Ser
420                 425                 430 ctt gca aag gca gga gat gat ctg cgt atg aag cta tta tat ctt gaa     1462
Leu Ala Lys Ala Gly Asp Asp Leu Arg Met Lys Leu Leu Tyr Leu Glu
435                 440                 445                 450 aat aga gtt gca ctt gct cgg ttg ctc ttt cca atg gaa gcg aaa gtg     1510
Asn Arg Val Ala Leu Ala Arg Leu Leu Phe Pro Met Glu Ala Lys Val
            455                 460                 465 gct atg gat att gct caa gtg gac gga act tct gaa ttc aca ttg tca     1558
Ala Met Asp Ile Ala Gln Val Asp Gly Thr Ser Glu Phe Thr Leu Ser
                470                 475                 480 aag aat ata gct gat gca cga aga aat gcg gtg gac ttg aat gag gct     1606
Lys Asn Ile Ala Asp Ala Arg Arg Asn Ala Val Asp Leu Asn Glu Ala
            485                 490                 495 ccc ttt ata ttg aaa gag gag cat ttg cag agg atg aaa gca ctg tct     1654
Pro Phe Ile Leu Lys Glu Glu His Leu Gln Arg Met Lys Ala Leu Ser
```

-continued

```
            500                 505                 510
aaa act gtt gag ctt ggc aag cgt ttc ttt cca cgc tgc tcc gat gtt    1702
Lys Thr Val Glu Leu Gly Lys Arg Phe Phe Pro Arg Cys Ser Asp Val
515                 520                 525                 530 ctt aat aag att atg gac gcc gaa gat cta tca cag ctt gca ttt tta    1750
Leu Asn Lys Ile Met Asp Ala Glu Asp Leu Ser Gln Leu Ala Phe Leu
                535                 540                 545 gga aaa gat act cca gag gaa cgg caa agg aag aga aaa cga tac ctt    1798
Gly Lys Asp Thr Pro Glu Glu Arg Gln Arg Lys Arg Lys Arg Tyr Leu
        550                 555                 560 gaa ctg caa gac gct tta act aag gct ttt aca gag gac aaa gaa gag    1846
Glu Leu Gln Asp Ala Leu Thr Lys Ala Phe Thr Glu Asp Lys Glu Glu
            565                 570                 575 ttt gac cgt tct aca tta tca tca tcg tcg tcg tcg act cca atg ggg    1894
Phe Asp Arg Ser Thr Leu Ser Ser Ser Ser Ser Ser Thr Pro Met Gly
580                 585                 590 agg cca tat ggt aag acc aat ttc aag agg taa ctccttagca gctcaaagtt  1947
Arg Pro Tyr Gly Lys Thr Asn Phe Lys Arg
595                 600                 605 gcatacgacg tcacttgtat aatattcatg tatatgtatg aaaatttctt tttgttctcc  2007
ccttctattg atggccacgg tttcgatctt tttggtctgt attataattt ttgaccgatt  2067
acttgataga attgtattct atacatcttt ataagctcat agtaacacca gatttaggta  2127
ctatccgttg gagacacata ctcttgtgtg cgatgatgaa tcaatcatca gattacatta  2187
cacgagccat ttcctgccat attgtaattc atgtatcaag gtacaaataa atagcgtcgt  2247
ggggttgcac ctcttgcatt atcgaaaaaa aaaaaaaaaa aaaaaaaa               2296
```

<210> SEQ ID NO 64
<211> LENGTH: 604
<212> TYPE: PRT
<213> ORGANISM: Beta vulgaris

<400> SEQUENCE: 64

```
Met Thr Thr Thr Ser Thr Thr Met Val Ile Asp Ser Arg Thr Ala Phe
 1               5                  10                  15

Ser Asp Ser Asn Asp Ile Ser Asn Gly Ser Ser Ile Cys Cys Val Ala
                20                  25                  30

Ala Thr Thr Thr Thr Thr Thr Ala Ala Glu Asn Ser Leu Ser Phe
            35                  40                  45

Thr Pro Asp Ala Ala Leu Leu Arg Leu Ser Glu Asn Leu Asp Ser
        50                  55                  60

Leu Phe Gln Pro Ser Leu Ser Leu Ser Asp Ser Asp Ser Phe Ala Asp
65                  70                  75                  80

Ala Lys Ile Val Val Ser Gly Asp Ser Arg Glu Val Ala Val His Arg
                85                  90                  95

Cys Val Leu Ser Ser Arg Ser Ser Phe Phe Arg Ser Ala Phe Ala Ser
                100                 105                 110

Lys Arg Glu Lys Glu Lys Glu Arg Asp Lys Glu Arg Val Val Lys Leu
            115                 120                 125

Glu Leu Lys Asp Leu Ala Gly Asp Phe Glu Val Gly Phe Asp Ser Val
        130                 135                 140

Val Ala Val Leu Gly Tyr Leu Tyr Ser Gly Lys Val Arg Asn Leu Pro
145                 150                 155                 160

Arg Gly Ile Cys Val Cys Val Asp Glu Asp Cys Ser His Glu Ala Cys
                165                 170                 175
```

-continued

```
Arg Pro Ala Val Asp Phe Val Val Glu Val Leu Tyr Leu Ser His Lys
            180                 185                 190

Phe Glu Ile Val Glu Leu Val Ser Leu Tyr Gln Arg His Leu Leu Asp
            195                 200                 205

Ile Leu Asp Lys Ile Ala Pro Asp Asp Val Leu Val Val Leu Ser Val
            210                 215                 220

Ala Glu Met Cys Gly Asn Ala Cys Asp Gly Leu Leu Ala Arg Cys Ile
225                 230                 235                 240

Asp Lys Ile Val Arg Ser Asp Ile Asp Val Thr Thr Ile Asp Lys Ser
                    245                 250                 255

Leu Pro Gln Asn Val Val Lys Gln Ile Ile Asp Thr Arg Lys Glu Leu
                    260                 265                 270

Gly Phe Thr Glu Pro Gly Arg Val Glu Phe Pro Asp Lys His Val Lys
                275                 280                 285

Arg Ile His Arg Ala Leu Glu Ser Asp Asp Val Glu Leu Val Arg Met
            290                 295                 300

Leu Leu Lys Glu Arg His Thr Thr Leu Asp Asp Ala Tyr Ala Leu His
305                 310                 315                 320

Tyr Ala Val Ala His Cys Asp Ala Lys Thr Thr Thr Glu Leu Leu Glu
                    325                 330                 335

Leu Gly Leu Ala Asp Val Asn Leu Arg Asn Leu Arg Gly His Thr Val
                340                 345                 350

Leu His Val Ala Ala Met Arg Lys Glu Pro Lys Ile Ile Val Ser Leu
            355                 360                 365

Leu Thr Lys Gly Ala His Pro Ser Asp Ile Thr Ser Asp Asp Lys Lys
            370                 375                 380

Ala Leu Gln Ile Ala Lys Arg Leu Thr Lys Ala Val Asp Phe Tyr Lys
385                 390                 395                 400

Thr Thr Glu Gln Gly Lys Asp Ala Pro Lys Asp Arg Leu Cys Ile Glu
                    405                 410                 415

Ile Leu Glu Gln Ala Glu Arg Arg Glu Pro Leu Leu Gly Glu Gly Ser
                420                 425                 430

Val Ser Leu Ala Lys Ala Gly Asp Asp Leu Arg Met Lys Leu Leu Tyr
            435                 440                 445

Leu Glu Asn Arg Val Ala Leu Ala Arg Leu Leu Phe Pro Met Glu Ala
            450                 455                 460

Lys Val Ala Met Asp Ile Ala Gln Val Asp Gly Thr Ser Glu Phe Thr
465                 470                 475                 480

Leu Ser Lys Asn Ile Ala Asp Ala Arg Arg Asn Ala Val Asp Leu Asn
                    485                 490                 495

Glu Ala Pro Phe Ile Leu Lys Glu Glu His Leu Gln Arg Met Lys Ala
                500                 505                 510

Leu Ser Lys Thr Val Glu Leu Gly Lys Arg Phe Phe Pro Arg Cys Ser
            515                 520                 525

Asp Val Leu Asn Lys Ile Met Asp Ala Glu Asp Leu Ser Gln Leu Ala
            530                 535                 540

Phe Leu Gly Lys Asp Thr Pro Glu Glu Arg Gln Arg Lys Arg Lys Arg
545                 550                 555                 560

Tyr Leu Glu Leu Gln Asp Ala Leu Thr Lys Ala Phe Thr Glu Asp Lys
                    565                 570                 575

Glu Glu Phe Asp Arg Ser Thr Leu Ser Ser Ser Ser Ser Thr Pro
                580                 585                 590

Met Gly Arg Pro Tyr Gly Lys Thr Asn Phe Lys Arg
```

-continued

```
<210> SEQ ID NO 65
<211> LENGTH: 2844
<212> TYPE: DNA
<213> ORGANISM: Helianthus annuus
<220> FEATURE:
<221> NAME/KEY: CDS
<222> LOCATION: (737)..(2512)
<223> OTHER INFORMATION: full-length Sunflower B cDNA sequence

<400> SEQUENCE: 65
gacgataaaa cccctctctc tttttgctac caagaacctt cctactttct tgcaccaaag       60
tttctttgca ggttctttga agcttccttta tcatcatacg ttggtttgat attgttttg      120 atgcatcttt tcacatgggt tttgcttatt gagtgattat ctgttgtggg tatttgatac      180
aaattgaaaa aaagatgatt agatttggta tttagggttt tggttattga agattttatt      240
aattagggtt tgattagggt ttgattaaga ttcttgtatt ggatgggttg atttagatcc      300
agctgtttgt gggtttcaaa ttttttgtttt ggtatttgca tatctcattc taatctattc      360
agaggttgag gttctttagg tttgactttg actttgactt ttgggtactt tcttgtacat      420
gtataatgtt tgatttgatc cattatatgt gttttgtaat tgaatcatag caaatttttct      480 tgcctgtata tatatgtttt attgaggatt tggttcaagt tttgaccttt ttgggaaaaa      540
aagtcaaaca catattcttg ttcatgtagt tttgcaaatc aatcatttca caaatctttc      600
tttatgttgg gaatccatct caatcataaa aaagtttctt tctttctttg agttcttgtt      660
agctatgaaa gtttatgatt tgtccttttt gtgataaagt caaacccta atcatcctgg      720 gactttgact aaatcg atg gcg aat tca tcc gaa ccg tca tca tcc ata agc    772
                    Met Ala Asn Ser Ser Glu Pro Ser Ser Ser Ile Ser
                     1               5                   10 ttc acc tca tct tca cac ata tct aac ggc gca act agc tac aac ata       820
Phe Thr Ser Ser Ser His Ile Ser Asn Gly Ala Thr Ser Tyr Asn Ile
         15                  20                  25 ccc cca cca tca atc ccc gag cca cgg tcg aat att gaa atc att ggc       868
Pro Pro Pro Ser Ile Pro Glu Pro Arg Ser Asn Ile Glu Ile Ile Gly
 30                  35                  40 tta aat aga ctc agc aca aac cta gag aag ctc gta ttc gat tca ggt       916
Leu Asn Arg Leu Ser Thr Asn Leu Glu Lys Leu Val Phe Asp Ser Gly
 45                  50                  55                  60 tct gaa tct gat tgc aat tac agc gat gct gaa gtt gtt gtt gag ggt       964
Ser Glu Ser Asp Cys Asn Tyr Ser Asp Ala Glu Val Val Val Glu Gly
                 65                  70                  75 att tct gta ggc att cat cgg tgt att tta gcc act aga agt acg ttt      1012
Ile Ser Val Gly Ile His Arg Cys Ile Leu Ala Thr Arg Ser Thr Phe
             80                  85                  90 ttt agc gat ttg ttt aag aag aac aaa ggt tgt gta gag aag gac agt      1060
Phe Ser Asp Leu Phe Lys Lys Asn Lys Gly Cys Val Glu Lys Asp Ser
         95                 100                 105 aag ccg aaa tat aac atg agt gat ttg ttg ccg tat ggg agc gtt ggg      1108
Lys Pro Lys Tyr Asn Met Ser Asp Leu Leu Pro Tyr Gly Ser Val Gly
110                 115                 120 tat gat gcg ttt ctc gtg ttt tta agc tat gtt tat act ggg aaa ctg      1156
Tyr Asp Ala Phe Leu Val Phe Leu Ser Tyr Val Tyr Thr Gly Lys Leu
125                 130                 135                 140 aaa gcg tct cct ccg gag gtt tca acc tgc gtt gat gat ggg tgt ctt      1204
Lys Ala Ser Pro Pro Glu Val Ser Thr Cys Val Asp Asp Gly Cys Leu
                145                 150                 155 cat gat gct tgt tgg cct gct att aac ttt gct gtt gag ttg act tat      1252
```

```
                His Asp Ala Cys Trp Pro Ala Ile Asn Phe Ala Val Glu Leu Thr Tyr
                            160                 165                 170 gcg tct tcg gtt ttt caa gtt ccg gaa tta gtt tcg ctt ttt cag cgt       1300
Ala Ser Ser Val Phe Gln Val Pro Glu Leu Val Ser Leu Phe Gln Arg
            175                 180                 185 cgt ctt ctc aac ttt gtg gac aag gct ctt gtt gaa gac gtg atc ccg       1348
Arg Leu Leu Asn Phe Val Asp Lys Ala Leu Val Glu Asp Val Ile Pro
        190                 195                 200 atc ctt gtt gtg gcc ttt cac tgt cag ttg caa aac gtc tta tct cgt       1396
Ile Leu Val Val Ala Phe His Cys Gln Leu Gln Asn Val Leu Ser Arg
205                 210                 215                 220 tgc att gac cga gta gtt agg tca aag ctc gat act att tcc att gaa       1444
Cys Ile Asp Arg Val Val Arg Ser Lys Leu Asp Thr Ile Ser Ile Glu
                225                 230                 235 aaa gag ctt cca ttt gaa gtc acc caa atg atc aaa tcc att gat aac       1492
Lys Glu Leu Pro Phe Glu Val Thr Gln Met Ile Lys Ser Ile Asp Asn
            240                 245                 250 atc atc caa gaa gat gac gaa cat aca gtc gaa tca gaa gtc gtg tta       1540
Ile Ile Gln Glu Asp Asp Glu His Thr Val Glu Ser Glu Val Val Leu
        255                 260                 265 cgt gaa aag aga att aaa agc ata cac aaa gca tta gac tgt gac gat       1588
Arg Glu Lys Arg Ile Lys Ser Ile His Lys Ala Leu Asp Cys Asp Asp
    270                 275                 280 gtt gag ctt gtg aaa atg att tta gac gaa tcc aaa atc acg tta gat       1636
Val Glu Leu Val Lys Met Ile Leu Asp Glu Ser Lys Ile Thr Leu Asp
285                 290                 295                 300 gaa gcc tgc gct ctt cat tat gcg gtc atg tat tgt aat caa gaa gtt       1684
Glu Ala Cys Ala Leu His Tyr Ala Val Met Tyr Cys Asn Gln Glu Val
                305                 310                 315 gct aag gag att ctt aac tta aac cgt gcg gat gtt aat ctt aga aac       1732
Ala Lys Glu Ile Leu Asn Leu Asn Arg Ala Asp Val Asn Leu Arg Asn
            320                 325                 330 tca cga gat tac acc gtg ctt cat gtt gct gcc atg cgt aaa gaa cca       1780
Ser Arg Asp Tyr Thr Val Leu His Val Ala Ala Met Arg Lys Glu Pro
        335                 340                 345 tca ctt att gtt tcg att cta agc aaa ggc gcg tgt gca tcg gat act       1828
Ser Leu Ile Val Ser Ile Leu Ser Lys Gly Ala Cys Ala Ser Asp Thr
    350                 355                 360 act ttt gat gga caa agt gcg gtt agt att tgc agg aga cga aca agg       1876
Thr Phe Asp Gly Gln Ser Ala Val Ser Ile Cys Arg Arg Arg Thr Arg
365                 370                 375                 380 ccc aag gat tat tat gtg aaa acc gaa cac ggg caa gaa aca aat aaa       1924
Pro Lys Asp Tyr Tyr Val Lys Thr Glu His Gly Gln Glu Thr Asn Lys
                385                 390                 395 gat cgt ata tgc atc gat gtt ttg gag cgg gaa ata aag agg aat ccg       1972
Asp Arg Ile Cys Ile Asp Val Leu Glu Arg Glu Ile Lys Arg Asn Pro
            400                 405                 410 atg ata ggc gat gtt tcc gtg tgt tct tca gca gtg gct gat gat ttg       2020
Met Ile Gly Asp Val Ser Val Cys Ser Ser Ala Val Ala Asp Asp Leu
        415                 420                 425 cat atg aat tta ctc tac tta gaa aac cga gtg gca ttt gct cga ctg       2068
His Met Asn Leu Leu Tyr Leu Glu Asn Arg Val Ala Phe Ala Arg Leu
    430                 435                 440 tta ttt ccg tca gaa gcg aaa cta gca atg gaa att gcg cat gcc caa       2116
Leu Phe Pro Ser Glu Ala Lys Leu Ala Met Glu Ile Ala His Ala Gln
445                 450                 455                 460 acg act gca cag tat ccg ggt cta ttg gca tcg aaa ggg tca aat ggt       2164
Thr Thr Ala Gln Tyr Pro Gly Leu Leu Ala Ser Lys Gly Ser Asn Gly
                465                 470                 475
```

```
aac tta agg gag atg gat ttg aac gag aca ccg ttg gtg cag aac aaa    2212
Asn Leu Arg Glu Met Asp Leu Asn Glu Thr Pro Leu Val Gln Asn Lys
        480                 485                 490 aga ttg ctt tca aga atg gaa gcc ctt tcc cgg aca gtg gaa atg ggt    2260
Arg Leu Leu Ser Arg Met Glu Ala Leu Ser Arg Thr Val Glu Met Gly
    495                 500                 505 agg cga tat ttc cct cat tgt tca gag gtt ctg gat aag ttc atg gag    2308
Arg Arg Tyr Phe Pro His Cys Ser Glu Val Leu Asp Lys Phe Met Glu
510                 515                 520 gac gat cta cag gat ctt ttt atc ctc gag aag ggt acc gaa gaa gaa    2356
Asp Asp Leu Gln Asp Leu Phe Ile Leu Glu Lys Gly Thr Glu Glu Glu
525                 530                 535                 540 caa gaa atc aaa agg acg cga ttt atg gag ctt aaa gaa gat gtc caa    2404
Gln Glu Ile Lys Arg Thr Arg Phe Met Glu Leu Lys Glu Asp Val Gln
            545                 550                 555 aga gcc ttt acc aag gac aag gcc gag ctt cat cgc ggt ttg tcc tca    2452
Arg Ala Phe Thr Lys Asp Lys Ala Glu Leu His Arg Gly Leu Ser Ser
                560                 565                 570 tca atg tac acc ccc aca gtg aga aac ggg tca aag agt aaa gcc cgc    2500
Ser Met Tyr Thr Pro Thr Val Arg Asn Gly Ser Lys Ser Lys Ala Arg
            575                 580                 585 aaa tac tca tga aaccccgtg tttctttgat gatcttttaa cacgctttta         2552
Lys Tyr Ser
    590 cgtgcctaat attagaggca aaacatatgt atgaagaaat aatggtggtg catgatgatg  2612 tttagggctc aggtttaggg tttatatgta ctaaattttg tgatttgacg ctaaaaatgc  2672 tatgttgttt ttttttttt ttggataata tggtgtgaaa gctaacgcct tttactagta   2732 gcatgttaat gtttgtgttt gaatcatagt tttttatgca tgtttgtttt acttgcacaa  2792 caactaataa atataatttt tcataataaa aaaaaaaaa aaaaaaaaaa aa           2844

<210> SEQ ID NO 66
<211> LENGTH: 591
<212> TYPE: PRT
<213> ORGANISM: Helianthus annuus

<400> SEQUENCE: 66

Met Ala Asn Ser Ser Glu Pro Ser Ser Ser Ile Ser Phe Thr Ser Ser
 1               5                  10                  15

Ser His Ile Ser Asn Gly Ala Thr Ser Tyr Asn Ile Pro Pro Pro Ser
                20                  25                  30

Ile Pro Glu Pro Arg Ser Asn Ile Glu Ile Ile Gly Leu Asn Arg Leu
            35                  40                  45

Ser Thr Asn Leu Glu Lys Leu Val Phe Asp Ser Gly Ser Glu Ser Asp
        50                  55                  60

Cys Asn Tyr Ser Asp Ala Glu Val Val Glu Gly Ile Ser Val Gly
65                  70                  75                  80

Ile His Arg Cys Ile Leu Ala Thr Arg Ser Thr Phe Ser Asp Leu
                85                  90                  95

Phe Lys Lys Asn Lys Gly Cys Val Glu Lys Asp Ser Lys Pro Lys Tyr
                100                 105                 110

Asn Met Ser Asp Leu Leu Pro Tyr Gly Ser Val Gly Tyr Asp Ala Phe
            115                 120                 125

Leu Val Phe Leu Ser Tyr Val Tyr Thr Gly Lys Leu Lys Ala Ser Pro
        130                 135                 140

Pro Glu Val Ser Thr Cys Val Asp Asp Gly Cys Leu His Asp Ala Cys
145                 150                 155                 160
```

-continued

```
Trp Pro Ala Ile Asn Phe Ala Val Glu Leu Thr Tyr Ala Ser Ser Val
            165                 170                 175
Phe Gln Val Pro Glu Leu Val Ser Leu Phe Gln Arg Arg Leu Leu Asn
            180                 185                 190
Phe Val Asp Lys Ala Leu Val Glu Asp Val Ile Pro Ile Leu Val Val
            195                 200                 205
Ala Phe His Cys Gln Leu Gln Asn Val Leu Ser Arg Cys Ile Asp Arg
            210                 215                 220
Val Val Arg Ser Lys Leu Asp Thr Ile Ser Ile Glu Lys Glu Leu Pro
225                 230                 235                 240
Phe Glu Val Thr Gln Met Ile Lys Ser Ile Asp Asn Ile Ile Gln Glu
            245                 250                 255
Asp Asp Glu His Thr Val Glu Ser Glu Val Val Leu Arg Glu Lys Arg
            260                 265                 270
Ile Lys Ser Ile His Lys Ala Leu Asp Cys Asp Asp Val Glu Leu Val
            275                 280                 285
Lys Met Ile Leu Asp Glu Ser Lys Ile Thr Leu Asp Glu Ala Cys Ala
290                 295                 300
Leu His Tyr Ala Val Met Tyr Cys Asn Gln Glu Val Ala Lys Glu Ile
305                 310                 315                 320
Leu Asn Leu Asn Arg Ala Asp Val Asn Leu Arg Asn Ser Arg Asp Tyr
            325                 330                 335
Thr Val Leu His Val Ala Ala Met Arg Lys Glu Pro Ser Leu Ile Val
            340                 345                 350
Ser Ile Leu Ser Lys Gly Ala Cys Ala Ser Asp Thr Thr Phe Asp Gly
            355                 360                 365
Gln Ser Ala Val Ser Ile Cys Arg Arg Thr Arg Pro Lys Asp Tyr
            370                 375                 380
Tyr Val Lys Thr Glu His Gly Gln Glu Thr Asn Lys Asp Arg Ile Cys
385                 390                 395                 400
Ile Asp Val Leu Glu Arg Glu Ile Lys Arg Asn Pro Met Ile Gly Asp
            405                 410                 415
Val Ser Val Cys Ser Ser Ala Val Ala Asp Asp Leu His Met Asn Leu
            420                 425                 430
Leu Tyr Leu Glu Asn Arg Val Ala Phe Ala Arg Leu Leu Phe Pro Ser
            435                 440                 445
Glu Ala Lys Leu Ala Met Glu Ile Ala His Ala Gln Thr Thr Ala Gln
            450                 455                 460
Tyr Pro Gly Leu Leu Ala Ser Lys Gly Ser Asn Gly Asn Leu Arg Glu
465                 470                 475                 480
Met Asp Leu Asn Glu Thr Pro Leu Val Gln Asn Lys Arg Leu Leu Ser
            485                 490                 495
Arg Met Glu Ala Leu Ser Arg Thr Val Glu Met Gly Arg Arg Tyr Phe
            500                 505                 510
Pro His Cys Ser Glu Val Leu Asp Lys Phe Met Glu Asp Asp Leu Gln
            515                 520                 525
Asp Leu Phe Ile Leu Glu Lys Gly Thr Glu Glu Gln Glu Ile Lys
            530                 535                 540
Arg Thr Arg Phe Met Glu Leu Lys Glu Asp Val Gln Arg Ala Phe Thr
545                 550                 555                 560
Lys Asp Lys Ala Glu Leu His Arg Gly Leu Ser Ser Ser Met Tyr Thr
            565                 570                 575
```

```
Pro Thr Val Arg Asn Gly Ser Lys Ser Lys Ala Arg Lys Tyr Ser
            580                 585                 590

<210> SEQ ID NO 67
<211> LENGTH: 1477
<212> TYPE: DNA
<213> ORGANISM: Arabidopsis thaliana
<220> FEATURE:
<221> NAME/KEY: CDS
<222> LOCATION: (1)..(804)
<223> OTHER INFORMATION: AtNMLc2 cDNA sequence
<220> FEATURE:
<221> NAME/KEY: misc_feature
<222> LOCATION: (1)..(1477)
<223> OTHER INFORMATION: n = a, t, c or g

<400> SEQUENCE: 67 atg agc aat ctt gaa gaa tct ttg aga tct cta tcg ttg gat ttc ctg      48
Met Ser Asn Leu Glu Glu Ser Leu Arg Ser Leu Ser Leu Asp Phe Leu
 1               5                  10                  15 aac cta cta atc aac ggt caa gct ttc tcc gac gtg act ttc agc gtt     96
Asn Leu Leu Ile Asn Gly Gln Ala Phe Ser Asp Val Thr Phe Ser Val
            20                  25                  30 gaa ggt cgt tta gtc cac gct cac cgt tgt atc ctc gcc gca cgg agg    144
Glu Gly Arg Leu Val His Ala His Arg Cys Ile Leu Ala Ala Arg Arg
        35                  40                  45 ctt ttc ttc cgc aaa ttc ttt tgt ggg aca gac tca cca caa cct gtc    192
Leu Phe Phe Arg Lys Phe Phe Cys Gly Thr Asp Ser Pro Gln Pro Val
    50                  55                  60 aca ggt ata gac ccg acc caa cat ggg tcc gta ccc gct agc cca aca    240
Thr Gly Ile Asp Pro Thr Gln His Gly Ser Val Pro Ala Ser Pro Thr
 65                  70                  75                  80 aga ggc tcc acg gcc cca gct gga att ata cca gtg aac tca gtc ggt    288
Arg Gly Ser Thr Ala Pro Ala Gly Ile Ile Pro Val Asn Ser Val Gly
                85                  90                  95 tat gag gtt ttt ctg ttg cta ctt cag ttt ctt tat agc gga caa gtc    336
Tyr Glu Val Phe Leu Leu Leu Leu Gln Phe Leu Tyr Ser Gly Gln Val
            100                 105                 110 tcc atc gtg ccg cag aaa cac gag cct aga cct aat tgt ggc gag aga    384
Ser Ile Val Pro Gln Lys His Glu Pro Arg Pro Asn Cys Gly Glu Arg
        115                 120                 125 gga tgt tgg cac act cat tgc tca gcc gcc gtt gat ctt gct ctt gat    432
Gly Cys Trp His Thr His Cys Ser Ala Ala Val Asp Leu Ala Leu Asp
    130                 135                 140 act ctc gcc gcc tct cgt tac ttc ggc gtc gag cag ctc gca ttg ctc    480
Thr Leu Ala Ala Ser Arg Tyr Phe Gly Val Glu Gln Leu Ala Leu Leu
145                 150                 155                 160 acc cag aaa caa ttg gca agc atg gtg gag aaa gcc tct atc gaa gat    528
Thr Gln Lys Gln Leu Ala Ser Met Val Glu Lys Ala Ser Ile Glu Asp
                165                 170                 175 gtg atg aaa gtt tta ata gca tca aga aag caa gac atg cat caa tta    576
Val Met Lys Val Leu Ile Ala Ser Arg Lys Gln Asp Met His Gln Leu
            180                 185                 190 tgg acc acc tgc tct cac tta gtt gct aaa tca ggt ctc cca cca gag    624
Trp Thr Thr Cys Ser His Leu Val Ala Lys Ser Gly Leu Pro Pro Glu
        195                 200                 205 att ctt gcc aag cat ctc cct att gac gtc gtc acc aaa ata gaa gag    672
Ile Leu Ala Lys His Leu Pro Ile Asp Val Val Thr Lys Ile Glu Glu
    210                 215                 220 ctt cgt ctt aaa tct tct ata gct cgc cgt tct cta atg cct cac aac    720
Leu Arg Leu Lys Ser Ser Ile Ala Arg Arg Ser Leu Met Pro His Asn
225                 230                 235                 240
```

```
cac cac cat gat ctc agc ggn gnt caa nac cta aag ntc aaa gtt aga    768
His His His Asp Leu Ser Xaa Xaa Gln Xaa Leu Lys Xaa Lys Val Arg
                 245                 250                 255 agg ttg agc cga ctt gga ttc ttc aac gng aac tag taaagctgat         814
Arg Leu Ser Arg Leu Gly Phe Phe Asn Xaa Asn
                 260                 265 ggtaatggan aaggactcca ttcttgatga agtcgtaagc attgcattac cgcttgttaa  874
aagctgtaga agagaagttg tgaagncttt ngcttgaagc ttggaagctg ccgatgtgaa  934
ttatccggcg ggtccggcaa ggnaaancac ctttgcactt cgcgggntga gatggtctct  994
ccagacatgg tggctgttct gttagcccnc catgcttgat cctaatgtga ggacagttgg  1054
tggaatcacg cctcttgata tccttagaac attaacttcg gatttcttgt tcaaggggca  1114
gttcctggat tgactcacat tgaaccgaat aaacttaggc tttgcctcga gcttgttcaa  1174
tccgctgcaa tggtgatatc tcgagaagaa ggaaacaata gcaacaacca aaacaatgat  1234
aacaataccg ggatttaccc tcatatgaat gaggagcaca atagtggaag cagtggaggg  1294
agcaataaca atttggattc aagattggtt tatctcaatc ttggagcagg tacgggtcag  1354
atgggtccag gtcgagatca agggatgac cataacagtc agagggaagg tatgagtcgg  1414
catcatcatc atcatcaaga cccatctaca atgtatcatc accatcatca acatcacttc  1474
tag                                                                1477
```

<210> SEQ ID NO 68
<211> LENGTH: 267
<212> TYPE: PRT
<213> ORGANISM: Arabidopsis thaliana

<400> SEQUENCE: 68

```
Met Ser Asn Leu Glu Glu Ser Leu Arg Ser Leu Ser Leu Asp Phe Leu
  1               5                  10                  15

Asn Leu Leu Ile Asn Gly Gln Ala Phe Ser Asp Val Thr Phe Ser Val
                 20                  25                  30

Glu Gly Arg Leu Val His Ala His Arg Cys Ile Leu Ala Ala Arg Arg
             35                  40                  45

Leu Phe Phe Arg Lys Phe Phe Cys Gly Thr Asp Ser Pro Gln Pro Val
 50                  55                  60

Thr Gly Ile Asp Pro Thr Gln His Gly Ser Val Pro Ala Ser Pro Thr
 65                  70                  75                  80

Arg Gly Ser Thr Ala Pro Ala Gly Ile Ile Pro Val Asn Ser Val Gly
                 85                  90                  95

Tyr Glu Val Phe Leu Leu Leu Gln Phe Leu Tyr Ser Gly Gln Val
                100                 105                 110

Ser Ile Val Pro Gln Lys His Glu Pro Arg Pro Asn Cys Gly Glu Arg
            115                 120                 125

Gly Cys Trp His Thr His Cys Ser Ala Ala Val Asp Leu Ala Leu Asp
130                 135                 140

Thr Leu Ala Ala Ser Arg Tyr Phe Gly Val Glu Gln Leu Ala Leu Leu
145                 150                 155                 160

Thr Gln Lys Gln Leu Ala Ser Met Val Glu Lys Ala Ser Ile Glu Asp
                165                 170                 175

Val Met Lys Val Leu Ile Ala Ser Arg Lys Gln Asp Met His Gln Leu
            180                 185                 190

Trp Thr Thr Cys Ser His Leu Val Ala Lys Ser Gly Leu Pro Pro Glu
        195                 200                 205
```

```
Ile Leu Ala Lys His Leu Pro Ile Asp Val Val Thr Lys Ile Glu Glu
    210                 215                 220
Leu Arg Leu Lys Ser Ser Ile Ala Arg Arg Ser Leu Met Pro His Asn
225                 230                 235                 240
His His His Asp Leu Ser Xaa Xaa Gln Xaa Leu Lys Xaa Lys Val Arg
                245                 250                 255
Arg Leu Ser Arg Leu Gly Phe Phe Asn Xaa Asn
            260                 265

<210> SEQ ID NO 69
<211> LENGTH: 1725
<212> TYPE: DNA
<213> ORGANISM: Arabidopsis thaliana
<220> FEATURE:
<221> NAME/KEY: CDS
<222> LOCATION: (1)..(1725)
<223> OTHER INFORMATION: AtNMLc4-1 cDNA sequence

<400> SEQUENCE: 69 atg gct gca act gca ata gag cca tct tca tct ata agt ttc aca tct       48
Met Ala Ala Thr Ala Ile Glu Pro Ser Ser Ser Ile Ser Phe Thr Ser
 1               5                  10                  15 tct cac tta tca aac cct tct cct gtt gtt act act tat cac tca gct       96
Ser His Leu Ser Asn Pro Ser Pro Val Val Thr Thr Tyr His Ser Ala
                20                  25                  30 gcc aat ctt gaa gag ctc agc tct aac ttg gag cag ctt ctc act aat      144
Ala Asn Leu Glu Glu Leu Ser Ser Asn Leu Glu Gln Leu Leu Thr Asn
            35                  40                  45 cca gat tgc gat tac act gac gca gag atc atc att gaa gaa gaa gct      192
Pro Asp Cys Asp Tyr Thr Asp Ala Glu Ile Ile Ile Glu Glu Glu Ala
        50                  55                  60 aac cct gtg agt gtt cat aga tgt gtt tta gct gct agg agc aag ttt      240
Asn Pro Val Ser Val His Arg Cys Val Leu Ala Ala Arg Ser Lys Phe
 65                  70                  75                  80 ttt ctt gat ctg ttt aag aaa gat aaa gat agt agt gag aag aaa cct      288
Phe Leu Asp Leu Phe Lys Lys Asp Lys Asp Ser Ser Glu Lys Lys Pro
                85                  90                  95 aag tat caa atg aaa gat tta tta cca tat gga aat gtg gga cgt gag      336
Lys Tyr Gln Met Lys Asp Leu Leu Pro Tyr Gly Asn Val Gly Arg Glu
            100                 105                 110 gca ttt ctg cat ttc ttg agc tat atc tac act ggg agg tta aag cct      384
Ala Phe Leu His Phe Leu Ser Tyr Ile Tyr Thr Gly Arg Leu Lys Pro
        115                 120                 125 ttt cct atc gag gtt tca act tgt gtt gat tca gtt tgt gct cat gat      432
Phe Pro Ile Glu Val Ser Thr Cys Val Asp Ser Val Cys Ala His Asp
    130                 135                 140 tct tgt aaa ccg gcc att gat ttt gct gtt gag ttg atg tat gct tca      480
Ser Cys Lys Pro Ala Ile Asp Phe Ala Val Glu Leu Met Tyr Ala Ser
145                 150                 155                 160 ttt gtg ttc caa atc ccg gat ctt gtt tcg tca ttt cag cgg aag ctt      528
Phe Val Phe Gln Ile Pro Asp Leu Val Ser Ser Phe Gln Arg Lys Leu
                165                 170                 175 cgt aac tat gtt gag aag tca cta gta gag aat gtt ctt cct atc ctc      576
Arg Asn Tyr Val Glu Lys Ser Leu Val Glu Asn Val Leu Pro Ile Leu
            180                 185                 190 tta gtt gcg ttt cat tgt gat ttg aca cag ctt ctt gat caa tgc att      624
Leu Val Ala Phe His Cys Asp Leu Thr Gln Leu Leu Asp Gln Cys Ile
        195                 200                 205 gag aga gtg gcg aga tca gac tta gac aga ttc tgt atc gaa aag gag      672
Glu Arg Val Ala Arg Ser Asp Leu Asp Arg Phe Cys Ile Glu Lys Glu
    210                 215                 220
```

```
ctt cct tta gaa gta ttg gaa aaa atc aaa cag ctt cga gtt aag tcg        720
Leu Pro Leu Glu Val Leu Glu Lys Ile Lys Gln Leu Arg Val Lys Ser
225                 230                 235                 240 gtg aac ata ccc gag gtg gag gat aaa tcg ata gag aga aca ggg aaa        768
Val Asn Ile Pro Glu Val Glu Asp Lys Ser Ile Glu Arg Thr Gly Lys
                245                 250                 255 gta ctc aag gca ttg gat tca gat gat gta gaa ctc gtg aag ctt ctt        816
Val Leu Lys Ala Leu Asp Ser Asp Asp Val Glu Leu Val Lys Leu Leu
            260                 265                 270 ttg act gag tca gat ata act cta gac caa gcc aat ggt cta cat tat        864
Leu Thr Glu Ser Asp Ile Thr Leu Asp Gln Ala Asn Gly Leu His Tyr
        275                 280                 285 gca gtg gca tac agt gat ccg aaa gtt gtg aca cag gtt ctt gat cta        912
Ala Val Ala Tyr Ser Asp Pro Lys Val Val Thr Gln Val Leu Asp Leu
    290                 295                 300 gat atg gct gat gtt aat ttc aga aat tcc agg ggg tat acg gtt ctt        960
Asp Met Ala Asp Val Asn Phe Arg Asn Ser Arg Gly Tyr Thr Val Leu
305                 310                 315                 320 cat att gct gct atg cgt aga gag cca aca att atc ata cca ctt att       1008
His Ile Ala Ala Met Arg Arg Glu Pro Thr Ile Ile Ile Pro Leu Ile
                325                 330                 335 caa aaa gga gct aat gct tca gat ttc acg ttt gat gga cgc agt gcg       1056
Gln Lys Gly Ala Asn Ala Ser Asp Phe Thr Phe Asp Gly Arg Ser Ala
            340                 345                 350 gta aat ata tgt agg aga ctc act agg ccg aaa gat tat cat acc aaa       1104
Val Asn Ile Cys Arg Arg Leu Thr Arg Pro Lys Asp Tyr His Thr Lys
        355                 360                 365 acc tca agg aaa gaa cct agt aaa tac cgc tta tgc atc gat atc ttg       1152
Thr Ser Arg Lys Glu Pro Ser Lys Tyr Arg Leu Cys Ile Asp Ile Leu
    370                 375                 380 gaa agg gaa att aga agg aat cca ttg gtt agt ggg gat aca ccc act       1200
Glu Arg Glu Ile Arg Arg Asn Pro Leu Val Ser Gly Asp Thr Pro Thr
385                 390                 395                 400 tgt tcc cat tcg atg ccc gag gat ctc caa atg agg ttg tta tac tta       1248
Cys Ser His Ser Met Pro Glu Asp Leu Gln Met Arg Leu Leu Tyr Leu
                405                 410                 415 gaa aag cga gtg gga ctt gct cag ttg ttc ttc cca gca gaa gcc aat       1296
Glu Lys Arg Val Gly Leu Ala Gln Leu Phe Phe Pro Ala Glu Ala Asn
            420                 425                 430 gtg gct atg gac gtt gct aat gtt gaa ggg aca agc gag tgc aca ggt       1344
Val Ala Met Asp Val Ala Asn Val Glu Gly Thr Ser Glu Cys Thr Gly
        435                 440                 445 ctt cta act cca cct cca tca aat gat aca act gaa aac ttg ggt aaa       1392
Leu Leu Thr Pro Pro Pro Ser Asn Asp Thr Thr Glu Asn Leu Gly Lys
    450                 455                 460 gtc gat tta aat gaa acg cct tat gtg caa acg aaa aga atg ctt aca       1440
Val Asp Leu Asn Glu Thr Pro Tyr Val Gln Thr Lys Arg Met Leu Thr
465                 470                 475                 480 cgt atg aaa gcc ctc atg aaa aca gtt gag aca ggt cgg aga tac ttc       1488
Arg Met Lys Ala Leu Met Lys Thr Val Glu Thr Gly Arg Arg Tyr Phe
                485                 490                 495 cca tct tgt tat gag gtt ctg gat aag tac atg gat cag tat atg gac       1536
Pro Ser Cys Tyr Glu Val Leu Asp Lys Tyr Met Asp Gln Tyr Met Asp
            500                 505                 510 gaa gaa atc cct gat atg tcg tat ccc gag aaa ggc act gtg aaa gag       1584
Glu Glu Ile Pro Asp Met Ser Tyr Pro Glu Lys Gly Thr Val Lys Glu
        515                 520                 525 aga aga cag aag agg atg aga tat aac gag ctg aag aac gac gtt aaa       1632
Arg Arg Gln Lys Arg Met Arg Tyr Asn Glu Leu Lys Asn Asp Val Lys
```

```
                        530                  535                  540
aaa gca tat agc aaa gac aaa gtc gcg cgg tct tgt ctt tct tct tca       1680
Lys Ala Tyr Ser Lys Asp Lys Val Ala Arg Ser Cys Leu Ser Ser Ser
545                 550                 555                 560 tca cca gct tct tct ctt aga gaa gcc tta gag aat cca aca tga           1725
Ser Pro Ala Ser Ser Leu Arg Glu Ala Leu Glu Asn Pro Thr
                565                 570                 575

<210> SEQ ID NO 70
<211> LENGTH: 574
<212> TYPE: PRT
<213> ORGANISM: Arabidopsis thaliana

<400> SEQUENCE: 70

Met Ala Ala Thr Ala Ile Glu Pro Ser Ser Ile Ser Phe Thr Ser
  1               5                  10                  15

Ser His Leu Ser Asn Pro Ser Pro Val Val Thr Thr Tyr His Ser Ala
                 20                  25                  30

Ala Asn Leu Glu Glu Leu Ser Ser Asn Leu Glu Gln Leu Leu Thr Asn
             35                  40                  45

Pro Asp Cys Asp Tyr Thr Asp Ala Glu Ile Ile Glu Glu Glu Ala
     50                  55                  60

Asn Pro Val Ser Val His Arg Cys Val Leu Ala Ala Arg Ser Lys Phe
 65                  70                  75                  80

Phe Leu Asp Leu Phe Lys Lys Asp Lys Asp Ser Ser Glu Lys Lys Pro
                 85                  90                  95

Lys Tyr Gln Met Lys Asp Leu Leu Pro Tyr Gly Asn Val Gly Arg Glu
                100                 105                 110

Ala Phe Leu His Phe Leu Ser Tyr Ile Tyr Thr Gly Arg Leu Lys Pro
            115                 120                 125

Phe Pro Ile Glu Val Ser Thr Cys Val Asp Ser Val Cys Ala His Asp
        130                 135                 140

Ser Cys Lys Pro Ala Ile Asp Phe Ala Val Glu Leu Met Tyr Ala Ser
145                 150                 155                 160

Phe Val Phe Gln Ile Pro Asp Leu Val Ser Ser Phe Gln Arg Lys Leu
                165                 170                 175

Arg Asn Tyr Val Glu Lys Ser Leu Val Glu Asn Val Leu Pro Ile Leu
                180                 185                 190

Leu Val Ala Phe His Cys Asp Leu Thr Gln Leu Leu Asp Gln Cys Ile
            195                 200                 205

Glu Arg Val Ala Arg Ser Asp Leu Asp Arg Phe Cys Ile Glu Lys Glu
        210                 215                 220

Leu Pro Leu Glu Val Leu Glu Lys Ile Lys Gln Leu Arg Val Lys Ser
225                 230                 235                 240

Val Asn Ile Pro Glu Val Glu Asp Lys Ser Ile Glu Arg Thr Gly Lys
                245                 250                 255

Val Leu Lys Ala Leu Asp Ser Asp Val Glu Leu Val Lys Leu Leu
                260                 265                 270

Leu Thr Glu Ser Asp Ile Thr Leu Asp Gln Ala Asn Gly Leu His Tyr
            275                 280                 285

Ala Val Ala Tyr Ser Asp Pro Lys Val Val Thr Gln Val Leu Asp Leu
        290                 295                 300

Asp Met Ala Asp Val Asn Phe Arg Asn Ser Arg Gly Tyr Thr Val Leu
305                 310                 315                 320

His Ile Ala Ala Met Arg Arg Glu Pro Thr Ile Ile Ile Pro Leu Ile
```

-continued

```
                        325                 330                 335
Gln Lys Gly Ala Asn Ala Ser Asp Phe Thr Phe Asp Gly Arg Ser Ala
                340                 345                 350
Val Asn Ile Cys Arg Arg Leu Thr Arg Pro Lys Asp Tyr His Thr Lys
            355                 360                 365
Thr Ser Arg Lys Glu Pro Ser Lys Tyr Arg Leu Cys Ile Asp Ile Leu
        370                 375                 380
Glu Arg Glu Ile Arg Arg Asn Pro Leu Val Ser Gly Asp Thr Pro Thr
385                 390                 395                 400
Cys Ser His Ser Met Pro Glu Asp Leu Gln Met Arg Leu Leu Tyr Leu
                405                 410                 415
Glu Lys Arg Val Gly Leu Ala Gln Leu Phe Phe Pro Ala Glu Ala Asn
            420                 425                 430
Val Ala Met Asp Val Ala Asn Val Glu Gly Thr Ser Glu Cys Thr Gly
        435                 440                 445
Leu Leu Thr Pro Pro Ser Asn Asp Thr Thr Glu Asn Leu Gly Lys
    450                 455                 460
Val Asp Leu Asn Glu Thr Pro Tyr Val Gln Thr Lys Arg Met Leu Thr
465                 470                 475                 480
Arg Met Lys Ala Leu Met Lys Thr Val Glu Thr Gly Arg Arg Tyr Phe
                485                 490                 495
Pro Ser Cys Tyr Glu Val Leu Asp Lys Tyr Met Asp Gln Tyr Met Asp
            500                 505                 510
Glu Glu Ile Pro Asp Met Ser Tyr Pro Glu Lys Gly Thr Val Lys Glu
        515                 520                 525
Arg Arg Gln Lys Arg Met Arg Tyr Asn Glu Leu Lys Asn Asp Val Lys
    530                 535                 540
Lys Ala Tyr Ser Lys Asp Lys Val Ala Arg Ser Cys Leu Ser Ser Ser
545                 550                 555                 560
Ser Pro Ala Ser Ser Leu Arg Glu Ala Leu Glu Asn Pro Thr
                565                 570
```

<210> SEQ ID NO 71
<211> LENGTH: 1818
<212> TYPE: DNA
<213> ORGANISM: Arabidopsis thaliana
<220> FEATURE:
<221> NAME/KEY: CDS
<222> LOCATION: (13)..(1818)
<223> OTHER INFORMATION: AtNMLc4-2 cDNA sequence

<400> SEQUENCE: 71

```
gccgatctcg tg atg atg gcc acc acc acc acc acc acc gct aga ttc       51
              Met Met Ala Thr Thr Thr Thr Thr Thr Thr Ala Arg Phe
               1               5                  10 tct gat tca tac gag ttc agc aac aca agc ggc aat agc ttc ttc gcc    99
Ser Asp Ser Tyr Glu Phe Ser Asn Thr Ser Gly Asn Ser Phe Phe Ala
 15                  20                  25 gcc gag tca tct ctt gat tat ccg acg gaa ttt ctc acg cca ccg gag   147
Ala Glu Ser Ser Leu Asp Tyr Pro Thr Glu Phe Leu Thr Pro Pro Glu
 30                  35                  40                  45 gta tca gct ctt aaa ctt ctg tct aac tgc ctc gag tct gtt ttc gac   195
Val Ser Ala Leu Lys Leu Leu Ser Asn Cys Leu Glu Ser Val Phe Asp
                 50                  55                  60 tcg ccg gag acg ttc tac agc gat gct aag cta gtt ctc gcc ggc ggc   243
Ser Pro Glu Thr Phe Tyr Ser Asp Ala Lys Leu Val Leu Ala Gly Gly
             65                  70                  75
```

```
cgg gaa gtt tct ttt cac cgt tgt att ctt tcc gcg aga att cct gtc      291
Arg Glu Val Ser Phe His Arg Cys Ile Leu Ser Ala Arg Ile Pro Val
        80                  85                  90 ttc aaa agc gct tta gcc acc gtg aag gaa caa aaa tcc tcc acc acc      339
Phe Lys Ser Ala Leu Ala Thr Val Lys Glu Gln Lys Ser Ser Thr Thr
    95                 100                 105 gtg aag ctc cag ctg aaa gag atc gcc aga gat tac gaa gtc ggc ttt      387
Val Lys Leu Gln Leu Lys Glu Ile Ala Arg Asp Tyr Glu Val Gly Phe
110                 115                 120                 125 gac tcg gtt gtg gcg gtt ttg gcg tat gtt tac agc ggc aga gtg agg      435
Asp Ser Val Val Ala Val Leu Ala Tyr Val Tyr Ser Gly Arg Val Arg
                130                 135                 140 tcc ccg ccg aag gga gct tct gct tgc gta gac gac gat tgt tgc cac      483
Ser Pro Pro Lys Gly Ala Ser Ala Cys Val Asp Asp Asp Cys Cys His
            145                 150                 155 gtg gct tgc cgg tca aag gtg gat ttc atg gtg gag gtt ctt tat ctg      531
Val Ala Cys Arg Ser Lys Val Asp Phe Met Val Glu Val Leu Tyr Leu
        160                 165                 170 tct ttc gtt ttc cag att caa gaa tta gtt act ctg tat gag agg cag      579
Ser Phe Val Phe Gln Ile Gln Glu Leu Val Thr Leu Tyr Glu Arg Gln
175                 180                 185 ttc ttg gaa att gta gac aaa gtt gta gtc gaa gac atc ttg gtt ata      627
Phe Leu Glu Ile Val Asp Lys Val Val Val Glu Asp Ile Leu Val Ile
190                 195                 200                 205 ttc aag ctt gat act cta tgt ggt aca aca tac aag aag ctt ttg gat      675
Phe Lys Leu Asp Thr Leu Cys Gly Thr Thr Tyr Lys Lys Leu Leu Asp
                210                 215                 220 aga tgc ata gaa att atc gtg aag tct gat ata gaa cta gtt agt ctt      723
Arg Cys Ile Glu Ile Ile Val Lys Ser Asp Ile Glu Leu Val Ser Leu
            225                 230                 235 gag aag tct tta cct caa cac att ttc aag caa atc ata gac atc cgc      771
Glu Lys Ser Leu Pro Gln His Ile Phe Lys Gln Ile Ile Asp Ile Arg
        240                 245                 250 gaa gcg ctc tgt cta gag cca cct aaa cta gaa agg cat gtc aag aac      819
Glu Ala Leu Cys Leu Glu Pro Pro Lys Leu Glu Arg His Val Lys Asn
255                 260                 265 ata tac aag gcg cta gac tca gat gat gtt gag ctt gtc aag atg ctt      867
Ile Tyr Lys Ala Leu Asp Ser Asp Asp Val Glu Leu Val Lys Met Leu
270                 275                 280                 285 ttg cta gaa gga cac acc aat ctc gat gag gcg tat gct ctt cat ttt      915
Leu Leu Glu Gly His Thr Asn Leu Asp Glu Ala Tyr Ala Leu His Phe
                290                 295                 300 gct atc gct cac tgc gct gtg aag acc gcg tat gat ctc ctc gag ctt      963
Ala Ile Ala His Cys Ala Val Lys Thr Ala Tyr Asp Leu Leu Glu Leu
            305                 310                 315 gag ctt gcg gat gtt aac ctt aga aat ccg agg gga tac act gtg ctt     1011
Glu Leu Ala Asp Val Asn Leu Arg Asn Pro Arg Gly Tyr Thr Val Leu
        320                 325                 330 cat gtt gct gcg atg cgg aag gag ccg aag ttg ata ata tct ttg tta     1059
His Val Ala Ala Met Arg Lys Glu Pro Lys Leu Ile Ile Ser Leu Leu
335                 340                 345 atg aaa ggg gca aat att tta gac aca aca ttg gat ggt aga acc gct     1107
Met Lys Gly Ala Asn Ile Leu Asp Thr Thr Leu Asp Gly Arg Thr Ala
350                 355                 360                 365 tta gtg att gta aaa cga ctc act aaa gcg gat gac tac aaa act agt     1155
Leu Val Ile Val Lys Arg Leu Thr Lys Ala Asp Asp Tyr Lys Thr Ser
                370                 375                 380 acg gag gac ggt acg cct tct ctg aaa ggc gga tta tgc ata gag gta     1203
Thr Glu Asp Gly Thr Pro Ser Leu Lys Gly Gly Leu Cys Ile Glu Val
            385                 390                 395
```

-continued

```
ctt gag cat gaa caa aaa cta gaa tat ttg tcg cct ata gag gct tca    1251
Leu Glu His Glu Gln Lys Leu Glu Tyr Leu Ser Pro Ile Glu Ala Ser
        400                 405                 410 ctt tct ctt cca gta act cca gag gag ttg agg atg agg ttg ctc tat    1299
Leu Ser Leu Pro Val Thr Pro Glu Glu Leu Arg Met Arg Leu Leu Tyr
    415                 420                 425 tat gaa aac cga gtt gca ctt gct cga ctt ctc ttt cca gtg gaa act    1347
Tyr Glu Asn Arg Val Ala Leu Ala Arg Leu Leu Phe Pro Val Glu Thr
430                 435                 440                 445 gaa act gta cag ggt att gcc aaa ttg gag gaa aca tgc gag ttt aca    1395
Glu Thr Val Gln Gly Ile Ala Lys Leu Glu Glu Thr Cys Glu Phe Thr
                450                 455                 460 gct tct agt ctc gag cct gat cat cac att ggt gaa aag cgg aca tca    1443
Ala Ser Ser Leu Glu Pro Asp His His Ile Gly Glu Lys Arg Thr Ser
            465                 470                 475 cta gac cta aat atg gcg ccg ttc caa atc cat gag aag cat ttg agt    1491
Leu Asp Leu Asn Met Ala Pro Phe Gln Ile His Glu Lys His Leu Ser
        480                 485                 490 aga cta aga gca ctt tgt aaa acc gtg gaa ctg ggg aaa cgc tac ttc    1539
Arg Leu Arg Ala Leu Cys Lys Thr Val Glu Leu Gly Lys Arg Tyr Phe
    495                 500                 505 aaa cga tgt tcg ctt gat cac ttt atg gat act gag gac ttg aat cat    1587
Lys Arg Cys Ser Leu Asp His Phe Met Asp Thr Glu Asp Leu Asn His
510                 515                 520                 525 ctt gct agc gta gaa gaa gat act cct gag aaa cgg cta caa aag aag    1635
Leu Ala Ser Val Glu Glu Asp Thr Pro Glu Lys Arg Leu Gln Lys Lys
                530                 535                 540 caa agg tac atg gaa cta caa gag act ctg atg aag acc ttt agt gag    1683
Gln Arg Tyr Met Glu Leu Gln Glu Thr Leu Met Lys Thr Phe Ser Glu
            545                 550                 555 gac aag gag gaa tgt gga aag tct tcc aca ccg aaa cca acc tct gcg    1731
Asp Lys Glu Glu Cys Gly Lys Ser Ser Thr Pro Lys Pro Thr Ser Ala
        560                 565                 570 gtg agg tct aat aga aaa ctc tct cac cgg cgc cta aaa gtg gac aaa    1779
Val Arg Ser Asn Arg Lys Leu Ser His Arg Arg Leu Lys Val Asp Lys
    575                 580                 585 cgg gat ttt ttg aaa cga cct tac ggg aac ggg gat taa                1818
Arg Asp Phe Leu Lys Arg Pro Tyr Gly Asn Gly Asp
590                 595                 600
```

<210> SEQ ID NO 72
<211> LENGTH: 601
<212> TYPE: PRT
<213> ORGANISM: Arabidopsis thaliana

<400> SEQUENCE: 72

```
Met Met Ala Thr Thr Thr Thr Thr Thr Ala Arg Phe Ser Asp Ser
 1               5                  10                  15

Tyr Glu Phe Ser Asn Thr Ser Gly Asn Ser Phe Ala Ala Glu Ser
                20                  25                  30

Ser Leu Asp Tyr Pro Thr Glu Phe Leu Thr Pro Glu Val Ser Ala
            35                  40                  45

Leu Lys Leu Leu Ser Asn Cys Leu Glu Ser Val Phe Asp Ser Pro Glu
    50                  55                  60

Thr Phe Tyr Ser Asp Ala Lys Leu Val Leu Ala Gly Gly Arg Glu Val
65                  70                  75                  80

Ser Phe His Arg Cys Ile Leu Ser Ala Arg Ile Pro Val Phe Lys Ser
                85                  90                  95
```

```
Ala Leu Ala Thr Val Lys Glu Gln Lys Ser Ser Thr Val Lys Leu
                100                 105                 110

Gln Leu Lys Glu Ile Ala Arg Asp Tyr Glu Val Gly Phe Asp Ser Val
            115                 120                 125

Val Ala Val Leu Ala Tyr Val Tyr Ser Gly Arg Val Arg Ser Pro Pro
        130                 135                 140

Lys Gly Ala Ser Ala Cys Val Asp Asp Cys Cys His Val Ala Cys
145                 150                 155                 160

Arg Ser Lys Val Asp Phe Met Val Glu Val Leu Tyr Leu Ser Phe Val
                165                 170                 175

Phe Gln Ile Gln Glu Leu Val Thr Leu Tyr Glu Arg Gln Phe Leu Glu
            180                 185                 190

Ile Val Asp Lys Val Val Glu Asp Ile Leu Val Ile Phe Lys Leu
        195                 200                 205

Asp Thr Leu Cys Gly Thr Thr Tyr Lys Lys Leu Leu Asp Arg Cys Ile
        210                 215                 220

Glu Ile Ile Val Lys Ser Asp Ile Glu Leu Val Ser Leu Glu Lys Ser
225                 230                 235                 240

Leu Pro Gln His Ile Phe Lys Gln Ile Ile Asp Ile Arg Glu Ala Leu
                245                 250                 255

Cys Leu Glu Pro Pro Lys Leu Glu Arg His Val Lys Asn Ile Tyr Lys
            260                 265                 270

Ala Leu Asp Ser Asp Asp Val Glu Leu Val Lys Met Leu Leu Leu Glu
        275                 280                 285

Gly His Thr Asn Leu Asp Glu Ala Tyr Ala Leu His Phe Ala Ile Ala
        290                 295                 300

His Cys Ala Val Lys Thr Ala Tyr Asp Leu Leu Glu Leu Glu Leu Ala
305                 310                 315                 320

Asp Val Asn Leu Arg Asn Pro Arg Gly Tyr Thr Val Leu His Val Ala
                325                 330                 335

Ala Met Arg Lys Glu Pro Lys Leu Ile Ile Ser Leu Leu Met Lys Gly
            340                 345                 350

Ala Asn Ile Leu Asp Thr Thr Leu Asp Gly Arg Thr Ala Leu Val Ile
        355                 360                 365

Val Lys Arg Leu Thr Lys Ala Asp Asp Tyr Lys Thr Ser Thr Glu Asp
    370                 375                 380

Gly Thr Pro Ser Leu Lys Gly Gly Leu Cys Ile Glu Val Leu Glu His
385                 390                 395                 400

Glu Gln Lys Leu Glu Tyr Leu Ser Pro Ile Glu Ala Ser Leu Ser Leu
                405                 410                 415

Pro Val Thr Pro Glu Glu Leu Arg Met Arg Leu Leu Tyr Tyr Glu Asn
            420                 425                 430

Arg Val Ala Leu Ala Arg Leu Leu Phe Pro Val Glu Thr Glu Thr Val
        435                 440                 445

Gln Gly Ile Ala Lys Leu Glu Glu Thr Cys Glu Phe Thr Ala Ser Ser
    450                 455                 460

Leu Glu Pro Asp His His Ile Gly Glu Lys Arg Thr Ser Leu Asp Leu
465                 470                 475                 480

Asn Met Ala Pro Phe Gln Ile His Glu Lys His Leu Ser Arg Leu Arg
                485                 490                 495

Ala Leu Cys Lys Thr Val Glu Leu Gly Lys Arg Tyr Phe Lys Arg Cys
            500                 505                 510

Ser Leu Asp His Phe Met Asp Thr Glu Asp Leu Asn His Leu Ala Ser
```

-continued

```
              515                 520                 525
Val Glu Glu Asp Thr Pro Glu Lys Arg Leu Gln Lys Lys Gln Arg Tyr
            530                 535                 540

Met Glu Leu Gln Glu Thr Leu Met Lys Thr Phe Ser Glu Asp Lys Glu
545                 550                 555                 560

Glu Cys Gly Lys Ser Ser Thr Pro Lys Pro Thr Ser Ala Val Arg Ser
                565                 570                 575

Asn Arg Lys Leu Ser His Arg Arg Leu Lys Val Asp Lys Arg Asp Phe
            580                 585                 590

Leu Lys Arg Pro Tyr Gly Asn Gly Asp
            595                 600
```

<210> SEQ ID NO 73
<211> LENGTH: 2673
<212> TYPE: DNA
<213> ORGANISM: Nicotiana tabacum
<220> FEATURE:
<221> NAME/KEY: CDS
<222> LOCATION: (661)..(1767)
<223> OTHER INFORMATION: full-length Tobacco B cDNA sequence
<220> FEATURE:
<221> NAME/KEY: misc_feature
<222> LOCATION: (1)..(2673)
<223> OTHER INFORMATION: n = a, t, c or g

<400> SEQUENCE: 73

```
tcgagcggcc gcccgggcag gtaaactcta acccttttaa tcttttttg gttgcatttc     60 ggatctaacc tcaggaaaaa aaacagtatt tttagcctct gcaattgcaa attttctcgt   120
ttttttagcc gaagtgaatg ttattccaat tgggtaagct gtgatcaagc agttgaagtt   180
ttttgttgca aaatttgcca gttatcttga ctttttgtga agttggtaaa ttttttcattt   240 gggtaagttg tgatcaagca gttgaagatt tgcactttgt attcttactg tgaaattgca   300
gttttgttga ttatagatgg ggtggaattg ttaatttctt ctaaagtttt aaagggttga   360
tttggtttta cctgaaatag ggagaatatg acttgtagtt ttggaatttg cttcttttct   420
tggtctgcat agttgaatgt tattagaaaa cttatggaaa gttttggtca aacttttgtc   480
ctttgagaag aatttcttgt attggtgatt ggttatggtc ttggagaggt tcttttttt    540 tttgcataga gcctgtgcgg agaatattat acatggttaa aaacattaga ttttctggac   600
tttgactatc ttagatgtag ataaattttg tatatgtttt tagaccatta gaattgggaa   660 atg gct tgt tct gct gaa cca tca tca tct ata agc ttt act tca tct   708
Met Ala Cys Ser Ala Glu Pro Ser Ser Ser Ile Ser Phe Thr Ser Ser
  1               5                  10                  15 tcc att aca tcg aat ggg tcg att ggc gtt ggc caa aac act cat gct   756
Ser Ile Thr Ser Asn Gly Ser Ile Gly Val Gly Gln Asn Thr His Ala
             20                  25                  30 tat ggc ggc tct gag aca ggg agt agt tat gaa atc atc agc ttg agt   804
Tyr Gly Gly Ser Glu Thr Gly Ser Ser Tyr Glu Ile Ile Ser Leu Ser
         35                  40                  45 aaa ctc agt aac aat tta gag caa ctc ttg tca gat tcc agc tct gat   852
Lys Leu Ser Asn Asn Leu Glu Gln Leu Leu Ser Asp Ser Ser Ser Asp
     50                  55                  60 ttt act gat gct gag att gtt gtt gag ggt gtt tca ctt ggt gtt cac   900
Phe Thr Asp Ala Glu Ile Val Val Glu Gly Val Ser Leu Gly Val His
 65                  70                  75                  80 cgt tgt ata tta gct gcc agg agt aaa ttt ttt cag gat ctt ttt agg   948
Arg Cys Ile Leu Ala Ala Arg Ser Lys Phe Phe Gln Asp Leu Phe Arg
                 85                  90                  95
```

```
aaa gag aag gga agt tgt gga aag gaa ggt aaa cca aga tat tct atg      996
Lys Glu Lys Gly Ser Cys Gly Lys Glu Gly Lys Pro Arg Tyr Ser Met
            100                 105                 110 acc gat att ttg cct tat ggt aag gtt gga tat gag gct ttc gtt acc     1044
Thr Asp Ile Leu Pro Tyr Gly Lys Val Gly Tyr Glu Ala Phe Val Thr
        115                 120                 125 ttc cta agc tat ttg tac tca gga aaa ttg aag cat ttc cct ccg gag     1092
Phe Leu Ser Tyr Leu Tyr Ser Gly Lys Leu Lys His Phe Pro Pro Glu
    130                 135                 140 gta tca aca tgt atg gac act ata tgt gct cat gac tct tgc aga cca     1140
Val Ser Thr Cys Met Asp Thr Ile Cys Ala His Asp Ser Cys Arg Pro
145                 150                 155                 160 gca att aat ttt agt gtg gag ttg atg tat gcc tct tcc atg ttt cag     1188
Ala Ile Asn Phe Ser Val Glu Leu Met Tyr Ala Ser Ser Met Phe Gln
                165                 170                 175 gtt cca gag cta gta tca ctt ttc ctg aga cgc ctt atc aat ttt gtt     1236
Val Pro Glu Leu Val Ser Leu Phe Leu Arg Arg Leu Ile Asn Phe Val
            180                 185                 190 ggg aag gct ctt gtg gaa gat gtt atc cca ata ctt aga gtt gct ttt     1284
Gly Lys Ala Leu Val Glu Asp Val Ile Pro Ile Leu Arg Val Ala Phe
        195                 200                 205 cat tgc caa ttg agc gag ctt ctc act cat tcc gtt gat aga gta gca     1332
His Cys Gln Leu Ser Glu Leu Leu Thr His Ser Val Asp Arg Val Ala
    210                 215                 220 cga tca gat ctt gaa atc aca tgc att gag aaa gag gtt ccc ttt gaa     1380
Arg Ser Asp Leu Glu Ile Thr Cys Ile Glu Lys Glu Val Pro Phe Glu
225                 230                 235                 240 gtt gca gag aat att aaa tta ttg tgg ccg aaa tgt cag gtt gat gaa     1428
Val Ala Glu Asn Ile Lys Leu Leu Trp Pro Lys Cys Gln Val Asp Glu
                245                 250                 255 agt aag gtt cta cct gtg gat ccc ttg cat gaa aag aga aaa aat agg     1476
Ser Lys Val Leu Pro Val Asp Pro Leu His Glu Lys Arg Lys Asn Arg
            260                 265                 270 ata tac aag gca ttg gat tcg gat gat gtt gaa ctt gtc aag ctt cta     1524
Ile Tyr Lys Ala Leu Asp Ser Asp Asp Val Glu Leu Val Lys Leu Leu
        275                 280                 285 ctg agt gag tct aac ata agc tta gat gaa gcc tac gct ctt cat tat     1572
Leu Ser Glu Ser Asn Ile Ser Leu Asp Glu Ala Tyr Ala Leu His Tyr
    290                 295                 300 gct gtg gca tat tgt gat ccc aag gtt gtg act gag gtt ctt gga ctg     1620
Ala Val Ala Tyr Cys Asp Pro Lys Val Val Thr Glu Val Leu Gly Leu
305                 310                 315                 320 ggt gtt gcg gat gtc aac cta cgt aat act cgt ggt tac act gtg ctt     1668
Gly Val Ala Asp Val Asn Leu Arg Asn Thr Arg Gly Tyr Thr Val Leu
                325                 330                 335 cac att gct tcc atg cgt aag gag cca gca gta att gta tcg ctt ttg     1716
His Ile Ala Ser Met Arg Lys Glu Pro Ala Val Ile Val Ser Leu Leu
            340                 345                 350 act aag gga gct cgt gca tca gag act aca ttg gat ggg cag agt gct     1764
Thr Lys Gly Ala Arg Ala Ser Glu Thr Thr Leu Asp Gly Gln Ser Ala
        355                 360                 365 gtt agtatctgta ggaggctgac taggcctaag gagtaccatg caaaaacaga          1817
Val acaaggccag gaagcaaaca aagatcgggt atgtattgat gttttggaga gagagatgcg   1877
tcgcaaccca atggctggag atgcattgtt ttcttcccca atgttggccg atgatctgca   1937
catgaaactg cactacctgg aaaatagagt ggcatttgca cggttactgt tccctcttga   1997
agccagacta gccatgcaaa ttgcaaatgc tgagactgca gctgaagtag cagtccgttt   2057
```

-continued

```
ggcatctaaa agtacatctg ggaacttgag ggaggttgat ttgaatgaga cacccataaa    2117
gcagaaagaa agacttcttt caaggatgca agccctctcg aagacagttg aacttggcaa    2177
gcgctatttt ccacattgct ctcaagttct ggacaagttt atggaggatg acttacccga    2237
cttaattttc cttgagatgg gccctccaga ggagcaaaag atcaagagga agcgatttaa    2297
ggagctcaaa gatgacgttc ancgggcatt taacaaagac aaagctgaac ttcattgctc    2357
ccgcttgtcc tcatcatcat gttcctcttc ttttaaagat ggngcaagtg tcaaacttag    2417
gaaactatga gtaaataggg ttttgtccta tagtttctct nccatctcag ttttgaatgt    2477
aagattaata gttttataa agacttgtct tgtacancct tcattagagc gcctgctttg    2537
tcgctatcca tttccctatt cagcttgtta aacttccatg tttncagtag aaagaaattt    2597
gcttaggaac aagcttttgg aatagcttat atggaaaatt gattgtaaaa aaaaaaaaa    2657 aaaaaaaaaa aaaaa    2673
```

<210> SEQ ID NO 74
<211> LENGTH: 369
<212> TYPE: PRT
<213> ORGANISM: Nicotiana tabacum

<400> SEQUENCE: 74

```
Met Ala Cys Ser Ala Glu Pro Ser Ser Ser Ile Ser Phe Thr Ser Ser
 1               5                  10                  15

Ser Ile Thr Ser Asn Gly Ser Ile Gly Val Gly Gln Asn Thr His Ala
            20                  25                  30

Tyr Gly Gly Ser Glu Thr Gly Ser Ser Tyr Glu Ile Ile Ser Leu Ser
        35                  40                  45

Lys Leu Ser Asn Asn Leu Glu Gln Leu Leu Ser Asp Ser Ser Ser Asp
    50                  55                  60

Phe Thr Asp Ala Glu Ile Val Val Glu Gly Val Ser Leu Gly Val His
65                  70                  75                  80

Arg Cys Ile Leu Ala Ala Arg Ser Lys Phe Phe Gln Asp Leu Phe Arg
                85                  90                  95

Lys Glu Lys Gly Ser Cys Gly Lys Glu Gly Lys Pro Arg Tyr Ser Met
            100                 105                 110

Thr Asp Ile Leu Pro Tyr Gly Lys Val Gly Tyr Glu Ala Phe Val Thr
        115                 120                 125

Phe Leu Ser Tyr Leu Tyr Ser Gly Lys Leu Lys His Phe Pro Pro Glu
    130                 135                 140

Val Ser Thr Cys Met Asp Thr Ile Cys Ala His Asp Ser Cys Arg Pro
145                 150                 155                 160

Ala Ile Asn Phe Ser Val Glu Leu Met Tyr Ala Ser Ser Met Phe Gln
                165                 170                 175

Val Pro Glu Leu Val Ser Leu Phe Leu Arg Arg Leu Ile Asn Phe Val
            180                 185                 190

Gly Lys Ala Leu Val Glu Asp Val Ile Pro Ile Leu Arg Val Ala Phe
        195                 200                 205

His Cys Gln Leu Ser Glu Leu Leu Thr His Ser Val Asp Arg Val Ala
    210                 215                 220

Arg Ser Asp Leu Glu Ile Thr Cys Ile Glu Lys Glu Val Pro Phe Glu
225                 230                 235                 240

Val Ala Glu Asn Ile Lys Leu Leu Trp Pro Lys Cys Gln Val Asp Glu
                245                 250                 255
```

```
Ser Lys Val Leu Pro Val Asp Pro Leu His Glu Lys Arg Lys Asn Arg
        260             265             270

Ile Tyr Lys Ala Leu Asp Ser Asp Asp Val Glu Leu Val Lys Leu Leu
        275             280             285

Leu Ser Glu Ser Asn Ile Ser Leu Asp Glu Ala Tyr Ala Leu His Tyr
        290             295             300

Ala Val Ala Tyr Cys Asp Pro Lys Val Val Thr Glu Val Leu Gly Leu
305             310             315                         320

Gly Val Ala Asp Val Asn Leu Arg Asn Thr Arg Gly Tyr Thr Val Leu
                325             330                 335

His Ile Ala Ser Met Arg Lys Glu Pro Ala Val Ile Val Ser Leu Leu
            340             345             350

Thr Lys Gly Ala Arg Ala Ser Glu Thr Thr Leu Asp Gly Gln Ser Ala
        355             360             365

Val
```

PLANT GENES AND USES THEREOF

This application claims the benefit of U.S. Provisional Application No. 60/219,338, filed Mar. 9, 1999, the disclosure of which is hereby incorporated by reference in its entirety.

FIELD OF THE INVENTION

The present invention relates to broad-spectrum disease resistance in plants, including the phenomenon of systemic acquired resistance (SAR). More particularly, the present invention relates to the identification, isolation and characterization of homologues of the Arabidopsis NIM1 gene involved in the signal transduction cascade leading to systemic acquired resistance in plants.

BACKGROUND OF THE INVENTION

Plants are constantly challenged by a wide variety of pathogenic organisms including viruses, bacteria, fungi, and nematodes. Crop plants are particularly vulnerable because they are usually grown as genetically-uniform monocultures; when disease strikes, losses can be severe. However, most plants have their own innate mechanisms of defense against pathogenic organisms. Natural variation for resistance to plant pathogens has been identified by plant breeders and pathologists and bred into many crop plants. These natural disease resistance genes often provide high levels of resistance to or immunity against pathogens.

Systemic acquired resistance (SAR) is one component of the complex system plants use to defend themselves from pathogens (Hunt and Ryals, 1996; Ryals et al., 1996). See also, U.S. Pat. No. 5,614,395. SAR is a particularly important aspect of plant-pathogen responses because it is a pathogen-inducible, systemic resistance against a broad spectrum of infectious agents, including viruses, bacteria, and fungi. When the SAR signal transduction pathway is blocked, plants become more susceptible to pathogens that normally cause disease, and they also become susceptible to some infectious agents that would not normally cause disease (Gaffney et al., 1993; Delaney et al., 1994; Delaney et al., 1995; Delaney, 1997; Bi et al., 1995; Mauch-Mani and Slusarenko, 1996). These observations indicate that the SAR signal transduction pathway is critical for maintaining plant health.

Conceptually, the SAR response can be divided into two phases. In the initiation phase, a pathogen infection is recognized, and a signal is released that travels through the phloem to distant tissues. This systemic signal is perceived by target cells, which react by expression of both SAR genes and disease resistance. The maintenance phase of SAR refers to the period of time, from weeks up to the entire life of the plant, during which the plant is in a quasi steady state, and disease resistance is maintained (Ryals et al., 1996).

Salicylic acid (SA) accumulation appears to be required for SAR signal transduction. Plants that cannot accumulate SA due to treatment with specific inhibitors, epigenetic repression of phenylalanine ammonia-lyase, or transgenic expression of salicylate hydroxylase, which specifically degrades SA, also cannot induce either SAR gene expression or disease resistance (Gaffney et al., 1993; Delaney et al., 1994; Mauch-Mani and Slusarenko, 1996; Maher et al., 1994; Pallas et al., 1996). Although it has been suggested that SA might serve as the systemic signal, this is currently controversial and, to date, all that is known for certain is that if SA cannot accumulate, then SAR signal transduction is blocked (Pallas et al., 1996; Shulaev et al., 1995; Vernooij et al., 1994).

Recently, Arabidopsis has emerged as a model system to study SAR (Uknes et al., 1992; Uknes et al., 1993; Cameron et al., 1994; Mauch-Mani and Slusarenko, 1994; Dempsey and Klessig, 1995). It has been demonstrated that SAR can be activated in Arabidopsis by both pathogens and chemicals, such as SA, 2,6-dichloroisonicotinic acid (INA) and benzo(1,2,3)thiadiazole-7-carbothioic acid S-methyl ester (BTH) (Uknes et al., 1992; Vernooij et al., 1995; Lawton et al., 1996). Following treatment with either INA or BTH or pathogen infection, at least three pathogenesis-related (PR) protein genes, namely, PR-1, PR-2, and PR-5 are coordinately induced concomitant with the onset of resistance (Uknes et al., 1992, 1993). In tobacco, the best characterized species, treatment with a pathogen or an immunization compound induces the expression of at least nine sets of genes (Ward et al., 1991). Transgenic disease-resistant plants have been created by transforming plants with various SAR genes (U.S. Pat. No. 5,614,395).

A number of Arabidopsis mutants have been isolated that have modified SAR signal transduction (Delaney, 1997) The first of these mutants are the so-called lsd (lesions simulating disease) mutants and acd2 (accelerated cell death) (Dietrich et al., 1994; Greenberg et al., 1994). These mutants all have some degree of spontaneous necrotic lesion formation on their leaves, elevated levels of SA, mRNA accumulation for the SAR genes, and significantly enhanced disease resistance. At least seven different lsd mutants have been isolated and characterized (Dietrich et al., 1994; Weymann et al., 1995). Another interesting class of mutants are cim (constitutive immunity) mutants (Lawton et al., 1993). See also, U.S. Pat. No. 5,792,904 and International PCT Application WO 94/16077. Like lsd mutants and acd2, cim mutants have elevated SA and SAR gene expression and resistance, but in contrast to lsd or acd2, do not display detectable lesions on their leaves. cpr1 (constitutive expresser of PR genes) may be a type of cim mutant; however, because the presence of microscopic lesions on the leaves of cpr1 has not been ruled out, cpr1 might be a type of lsd mutant (Bowling et al., 1994).

Mutants have also been isolated that are blocked in SAR signaling. ndr1 (non-race-specific disease resistance) is a mutant that allows growth of both *Pseudomonas syringae* containing various avirulence genes and also normally avirulent isolates of *Peronospora parasitica* (Century et al., 1995). Apparently this mutant is blocked early in SAR signaling. npr1 (nonexpresser of PR genes) is a mutant that cannot induce expression of the SAR signaling pathway following INA treatment (Cao et al., 1994). eds (enhanced disease susceptibility) mutants have been isolated based on their ability to support bacterial infection following inoculation of a low bacterial concentration (Glazebrook et al., 1996; Parker et al., 1996). Certain eds mutants are phenotypically very similar to npr1, and, recently, eds5 and eds53 have been shown to be allelic to npr1 (Glazebrook et al., 1996). nim1 (noninducible immunity) is a mutant that supports *P. parasitica* (i.e., causal agent of downy mildew disease) growth following INA treatment (Delaney et al., 1995; U.S. Pat. No. 5,792,904). Although nim1 can accumulate SA following pathogen infection, it cannot induce SAR gene expression or disease resistance, suggesting that the mutation blocks the pathway downstream of SA. nim1 is also impaired in its ability to respond to INA or BTH, suggesting that the block exists downstream of the action of these chemicals (Delaney et al., 1995; Lawton et al., 1996).

Allelic Arabidopsis genes have been isolated and characterized, mutants of which are responsible for the nim1 and npr1 phenotypes, respectively (Ryals et al., 1997; Cao et al., 1997). The wild-type NIM1 gene product is involved in the signal transduction cascade leading to both SAR and gene-for-gene disease resistance in Arabidopsis (Ryals et al., 1997). Ryals et al., 1997 also report the isolation of five additional alleles of nim1 that show a range of phenotypes from weakly impaired in chemically induced PR-1 gene expression and fungal resistance to very strongly blocked. Transformation of the wild-type NPR1 gene into npr1 mutants not only complemented the mutations, restoring the responsiveness of SAR induction with respect to PR-gene expression and disease resistance, but also rendered the transgenic plants more resistant to infection by *P. syringae* in the absence of SAR induction (Cao et al., 1997). WO 98/06748 describes the isolation of NPR1 from Arabidopsis and a homologue from *Nicotiana glutinosa.* See also, WO 97/49822, WO 98/26082, and WO 98/29537.

Despite much research and the use of sophisticated and intensive crop protection measures, including genetic transformation of plants, losses due to disease remain in the billions of dollars annually. Therefore, there is a continuing need to develop new crop protection measures based on the ever-increasing understanding of the genetic basis for disease resistance in plants. In particular, there is a need for the identification, isolation, and characterization of homologues of the Arabidopsis NIM1 gene from additional species of plants.

SUMMARY OF THE INVENTION

The present invention addresses the aforementioned needs by providing several homologues of the Arabidopsis NIM1 gene from additional species of plants. In particular, the present invention concerns the isolation of *Nicotiana tabacum* (tobacco), *Lycopersicon esculentum* (tomato), *Brassica napus* (oilseed rape), *Arabidopsis thaliana*, *Beta vulgaris* (sugarbeet), *Helianthus annuus* (sunflower), and *Solanum tuberosum* (potato) homologues of the NIM1 gene, which encode proteins believed to be involved in the signal transduction cascade responsive to biological and chemical inducers that lead to systemic acquired resistance in plants.

Hence, the present invention is directed to an isolated nucleic acid molecule comprising a nucleotide sequence that encodes SEQ ID NO:2, 4, 6, 8, 16, 18, 20, 30, 32, 34, 36, 38, 40, 42, 44, 46, 48, 50, 52, 54, 56, 58, 62, 64, 66, 68, 70, 72, or 74.

In another embodiment, the present invention is directed to an isolated nucleic acid molecule comprising SEQ ID NO:1, 3, 5, 7, 15, 17, 19, 29, 31, 33, 35, 37, 39, 41, 43, 45, 47, 49, 51, 53, 55, 57, 61, 63, 65, 67, 69, 71, or 73.

In a further embodiment, the present invention is directed to an isolated nucleic acid molecule comprising a nucleotide sequence that comprises an at least 20, 25, 30, 35, 40, 45, or 50 (preferably 20) consecutive base pair portion identical in sequence to an at least 20, 25, 30, 35, 40, 45, or 50 (preferably 20) consecutive base pair portion of SEQ ID NO:1, 3, 5, 7, 15, 17, 19, 29, 31, 33, 35, 37, 39, 41, 43, 45, 47, 49, 51, 53, 55, 57, 61, 63, 65, 67, 69, 71, or 73.

In still another embodiment, the present invention is directed to an isolated nucleic acid molecule comprising a nucleotide sequence that can be amplified from a *Lycopersicon esculentum* DNA library using the polymerase chain reaction with the pair of primers set forth as SEQ ID NO:9 and 10, SEQ ID NO:21 and 24, SEQ ID NO:22 and 24, SEQ ID NO:25 and 28, SEQ ID NO:26 and 28, or SEQ ID NO:59 and 60.

In yet another embodiment, the present invention is directed to an isolated nucleic acid molecule comprising a nucleotide sequence that can be amplified from a *Beta vulgaris* DNA library using the polymerase chain reaction with the pair of primers set forth as SEQ ID NO:22 and 24 or SEQ ID NO:26 and 28.

In a further embodiment, the present invention is directed to an isolated nucleic acid molecule comprising a nucleotide sequence that can be amplified from a *Helianthus annuus* DNA library using the polymerase chain reaction with the pair of primers set forth as SEQ ID NO:26 and 28.

In another embodiment, the present invention is directed to an isolated nucleic acid molecule comprising a nucleotide sequence that can be amplified from a *Solanum tuberosum* DNA library using the polymerase chain reaction with the pair of primers set forth as SEQ ID NO:21 and 24, SEQ ID NO:21 and 23, SEQ ID NO:22 and 24, SEQ ID NO:25 and 28, or SEQ ID NO:26 and 28.

In a further embodiment, the present invention is directed to an isolated nucleic acid molecule comprising a nucleotide sequence that can be amplified from a *Brassica napus* DNA library using the polymerase chain reaction with the pair of primers set forth as SEQ ID NO:9 and 10 or SEQ ID NO:26 and 28.

In yet another embodiment, the present invention is directed to an isolated nucleic acid molecule comprising a nucleotide sequence that can be amplified from an *Arabidopsis thaliana* DNA library using the polymerase chain reaction with the pair of primers set forth as SEQ ID NO:13 and 14, SEQ ID NO:21 and 24, or SEQ ID NO:22 and 24.

In a further embodiment, the present invention is directed to an isolated nucleic acid molecule comprising a nucleotide sequence that can be amplified from an *Nicotiana tabacum* DNA library using the polymerase chain reaction with the pair of primers set forth as SEQ ID NO:9 and 10, SEQ ID NO:11 and 12, SEQ ID NO:21 and 24, SEQ ID NO:22 and 24, SEQ ID NO:25 and 28, or SEQ ID NO:26 and 28; or In a further embodiment, the present invention is directed to an isolated nucleic acid molecule comprising a nucleotide sequence that can be amplified from an plant DNA library using the polymerase chain reaction with a pair of primers comprising the first 20 nucleotides and the reverse complement of the last 20 nucleotides of the coding sequence (CDS) of SEQ ID NO:1, 3, 5, 7, 15, 17, 19, 29, 31, 33, 35, 37, 39, 41, 43, 45, 47, 49, 51, 53, 55, 57, 61, 63, 65, 67, 69, 71, or 73.

The present invention also encompasses a chimeric gene comprising a promoter active in plants operatively linked to a NIM1 homologue coding sequence of the present invention, a recombinant vector comprising such a chimeric gene, wherein the vector is capable of being stably transformed into a host, as well as a host stably transformed with such a vector. Preferably, the host is a plant such as one of the following agronomically important crops: rice, wheat, barley, rye, canola, sugarcane, corn, potato, carrot, sweet potato, sugar beet, bean, pea, chicory, lettuce, cabbage, cauliflower, broccoli, turnip, radish, spinach, asparagus, onion, garlic, eggplant, pepper, celery, squash, pumpkin, cucumber, apple, pear, quince, melon, plum, cherry, peach, nectarine, apricot, strawberry, grape, raspberry, blackberry, pineapple, avocado, papaya, mango, banana, soybean, tobacco, tomato, sorghum, and sugarcane. The present invention also encompasses seed from a plant of the invention.

Further, the present invention is directed to a method of increasing SAR gene expression in a plant by expressing in the plant a chimeric gene that itself comprises a promoter active in plants operatively linked to a NIM1 homologue coding sequence of the present invention, wherein the encoded protein is expressed in the transformed plant at higher levels than in a wild type plant.

In addition, the present invention is directed to a method of enhancing disease resistance in a plant by expressing in the plant a chimeric gene that itself comprises a promoter active in plants operatively linked to a NIM1 homologue coding sequence of the present invention, wherein the encoded protein is expressed in the transformed plant at higher levels than in a wild type plant.

Further, the present invention is directed to a PCR primer selected from the group consisting of SEQ ID NO:9–14, 21–28, 59, and 60.

The present invention also encompasses a method for isolating a NIM1 homologue involved in the signal transduction cascade leading to systemic acquired resistance in plants comprising amplifying a DNA molecule from a plant DNA library using the polymerase chain reaction with a pair of primers corresponding to the first 20 nucleotides and the reverse complement of the last 20 nucleotides of the coding sequence (CDS) of SEQ ID NO:1, 3, 5, 7, 15, 17, 19, 29, 31, 33, 35, 37, 39, 41, 43, 45, 47, 49, 51, 53, 55, 57, 61, 63, 65, 67, 69, 71, or 73 or with the pair of primers set forth as SEQ ID NO:9 and 10, SEQ ID NO:11 and 12, SEQ ID NO:13 and 14, SEQ ID NO:21 and 24, SEQ ID NO:22 and 24, SEQ ID NO:21 and 23, SEQ ID NO:25 and 28, SEQ ID NO:26 and 28, or SEQ ID NO:59 and 60. In a preferred embodiment, the plant DNA library is a Nicotiana tabacum (tobacco), *Lycopersicon esculentum* (tomato), *Brassica napus* (oilseed rape), *Arabidopsis thaliana, Beta vulgaris* (sugarbeet), *Helianthus annuus* (sunflower), or *Solanum tuberosum* (potato) DNA library.

BRIEF DESCRIPTION OF THE SEQUENCES IN THE SEQUENCE LISTING

SEQ ID NO:1—Full length cDNA sequence of a NIM1 homologue from *Nicotiana tabacum.*

SEQ ID NO:2—Protein sequence of the Nicotiana tabacum NIM1 homologue encoded by SEQ ID NO:1.

SEQ ID NO:3—Full length cDNA sequence of a NIM1 homologue from *Lycopersicon esculentum.*

SEQ ID NO:4—Protein sequence of the *Lycopersicon esculentum* NIM1 homologue encoded by SEQ ID NO:3.

SEQ ID NO:5—Partial cDNA sequence of a NIM1 homologue from *Brassica napus.*

SEQ ID NO:6—Partial protein sequence of the *Brassica napus* NIM1 homologue encoded by SEQ ID NO:5.

SEQ ID NO:7—Full length cDNA sequence of a NIM1 homologue (AtNMLc5) from *Arabidopsis thaliana.*

SEQ ID NO:8—Full length protein sequence of the *Arabidopsis thaliana* NIM1 homologue AtNMLc5 encoded by SEQ ID NO:7.

SEQ ID NOs:9–14—Oligonucleotide primers used in Examples 1–4.

SEQ ID NO:15—Genomic DNA sequence of a NIM1 homologue (AtNMLc2) from *Arabidopsis thaliana.*

SEQ ID NO:16—Protein sequence of the Arabidopsis thaliana NIM1 homologue AtNMLc2 encoded by SEQ ID NO:15.

SEQ ID NO:17—Genomic DNA sequence of a NIM1 homologue (AtNMLc4–1) from *Arabidopsis thaliana.*

SEQ ID NO:18—Protein sequence of the *Arabidopsis thaliana* NIM1 homologue AtNMLc4–1 encoded by SEQ ID NO:17.

SEQ ID NO:19—Genomic DNA sequence of a NIM1 homologue (AtNMLc4–2) from *Arabidopsis thaliana.*

SEQ ID NO:20—Protein sequence of the *Arabidopsis thaliana* NIM1 homologue AtNMLc4–2 encoded by SEQ ID NO:19.

SEQ ID NO:21—PCR primer NIM 1A.
SEQ ID NO:22—PCR primer NIM 1B.
SEQ ID NO:23—PCR primer NIM 1C.
SEQ ID NO:24—PCR primer NIM 1D.
SEQ ID NO:25—PCR primer NIM 2A.
SEQ ID NO:26—PCR primer NIM 2B.
SEQ ID NO:27—PCR primer NIM 2C.
SEQ ID NO:28—PCR primer NIM 2D.
SEQ ID NO:29—659 bp NIM-like DNA fragment amplified from *Nicotiana tabacum* (Tobacco A), which is a consensus of 36 sequences and has 67% sequence identity to the *Arabidopsis thaliana* NIM1 gene sequence.

SEQ ID NO:30—Protein sequence encoded by SEQ ID NO:29.

SEQ ID NO:31—498 bp NIM-like DNA fragment amplified from *Nicotiana tabacum* (Tobacco B), which is a consensus of 2 sequences and has 62% sequence identity to the Arabidopsis thaliana NIM1 gene sequence.

SEQ ID NO:32—Protein sequence encoded by SEQ ID NO:31.

SEQ ID NO:33—498 bp NIM-like DNA fragment amplified from *Nicotiana tabacum* (Tobacco C), which is a consensus of 3 sequences and has 63% sequence identity to the Arabidopsis thaliana NIM1 gene sequence.

SEQ ID NO:34—Protein sequence encoded by SEQ ID NO:33.

SEQ ID NO:35—399 bp NIM-like DNA fragment amplified from *Nicotiana tabacum* (Tobacco D), which has 59% sequence identity to the *Arabidopsis thaliana* NIM1 gene sequence.

SEQ ID NO:36—Protein sequence encoded by SEQ ID NO:35.

SEQ ID NO:37—498 bp NIM-like DNA fragment amplified from *Lycopersicon esculentum* (Tomato A), which is a consensus of 8 sequences and has 67% sequence identity to the *Arabidopsis thaliana* NIM1 gene sequence.

SEQ ID NO:38—Protein sequence encoded by SEQ ID NO:37.

SEQ ID NO:39—498 bp NIM-like DNA fragment amplified from *Beta vulgaris* (Sugarbeet), which is a consensus of 24 sequences and has 66% sequence identity to the *Arabidopsis thaliana* NIM1 gene sequence.

SEQ ID NO:40—Protein sequence encoded by SEQ ID NO:39.

SEQ ID NO:41—498 bp NIM-like DNA fragment amplified from *Helianthus annuus* (Sunflower A), which is a consensus of 9 sequences and has 61 % sequence identity to the *Arabidopsis thaliana* NIM1 gene sequence.

SEQ ID NO:42—Protein sequence encoded by SEQ ID NO:41.

SEQ ID NO:43—498 bp NIM-like DNA fragment amplified from *Helianthus annuus* (Sunflower B), which is a consensus of 10 sequences and has 59% sequence identity to the *Arabidopsis thaliana* NIM1 gene sequence.

SEQ ID NO:44—Protein sequence encoded by SEQ ID NO:43.

SEQ ID NO:45—653 bp NIM-like DNA fragment amplified from *Solanum tuberosum* (Potato A), which is a consensus of 15 sequences and has 68% sequence identity to the *Arabidopsis thaliana* NIM1 gene sequence.

SEQ ID NO:46—Protein sequence encoded by SEQ ID NO:45.

SEQ ID NO:47—498 bp NIM-like DNA fragment amplified from *Solanum tuberosum* (Potato B), which is a consensus of 3 sequences and has 61% sequence identity to the *Arabidopsis thaliana* NIM1 gene sequence.

SEQ ID NO:48—Protein sequence encoded by SEQ ID NO:47.

SEQ ID NO:49—477 bp NIM-like DNA fragment amplified from *Solanum tuberosum* (Potato C), which is a consensus of 2 sequences and has 62% sequence identity to the *Arabidopsis thaliana* NIM1 gene sequence.

SEQ ID NO:50—Protein sequence encoded by SEQ ID NO:49.

SEQ ID NO:51—501 bp NIM-like DNA fragment amplified from *Brassica napus* (Canola A), which is a consensus of 5 sequences and has 59% sequence identity to the *Arabidopsis thaliana* NIM1 gene sequence.

SEQ ID NO:52—Protein sequence encoded by SEQ ID NO:51.

SEQ ID NO:53—501 bp NIM-like DNA fragment amplified from *Brassica napus* (Canola B), which is a consensus of 5 sequences and has 58% sequence identity to the *Arabidopsis thaliana* NIM1 gene sequence.

SEQ ID NO:54—Protein sequence encoded by SEQ ID NO:53.

SEQ ID NO:55—498 bp NIM-like DNA fragment amplified from *Brassica napus* (Canola C), which has 56% sequence identity to the *Arabidopsis thaliana* NIM1 gene sequence.

SEQ ID NO:56—Protein sequence encoded by SEQ ID NO:55.

SEQ ID NO:57—498 bp NIM-like DNA fragment amplified from *Brassica napus* (Canola D), which has 73% sequence identity to the *Arabidopsis thaliana* NIM1 gene sequence.

SEQ ID NO:58—Protein sequence encoded by SEQ ID NO:57.

SEQ ID NO:59—PCR primer NIM 3A.

SEQ ID NO:60—PCR primer NIM 3B.

SEQ ID NO:61—148 bp NIM-like DNA fragment amplified from *Lycopersicon esculentum* (Tomato B), which is a consensus of 3 sequences and has 72% sequence identity to the *Arabidopsis thaliana* NIM1 gene sequence.

SEQ ID NO:62—Protein sequence encoded by SEQ ID NO:61.

SEQ ID NO:63—Full length cDNA sequence of a NIM1 homologue from *Beta vulgaris* (Sugarbeet), which corresponds to the PCR fragment of SEQ ID NO:39.

SEQ ID NO:64—Protein sequence of the sugarbeet NIM1 homologue encoded by SEQ ID NO:62.

SEQ ID NO:65—Full length cDNA sequence of a NIM1 homologue from *Helianthus annuus* (Sunflower B), which corresponds to the PCR fragment of SEQ ID NO:43.

SEQ ID NO:66—Protein sequence of the *Helianthus annuus* NIM1 homologue encoded by SEQ ID NO:65.

SEQ ID NO:67—cDNA sequence corresponding to the *Arabidopsis thaliana* NIM-like genomic sequence AtNMLc2 (SEQ ID NO:15).

SEQ ID NO:68—Protein sequence encoded by SEQ ID NO:67.

SEQ ID NO:69—cDNA sequence corresponding to the *Arabidopsis thaliana* NIM-like genomic sequence AtNMLc4-1 (SEQ ID NO:17).

SEQ ID NO:70—Protein sequence encoded by SEQ ID NO:69.

SEQ ID NO:71—cDNA sequence corresponding to the *Arabidopsis thaliana* NIM-like genomic sequence AtNMLc4-2 (SEQ ID NO:19).

SEQ ID NO:72—Protein sequence encoded by SEQ ID NO:71.

SEQ ID NO:73—Full length cDNA sequence of a NIM1 homologue from *Nicotiana tabacum* (Tobacco B), which corresponds to the PCR fragment of SEQ ID NO:71.

SEQ ID NO:74—Protein sequence of the *Nicotiana tabacum* NIM1 homologue encoded by SEQ ID NO:73.

Definitions

In describing the present invention, the following terms will be employed, and are intended to be defined as indicated below.

Associated With/Operatively Linked: Refers to two DNA sequences that are related physically or functionally. For example, a promoter or regulatory DNA sequence is said to be "associated with" a DNA sequence that codes for an RNA or a protein if the two sequences are operatively linked, or situated such that the regulator DNA sequence will affect the expression level of the coding or structural DNA sequence.

Chimeric Gene: A recombinant DNA sequence in which a promoter or regulatory DNA sequence is operatively linked to, or associated with, a DNA sequence that codes for an mRNA or which is expressed as a protein, such that the regulator DNA sequence is able to regulate transcription or expression of the associated DNA sequence. The regulator DNA sequence of the chimeric gene is not normally operatively linked to the associated DNA sequence as found in nature.

Coding Sequence: a nucleic acid sequence that is transcribed into RNA such as nRNA, rRNA, tRNA, snRNA, sense RNA or antisense RNA. Preferably the RNA is then translated in an organism to produce a protein.

Complementary: refers to two nucleotide sequences that comprise antiparallel nucleotide sequences capable of pairing with one another upon formation of hydrogen bonds between the complementary base residues in the antiparallel nucleotide sequences.

Expression: refers to the transcription and/or translation of an endogenous gene or a transgene in plants. In the case of antisense constructs, for example, expression may refer to the transcription of the antisense DNA only.

Expression Cassette: A nucleic acid sequence capable of directing expression of a particular nucleotide sequence in an appropriate host cell, comprising a promoter operatively linked to the nucleotide sequence of interest which is operatively linked to termination signals. It also typically comprises sequences required for proper translation of the nucleotide sequence. The expression cassette comprising the nucleotide sequence of interest may be chimeric, meaning that at least one of its components is heterologous with respect to at least one of its other components. The expression cassette may also be one which is naturally occurring but has been obtained in a recombinant form useful for heterologous expression. Typically, however, the expression cassette is heterologous with respect to the host, i.e., the particular nucleic acid sequence of the expression cassette does not occur naturally in the host cell and must have been introduced into the host cell or an ancestor of the host cell by a transformation event. The expression of the nucleotide sequence in the expression cassette may be under the control of a constitutive promoter or of an inducible promoter which initiates transcription only when the host cell is exposed to some particular external stimulus. In the case of a multicellular organism, such as a plant, the promoter can also be specific to a particular tissue, or organ, or stage of development.

Gene: A defined region that is located within a genome and that, besides the aforementioned coding nucleic acid sequence, comprises other, primarily regulatory, nucleic acid sequences responsible for the control of expression, i.e., transcription and translation of the coding portion. A gene may also comprise other 5' and 3' untranslated sequences and termination sequences. Further elements that may be present are, for example, introns.

Heterologous DNA Sequence: The terms "heterologous DNA sequence", "exogenous DNA segment" or "heterologous nucleic acid," as used herein, each refer to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling. The terms also includes non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides.

Homologous DNA Sequence: A DNA sequence naturally associated with a host cell into which it is introduced.

Isocoding: A nucleic acid sequence is isocoding with a reference nucleic acid sequence when the nucleic acid sequence encodes a polypeptide having the same amino acid sequence as the polypeptide encoded by the reference nucleic acid sequence.

Isolated: In the context of the present invention, an isolated nucleic acid molecule or an isolated enzyme is a nucleic acid molecule or enzyme that, by the hand of man, exists apart from its native environment and is therefore not a product of nature. An isolated nucleic acid molecule or enzyme may exist in a purified form or may exist in a non-native environment such as, for example, a recombinant host cell.

Minimal Promoter: a promoter element, particularly a TATA element, that is inactive or has greatly reduced promoter activity in the absence of upstream activation. In the presence of a suitable transcription factor, a minimal promoter functions to permit transcription.

Native: refers to a gene that is present in the genome of an untransformed cell.

Naturally occurring: the term "naturally occurring" is used to describe an object that can be found in nature as distinct from being artificially produced by man. For example, a protein or nucleotide sequence present in an organism (including a virus), which can be isolated from a source in nature and which has not been intentionally modified by man in the laboratory, is naturally occurring.

NIM1 : Gene described in Ryals et al., 1997, which is involved in the SAR signal transduction cascade.

NIM1: Protein encoded by the NIM1 gene

Nucleic acid: the term "nucleic acid" refers to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g. degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19: 5081 (1991); Ohtsuka et al., *J Biol. Chem.* 260: 2605–2608 (1985); Rossolini et al, *Mol. Cell. Probes* 8: 91–98 (1994)). The terms "nucleic acid" or "nucleic acid sequence" may also be used interchangeably with gene, cDNA, and mRNA encoded by a gene. In the context of the present invention, the nucleic acid molecule is preferably a segment of DNA. Nucleotides are indicated by their bases by the following standard abbreviations: adenine (A), cytosine (C), thymine (T), and guanine (G).

ORF: Open Reading Frame.

Plant: Any whole plant.

Plant Cell: Structural and physiological unit of a plant, comprising a protoplast and a cell wall. The plant cell may be in form of an isolated single cell or a cultured cell, or as a part of higher organized unit such as, for example, a plant tissue, a plant organ, or a whole plant.

Plant Cell Culture: Cultures of plant units such as, for example, protoplasts, cell culture cells, cells in plant tissues, pollen, pollen tubes, ovules, embryo sacs, zygotes and embryos at various stages of development.

Plant Material: Refers to leaves, stems, roots, flowers or flower parts, fruits, pollen, egg cells, zygotes, seeds, cuttings, cell or tissue cultures, or any other part or product of a plant.

Plant Organ: A distinct and visibly structured and differentiated part of a plant such as a root, stem, leaf, flower bud, or embryo.

Plant tissue: A group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

Promoter: An untranslated DNA sequence upstream of the coding region that contains the binding site for RNA polymerase II and initiates transcription of the DNA. The promoter region may also include other elements that act as regulators of gene expression.

Protoplast: An isolated plant cell without a cell wall or with only parts of the cell wall.

Purified: the term "purified," when applied to a nucleic acid or protein, denotes that the nucleic acid or protein is essentially free of other cellular components with which it is associated in the natural state. It is preferably in a homogeneous state although it can be in either a dry or aqueous solution. Purity and homogeneity are typically determined using analytical chemistry techniques such as polyacrylamide gel electrophoresis or high performance liquid chromatography. A protein which is the predominant species present in a preparation is substantially purified. The term "purified" denotes that a nucleic acid or protein gives rise to essentially one band in an electrophoretic gel. Particularly, it means that the nucleic acid or protein is at least about 50% pure, more preferably at least about 85% pure, and most preferably at least about 99% pure.

Recombinant DNA molecule: a combination of DNA molecules that are joined together using recombinant DNA technology Regulatory Elements: Sequences involved in controlling the expression of a nucleotide sequence. Regulatory elements comprise a promoter operably linked to the nucleotide sequence of interest and termination signals. They also typically encompass sequences required for proper translation of the nucleotide sequence.

Selectable marker gene: a gene whose expression in a plant cell gives the cell a selective advantage. The selective advantage possessed by the cells transformed with the selectable marker gene may be due to their ability to grow in the presence of a negative selective agent, such as an antibiotic or a herbicide, compared to the growth of non-transformed cells. The selective advantage possessed by the transformed cells, compared to non-transformed cells, may also be due to their enhanced or novel capacity to utilize an added compound as a nutrient, growth factor or energy source. Selectable marker gene also refers to a gene or a combination of genes whose expression in a plant cell gives the cell both, a negative and a positive selective advantage.

Significant Increase: an increase in enzymatic activity that is larger than the margin of error inherent in the measurement technique, preferably an increase by about 2-fold or greater of the activity of the wild-type enzyme in the presence of the inhibitor, more preferably an increase by about 5-fold or greater, and most preferably an increase by about 10-fold or greater.

The terms "identical" or percent "identity" in the context of two or more nucleic acid or protein sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

Substantially identical: the phrase "substantially identical," in the context of two nucleic acid or protein sequences, refers to two or more sequences or subsequences that have at least 60%, preferably 80%, more preferably 90–95%, and most preferably at least 99% nucleotide or amino acid residue identity, when compared and aligned for maximum correspondence, as measured using one of the following sequence comparison algorithms or by visual inspection Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of the coding regions. Furthermore, substantially identical nucleic acid or protein sequences perform substantially the same function.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2: 482 (1981), by the homology alignment algorithm of Needleman & Wunsch, *J Mol. Biol.* 48: 443 (1970), by the search for similarity method of Pearson & Lipman, *Proc. Nat'l. Acad. Sci. USA* 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Ausubel et al., infra).

One example of an algorithm that is suitable for determining percent sequence identity and sequence similarity is the BLAST algorithm, which is described in Altschul et al., *J Mol. Biol.* 215: 403–410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89: 10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90: 5873–5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

Another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. An extensive guide to the hybridization of nucleic acids is found in Tijssen (1993) *Laboratory Techniques in Biochemistry and Molecular Biology-Hybridization with Nucleic Acid Probes* part I chapter 2 "Overview of principles of hybridization and the strategy of nucleic acid probe assays" Elsevier, N.Y. Generally, highly stringent hybridization and wash conditions are selected to be about 5° C. lower than the thermal melting point (Tm) for the specific sequence at a defined ionic strength and pH. Typically, under "stringent conditions" a probe will hybridize to its target subsequence, but to no other sequences.

The $T_m$ is the temperature (under defined ionic strength and pH) at which 50% of the target sequence hybridizes to a perfectly matched probe. Very stringent conditions are selected to be equal to the Tm for a particular probe. An example of stringent hybridization conditions for hybridization of complementary nucleic acids which have more than 100 complementary residues on a filter in a Southern or northern blot is 50% formamide with 1 mg of heparin at 42° C., with the hybridization being carried out overnight. An example of highly stringent wash conditions is 0.15M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4–6×SSC at 40° C. for 15 minutes. For short probes (e.g., about 10 to 50 nucleotides), stringent conditions typically involve salt concentrations of less than about 1.0M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2×(or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

The following are examples of sets of hybridization/wash conditions that may be used to clone homologous nucleotide sequences that are substantially identical to reference nucleotide sequences of the present invention: a reference nucleotide sequence preferably hybridizes to the reference nucleotide sequence in 7% sodium dodecyl sulfate (SDS), 0.5 M $NaPO_4$, 1 mM EDTA at 50° C. with washing in 2×SSC, 0.1% SDS at 50° C, more desirably in 7% sodium dodecyl sulfate (SDS), 0.5 M $NaPO_4$, 1 mM EDTA at 50° C with washing in 0.1×SSC, 0.1% SDS at 50° C., more desirably still in 7% sodium dodecyl sulfate (SDS), 0.5 M $NaPO_4$, 1 mM EDTA at 50° C. with washing in 0.5×SSC, 0.1% SDS at 50° C. preferably in 7% sodium dodecyl sulfate (SDS), 0.5 M $NaPO_4$, 1 mM EDTA at 50° C. with washing in 0.1×SSC, 0.1% SDS at 50° C. more preferably in 7% sodium dodecyl sulfate (SDS), 0.5 M $NaPO_4$, 1 mM EDTA at 50° C. with washing in 0.1×SSC, 0.1% SDS at 65° C.

A further indication that two nucleic acid sequences or proteins are substantially identical is that the protein encoded by the first nucleic acid is immunologically cross reactive with, or specifically binds to, the protein encoded by the second nucleic acid. Thus, a protein is typically substantially identical to a second protein, for example, where the two proteins differ only by conservative substitutions.

The phrase "specifically (or selectively) binds to an antibody," or "specifically (or selectively) immunoreactive with," when referring to a protein or peptide, refers to a binding reaction which is determinative of the presence of the protein in the presence of a heterogeneous population of proteins and other biologics. Thus, under designated immunoassay conditions, the specified antibodies bind to a particular protein and do not bind in a significant amount to other proteins present in the sample. Specific binding to an antibody under such conditions may require an antibody that is selected for its specificity for a particular protein. For example, antibodies raised to the protein with the amino acid sequence encoded by any of the nucleic acid sequences of the invention can be selected to obtain antibodies specifically immunoreactive with that protein and not with other proteins except for polymorphic variants. A variety of immunoassay formats may be used to select antibodies specifically immunoreactive with a particular protein. For example, solid-phase ELISA immunoassays, Western blots, or immunohistochemistry are routinely used to select monoclonal antibodies specifically immunoreactive with a protein. See Harlow and Lane (1988) *Antibodies, A Laboratory Manual*, Cold Spring Harbor Publications, New York "Harlow and Lane"), for a description of immunoassay formats and conditions that can be used to determine specific immunoreactivity. Typically a specific or selective reaction will be at least twice background signal or noise and more typically more than 10 to 100 times background.

"Conservatively modified variations" of a particular nucleic acid sequence refers to those nucleic acid sequences that encode identical or essentially identical amino acid sequences, or where the nucleic acid sequence does not encode an amino acid sequence, to essentially identical sequences. Because of the degeneracy of the genetic code, a large number of functionally identical nucleic acids encode any given polypeptide. For instance the codons CGT, CGC, CGA, CGG, AGA, and AGG all encode the amino acid arginine. Thus, at every position where an arginine is specified by a codon, the codon can be altered to any of the corresponding codons described without altering the encoded protein. Such nucleic acid variations are "silent variations" which are one species of "conservatively modified variations." Every nucleic acid sequence described herein which encodes a protein also describes every possible silent variation, except where otherwise noted. One of skill will recognize that each codon in a nucleic acid (except ATG, which is ordinarily the only codon for methionine) can be modified to yield a functionally identical molecule by standard techniques. Accordingly, each "silent variation" of a nucleic acid which encodes a protein is implicit in each described sequence.

Furthermore, one of skill will recognize that individual substitutions deletions or additions that alter, add or delete a single amino acid or a small percentage of amino acids (typically less than 5%, more typically less than 1%) in an encoded sequence are "conservatively modified variations," where the alterations result in the substitution of an amino acid with a chemically similar amino acid. Conservative substitution tables providing functionally similar amino acids are well known in the art. The following five groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic: Arginine (R), Lysine (K), Histidine (H); Acidic: Aspartic acid (D), Glutamic acid (E), Asparagine (N), Glutamine (Q). See also, Creighton (1984) *Proteins,* W. H. Freeman and Company. In addition, individual substitutions, deletions or additions which alter, add or delete a single amino acid or a small percentage of amino acids in an encoded sequence are also "conservatively modified variations."

A "subsequence" refers to a sequence of nucleic acids or amino acids that comprise a part of a longer sequence of nucleic acids or amino acids (e.g., protein) respectively.

Nucleic acids are "elongated" when additional nucleotides (or other analogous molecules) are incorporated into the nucleic acid. Most commonly, this is performed with a polymerase (e.g., a DNA polymerase), e.g., a polymerase which adds sequences at the 3' terminus of the nucleic acid.

Two nucleic acids are "recombined" when sequences from each of the two nucleic acids are combined in a progeny nucleic acid. Two sequences are "directly" recombined when both of the nucleic acids are substrates for recombination. Two sequences are "indirectly recombined" when the sequences are recombined using an intermediate such as a cross-over oligonucleotide. For indirect recombination, no more than one of the sequences is an actual substrate for recombination, and in some cases, neither sequence is a substrate for recombination.

A "specific binding affinity" between two molecules, for example, a ligand and a receptor, means a preferential binding of one molecule for another in a mixture of molecules. The binding of the molecules can be considered specific if the binding affinity is about $1\times10^4$ $M^{-1}$ to about $1\times10^6$ $M^{-1}$ or greater.

Transformation: a process for introducing heterologous DNA into a host cell or organism.

"Transformed," "transgenic," and "recombinant" refer to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed," "non-transgenic," or "non-recombinant" host refers to a wild-type organism, e.g., a bacterium or plant, which does not contain the heterologous nucleic acid molecule.

Deposits

The following material has been deposited with the Agricultural Research Service, Patent Culture Collection (NRRL), 1815 North University Street, Peoria, Illinois 61604, USA, under the terms of the Budapest Treaty on the International Recognition of the Deposit of Microorganisms for the Purposes of Patent Procedure. All restrictions on the availability of the deposited material will be irrevocably removed upon the granting of a patent.

| Clone | Accession Number | Date of Deposit |
| --- | --- | --- |
| pNOV1203 | NRRL B-30049 | Aug. 17, 1998 |
| pNOV1204 | NRRL B-30050 | Aug. 17, 1998 |
| pNOV1206 | NRRL B-30051 | Aug. 17, 1998 |
| AtNMLc5 | NRRL B-30139 | May 25, 1999 |

DETAILED DESCRIPTION OF THE INVENTION

The present invention concerns homologues of Arabidopsis NIM1 that are isolated from *Nicotiana tabacum* (tobacco), *Lycopersicon esculentum* (tomato), *Brassica napus* (oilseed rape), *Arabidopsis thaliana, Beta vulgaris* (sugarbeet), *Helianthus annuus* (sunflower), and *Solanum tuberosum* (potato) cDNA and genomic DNA libraries by PCR amplification. Northern data on several of the NIM1 homologues described herein indicates constitutive expression or BTH-inducibility. The homologues of the NIM1 gene described herein are predicted to encode proteins involved in the signal transduction cascade responsive to biological and chemical inducers, which leads to systemic acquired resistance in plants. The present invention also concerns the transgenic expression of such NIM1 homologues in plants to increase SAR gene expression and enhance disease resistance.

The DNA sequences of the invention can be isolated using the techniques described in the examples below, or by PCR using the sequences set forth in the sequence listing as the basis for constructing PCR primers. For example, oligonucleotides having the sequence of approximately the first and last 20–25 consecutive nucleotides of SEQ ID NO:7 (e.g., nucleotides 1–20 and 1742–1761 of SEQ ID NO:7) can be used as PCR primers to amplify the cDNA sequence (SEQ ID NO:7) directly from a cDNA library from the source plant (*Arabidopsis thaliana*). The other DNA sequences of the invention can likewise be amplified by PCR from cDNA or genomic DNA libraries of the respective plants using the ends of the DNA sequences set forth in the sequence listing as the basis for PCR primers.

The transgenic expression of the NIM1 homologues of the invention in plants is predicted to result in immunity to a wide array of plant pathogens, which include, but are not limited to viruses or viroids, e.g. tobacco or cucumber mosaic virus, ringspot virus or necrosis virus, pelargonium leaf curl virus, red clover mottle virus, tomato bushy stunt virus, and like viruses; fungi, e.g. oomycetes such as *Phythophthora parasitica* and *Peronospora tabacina;* bacteria, e.g. *Pseudomonas syringae* and *Pseudomonas tabaci;* insects such as aphids, e.g. *Myzus persicae;* and lepidoptera, e.g., *Heliothus* spp.; and nematodes, e.g., *Meloidogyne incognita*. The vectors and methods of the invention are useful against a number of disease organisms of maize including but not limited to downy mildews such as *Scleropthora macrospora, Sclerophthora rayissiae, Sclerospora graminicola, Peronosclerospora sorghi, Peronosclerospora philippinensis, Peronosclerospora sacchari* and *Peronosclerospora maydis;* rusts such as *Puccinia sorphi, Puccinia polysora* and *Physopella zeae;* other fungi such as *Cercospora zeae-maydis, Colletotrichum graminicola, Fusarium monoliforme, Gibberella zeae, Exserohilum turcicum, Kabatiellu zeae, Erysiphe graminis, Septoria* and *Bipolaris maydis;* and bacteria such as *Erwinia stewartii*.

The methods of the present invention can be utilized to confer disease resistance to a wide variety of plants, including gymnosperms, monocots, and dicots. Although disease resistance can be conferred upon any plants falling within these broad classes, it is particularly useful in agronomically important crop plants, such as rice, wheat, barley, rye, rape, corn, potato, carrot, sweet potato, sugar beet, bean, pea, chicory, lettuce, cabbage, cauliflower, broccoli, turnip, radish, spinach, asparagus, onion, garlic, eggplant, pepper, celery, carrot, squash, pumpkin, zucchini, cucumber, apple, pear, quince, melon, plum, cherry, peach, nectarine, apricot, strawberry, grape, raspberry, blackberry, pineapple, avocado, papaya, mango, banana, soybean, tobacco, tomato, sorghum and sugarcane.

A NIM1 homologue coding sequence of the present invention may be inserted into an expression cassette designed for plants to construct a chimeric gene according to the invention using standard genetic engineering techniques. The choice of specific regulatory sequences such as promoter, signal sequence, 5' and 3' untranslated sequences, and enhancer appropriate for the achieving the desired pattern and level of expression in the chosen plant host is within the level of skill of the routineer in the art. The resultant molecule, containing the individual elements linked in proper reading frame, may be inserted into a vector capable of being transformed into a host plant cell.

Examples of promoters capable of functioning in plants or plant cells (i.e., those capable of driving expression of associated coding sequences such as those coding for NIM1 homologues in plant cells) include the Arabidopsis and maize ubiquitin promoters; cauliflower mosaic virus (CaMV) 19S or 35S promoters and CaMV double promoters; rice actin promoters; PR-1 promoters from tobacco, Arabidopsis, or maize; nopaline synthase promoters; small subunit of ribulose bisphosphate carboxylase (ssuRUBISCO) promoters, and the like. Especially preferred is the Arabidopsis ubiquitin promoter. The promoters themselves may be modified to manipulate promoter strength to increase expression of the associated coding sequence in accordance with art-recognized procedures. Preferred promoters for use with the present invention are those that confer high level constitutive expression.

Signal or transit peptides may be fused to the NIM1 homologue coding sequence in the chimeric DNA constructs of the invention to direct transport of the expressed protein to the desired site of action. Examples of signal peptides include those natively linked to the plant pathogenesis-related proteins, e.g. PR-1, PR-2, and the like. See, e.g. Payne et al., 1988. Examples of transit peptides include the chloroplast transit peptides such as those described in Von Heijne et al. (1991), Mazur et al. (1987), and Vorst et al. (1988); and mitochondrial transit peptides such as those described in Boutry et al. (1987). Also included are sequences that result in localization of the encoded protein to various cellular compartments such as the vacuole. See, for example, Neuhaus et al. (1991) and Chrispeels (1991).

The chimeric DNA construct(s) of the invention may contain multiple copies of a promoter or multiple copies of a NIM1 homologue coding sequence of the present invention. In addition, the construct(s) may include coding sequences for markers and coding sequences for other peptides such as signal or transit peptides, each in proper reading frame with the other functional elements in the DNA molecule. The preparation of such constructs are within the ordinary level of skill in the art.

Useful markers include peptides providing herbicide, antibiotic or drug resistance, such as, for example, resistance to protoporphyrinogen oxidase inhibitors, hygromycin, kanamycin, G418, gentamycin, lincomycin, methotrexate, glyphosate, phosphinothricin, or the like. These markers can be used to select cells transformed with the chimeric DNA constructs of the invention from untransformed cells. Other useful markers are peptidic enzymes which can be easily detected by a visible reaction, for example a color reaction, for example luciferase, B-glucuronidase, or β-galactosidase.

Chimeric genes designed for plant expression such as those described herein can be introduced into the plant cell in a number of art-recognized ways. Those skilled in the art will appreciate that the choice of method might depend on the type of plant (i.e. monocot or dicot) and/or organelle (i.e. nucleus, chloroplast, mitochondria) targeted for transformation. Suitable methods of transforming plant cells include microinjection (Crossway et al., 1986), electroporation (Riggs et al., 1986), Agrobacterium mediated transformation (Hinchee et al., 1988; Ishida et al., 1996), direct gene transfer (Paszkowski et al., 1984; Hayashimoto et al, 1990), and ballistic particle acceleration using devices available from Agracetus, Inc., Madison, Wis. and Dupont, Inc., Wilmington, Del. (see, for example, U.S. Pat. No. 4,945, 050; and McCabe et al., 1988). See also, Weissinger et al. (1988); Sanford et al. (1987) (onion); Christou et al. (1988) (soybean); McCabe et al. (1988) (soybean); Datta et al. (1990) (rice); Klein et al. (1988) (maize); Klein et al. (1988) (maize); Klein et al. (1988) (maize); Fromm et al. (1990); and Gordon-Kamm et al. (1990) (maize); Svab et al. (1990) (tobacco chloroplasts); Gordon-Kamm et al. (1993) (maize); Shimamoto et al. (1989) (rice); Christou et al. (1991) (rice); Datta et al. (1990) (rice); European Patent Application EP 0 332 581 (orchardgrass and other Pooideae); Vasil et al. (1993) (wheat); Weeks et al. (1993) (wheat); Wan et al. (1994) (barley); Jahne et al. (1994) (barley); Umbeck et al. (1987) (cotton); Casas et al. (1993) (sorghum); Somers et al. (1992) (oats); Torbert et al. (1995) (oats); Weeks et al., (1993) (wheat); WO 94/13822 (wheat); and Nehra et al. (1994) (wheat). A particularly preferred set of embodiments for the introduction of recombinant DNA molecules into maize by microprojectile bombardment can be found in Koziel et al. (1993); Hill et al. (1995) and Koziel et al. (1996). An additional preferred embodiment is the protoplast transformation method for maize as disclosed in EP 0 292 435.

Once a chimeric gene comprising a NIM1 homologue coding sequence has been transformed into a particular plant species, it may be propagated in that species or moved into other varieties of the same species, particularly including commercial varieties, using traditional breeding techniques. Particularly preferred plants of the invention include the agronomically important crops listed above. The genetic properties engineered into the transgenic seeds and plants described above are passed on by sexual reproduction and can thus be maintained and propagated in progeny plants.

EXAMPLES

The invention is illustrated in further detail by the following detailed procedures, preparations, and examples. The examples are for illustration only, and are not to be construed as limiting the scope of the present invention. Standard recombinant DNA and molecular cloning techniques used here are well known in the art and are described by Sambrook, et al., 1989; by T. J. Silhavy, M. L. Berman, and L. W. Enquist, 1984; and by Ausubel, F. M. et al., 1987.

I. Isolation of Homologues of the Arabidopsis NIM1 Gene

Example 1

Isolation of a NIM1 Homologue From *Nicotiana tabacum*

Plasmid DNA from a mass excision of phage from a tobacco cDNA library is used as a template for PCR using the following primer pairs: 5'-AGATTATTGTCAAGTCTAATG-3' (SEQ ID NO:9)+5'-TTCCATGTACCTTTGCTTC-3' (SEQ ID NO:10), and 5'-GCGGATCCATGGATAATAGTAGG-3' (SEQ ID NO:11)+5'-GCGGATCCTATTTCCTAAAAGGG-3' (SEQ ID NO:12). Cycling conditions are preferably 94 degrees for one minute, 40 degrees for one minute, and 72 degrees for 1.5 minutes, and the reaction is preferably carried out for 40 cycles. PCR products are run out on agarose gels, excised, and cloned into pCRII-TOPO (Invitrogen).

The full-length cDNA sequence of this tobacco NIM1 homologue is shown in SEQ ID NO:1, and the protein encoded by this cDNA sequence is shown in SEQ ID NO:2. A tobacco NIM1 homologue comprising SEQ ID NO:1 has been deposited as pNOV1206 with the NRRL (Agricultural Research Service, Patent Culture Collection, Northern Regional Research Center, 1815 North University Street, Peoria, Ill. 61604, U.S.A) on Aug. 17, 1998, and assigned accession no. NRRL B-3005 1.

Example 2

Isolation of a NIM1 Homologue From *Lycopersicon esculentum*

Phagemids are excised from λ ZAPII cDNA libraries of tomato using a protocol from Stratagene. Phagemids (plasmids) are mass-transformed into *E. coli* XL1-Blue in 10 pools of about 80,000 clones each and DNA is extracted from these pools. The pools are screened by PCR for the presence of NIM1 homologues by PCR using the following primers: 5'-AGATTATTGTCAAGTCTAATG-3' (SEQ ID NO:9) and 5'-TTCCATGTACCTTTGCTTC-3' (SEQ ID NO:10).

Sequences amplified from the pools are confirmed to contain NIM1 homologues by cloning the PCR-amplified DNA fragment and sequencing. Pools are made successively smaller and screened by PCR using the same primers mentioned above for the presence of the NIM1 homologues until a single clone containing the homologue is obtained. In the event that the cDNA clone contains a partial gene, missing the 5' end, 5' RACE (Rapid Amplification of cDNA Ends) is used to obtain the full-length sequence of the gene.

The full-length cDNA sequence of this tomato NIM1 homologue is shown in SEQ ID NO:3, and the protein encoded by this cDNA sequence is shown in SEQ ID NO:4. A tomato NIM1 homologue comprising SEQ ID NO:3 has been deposited as pNOV1204 with the NRRL (Agricultural Research Service, Patent Culture Collection, Northern Regional Research Center, 1815 North University Street, Peoria, Ill. 61604, U.S.A) on Aug. 17, 1998, and assigned accession no. NRRL B-30050.

Example 3

Isolation of a NIM1 Homologue From *Brassica napus*

Phagemids are excised from λ ZAPII cDNA libraries of *Brassica napus* using a protocol from Stratagene. Phagemids (plasmids) are mass-transformed into *E. coli* XL1-Blue in 10 pools of about 80,000 clones each and DNA is extracted from these pools. The pools are screened by PCR for the presence of NIM1 homologues by PCR using the following primers: 5'-AGATTATTGTCAAGTCTAATG-3' (SEQ ID NO:9) and 5'-TTCCATGTACCTTTGCTTC-3' (SEQ ID NO:10).

Sequences amplified from the pools are confirmed to contain NIM1 homologues by cloning the PCR-amplified DNA fragment and sequencing. Pools are made successively smaller and screened by PCR using the same primers mentioned above for the presence of the NIM1 homologues until a single clone containing the homologue is obtained. In the event that the cDNA clone contains a partial gene, missing the 5' end, 5' RACE (Rapid Amplification of cDNA Ends) is used to obtain the full-length sequence of the gene.

A partial cDNA sequence of this *Brassica napus* NIM1 homologue is shown in SEQ ID NO:5, and the protein encoded by this cDNA sequence is shown in SEQ ID NO:6. A *Brassica napus* NIM1 homologue comprising SEQ ID NO:5 has been deposited as pNOV1203 with the NRRL (Agricultural Research Service, Patent Culture Collection, Northern Regional Research Center, 1815 North University Street, Peoria, Ill. 61604, U.S.A) on Aug. 17, 1998, and assigned accession no. NRRL B-30049.

Example 4

Isolation of a NIM1 Homologue From *Arabidopsis thaliana*

BLAST searches using the Arabidopsis or tomato NIM1 amino acid sequences as queries detect GenBank entry B26306, which contains Arabidopsis genomic sequence from the Bacterial Artificial Chromosome (BAC) F18D8. Part of the BAC sequence is predicted to encode a protein with significant similarity (47% amino acid identity) to NIM1. The following primers are designed to regions of the F18D8 sequence: 5'-TCAAGGCCTTGGATTCAGATG-3' (SEQ ID NO:13) and 5'-ATTAACTGCGCTACGTCCGTC-3' (SEQ ID NO:14).

The primers are used in a PCR reaction with DNA from a pFL61 based Arabidopsis cDNA library as a template. Preferable cycling conditions are 94 degrees for 30 seconds, 53 degrees for 30 seconds, 72 degrees for 30 seconds. The reaction is preferably run for 40 cycles. A PCR product of the predicted size (290 base pairs) is detected, and the cDNA clone corresponding to the F18D8 primers is purified from the cDNA library by sequential purification by passage of increasingly smaller amounts of the library through *E. coli* and rediagnosis of the presence of the clone by PCR. Ultimately, a single positive clone is obtained and sequenced. The sequence of the clone confirms the presence of an open reading frame with significant homology to NIM1.

A full-length cDNA sequence of this *Arabidopsis thaliana* NIM1 homologue is shown in SEQ ID NO:7, and the protein encoded by this cDNA sequence is shown in SEQ ID NO:8. An *Arabidopsis thaliana* NIM1 homologue comprising SEQ ID NO:7 has been deposited as AtNMLc5 in *E. coli* with the NRRL (Agricultural Research Service, Patent Culture Collection, Northern Regional Research Center, 1815 North University Street, Peoria, Ill. 61604, U.S.A) on May 25, 1999, and assigned accession no. NRRL B-30139.

Example 5

Design of Degenerate Primers

In addition to the NIM1 gene (Ryals et al., 1997) and the NIM-like gene described above in Example 4 (AtNMLc5—SEQ ID NO:7), *Arabidopsis thaliana* contains three other NIM-like (NML) genomic sequences: AtNMLc2 (SEQ ID NO:15), AtNMLc4–1 (SEQ ID NO:17), and AtNMLc4–2 (SEQ ID NO:19), where c[#] stands for the chromosome number on which the particular NML gene is located. Using the GCG Seqweb multiple sequence alignment program (Pretty, Wisconsin Genetics Computer Group), the NIM1 sequences from *Arabidopsis thaliana* (Ryals et al., 1997), *Nicotiana tabacum* (Example 1—SEQ ID NO:1), and *Lycopersicon esculentum* (Example 2—SEQ ID NO:3), as well as the NML sequences From *Arabidopsis thaliana* (SEQ ID NO:7, 15, 17, and 19) are aligned. Based on this alignment, three regions emerge with sufficient conservation to design degenerate PCR primers for PCR amplification of NIM1 homologues from other crop species, including sugarbeet, sunflower, potato, and canola. The primers designed from these conserved regions are listed below in Table 1. The NIM 1 (A—D) primers are designed using a lineup with only the NIM1 genes From *Arabidopsis thaliana* (Ryals et al., 1997), *Nicotiana tabacum* (Example 1—SEQ ID NO:1), and *Lycopersicon esculentum* (Example 2—SEQ ID NO:3). The NIM 2(A—D) primers are designed using a lineup with these three sequences in addition to the four NML sequences From *Arabidopsis thaliana* (SEQ ID NO:7, 15, 17, and 19). Primers are preferably synthesized by Genosys Biotechnologies, Inc. (The Woodlands, Tex.). Positions of degeneracy are indicated in Table 1 by the notation of more than one base at a single site in the oligonucleotide. "Orientation" designates whether the primer is directed towards the 3' end (Downstream) or the 5' end (Upstream) of the cDNA.

TABLE 2

Primer combinations and DNA fragment sizes

| Left Primer | Right Primer | Fragment Size (bp) |
|---|---|---|
| NIM 1A | NIM 1D | 669 |
| NIM 1A | NIM 1C | 195 |
| NIM 1B | NIM 1D | 499 |
| NIM 2A | NIM 2D | 676 |
| NIM 2A | NIM 2C | 200 |
| NIM 2B | NIM 2D | 503 |

Degenerate primer PCR is preferably performed with Ready-To-Go PCR Beads (Amersham, Piscataway, N.J.) in a GeneAmp PCR System 9700 (PE Applied Biosystems, Foster City, Calif.). 20 to 40 ng of genomic DNA or 5 to 10 ng of cDNA is used in each reaction, with each primer at a final concentration of 0.8 $\mu$M. Preferable cycling parameters are as follows: 94° C. for 1 minute; 3 cycles of [94° C. for 30 seconds; 37° C. for 30 seconds; 72° C. for 2 minutes]; 35 cycles of [94° C. for 30 seconds; 60° C. for 30 seconds; 72°

TABLE 1

Degenerate Primers

```
Primer Sequence (5' to 3')              SEQ ID NO:    Orientation

NIM 1A GAGATTATTGTCAAGTCTAATGTAGATA      SEQ ID NO:21  Downstream
              T                T
NIM 1B ACTGGACTCGGATGATATTGAATTA         SEQ ID NO:22  Downstream
          T T T T     G   G
NIM 1C TAACTCAACATCATCAGAATCAAATGC       SEQ ID NO:23  Upstream
          T     T     C G C G
NIM 1D GTTGAGCAAGAGCAACTCTATTTTCAAG      SEQ ID NO:24  Upstream
             T  C  CC
                    G
                    T
NIM 2A TGCATAGAAATAATTGTGAAGTCTAATGTAGA  SEQ ID NO:25  Downstream
             T G  TG   C      G   T
NIM 2B GGCACTGGACTCAGATGATGTTGAACT       SEQ ID NO:26  Downstream
          T    T T            GT
NIM 2C AACTCAACATCATCAGAATCCAATGCC       SEQ ID NO:27  Upstream
         GT           T G   G
NIM 2D AGTTGAGCAAGGCCAACTCGATTTTCAAAAT   SEQ ID NO:28  Upstream
            T  C  A       T        GG
                  T
```

Example 6

PCR Amplification of NIM-like DNA Fragments From Crop Species

NIM-like DNA fragments are amplified from Arabidopsis, tomato, tobacco, sugarbeet, sunflower, potato, and canola, using either genomic DNA or cDNA as templates. The primer combinations used, along with the expected fragment sizes, are listed below in Table 2.

C. for 2 minutes]; 72° C. for 7 minutes; 4° C. hold. Reaction products are analyzed on 2% agarose gels and DNA fragments of the appropriate size are excised. DNA fragments are isolated from agarose bands using, for example, the Geneclean III Kit (BIO 101, Inc., Carlsbad, Calif.) and cloned using, for example, the TOPO TA Cloning Kit (Invitrogen Corporation, Carlsbad, Calif.). Plasmids are isolated using, for example, the CONCERT Rapid Plasmid Miniprep System (Life Technologies, Inc., Rockville, Md.) and sequenced by standard protocols.

NIM-like DNA fragments are obtained from all plant species attempted, and in many cases multiple, unique NIM-like sequences are isolated. Table 3 details the NIM-like fragments that are isolated.

TABLE 3

NIM-like PCR fragments

| Species | Successful Primer Pairs | PCR Template | Unique Clones | SEQ ID NO: |
|---|---|---|---|---|
| Arabidopsis | 1A/1D; 1B/1D | Genomic DNA | One | |
| Tobacco | 1A/1D; 1B/1D; 2A/2D; 2B/2D | cDNA | Four | SEQ ID NO: 29, 31, 33, and 35 |
| Tomato | 1A/1D; 1B/1D; 2A/2D; 2B/2D | Genomic DNA, cDNA | One | SEQ ID NO: 37 |
| Sugarbeet | 1B/1D; 2B/2D | Genomic DNA, cDNA | One | SEQ ID NO: 39 |
| Sunflower | 2B/2D | cDNA | Two | SEQ ID NO: 41 and 43 |
| Potato | 1A/1D; 1A/1C; 1B/1D; 2A/2D; 2B/2D | cDNA | Three | SEQ ID NO: 45, 47, and 49 |
| Canola | 2B/2D | cDNA | Four | SEQ ID NO: 51, 53, 55, and 57 |

Based on these results, the degenerate primer PCR described above can amplify NIM-like fragments from a wide variety of plant species. In particular, the primer combination of NIM 2B/NIM 2D is successful with cDNA as a template from all species attempted. The use of Ready-To-Go PCR Beads is especially preferably for obtaining products. In addition, using cDNA as a template is preferable for all samples except Arabidopsis, tomato and sugarbeet, where genomic DNA is sufficient.

Example 7

Additional Degenerate Primers

A new pair of degenerate primers is designed based on a sequence alignment of the four tobacco fragments (SEQ ID NO:29, 31, 33, and 35) and the tomato sequence (SEQ ID NO:37) for use in determining whether tomato also contains similar NIM-like sequences that are not amplified with the degenerate primers listed in Table 1. The primers designed from these fragments are listed below in Table 3 and are preferably synthesized by Genosys Biotechnologies, Inc. (The Woodlands, Texas). Positions of degeneracy are indicated in Table 3 by the notation of more than one base at a single site in the oligonucleotide. "Orientation" designates whether the primer is directed towards the 3' end (Downstream) or the 5' end (Upstream) of the cDNA.

TABLE 4

Additional degenerate primers

```
Primer Sequence (5' TO 3')                SEQ ID NO:    Orientation

NIM 3A TAGATGAAGCATACGCTCTCCACTATGCTGT    SEQ ID NO:59  Downstream
           T C T         T T
NIM 3B GGCTCCTTACGCATGGCAGCAACATGAAGGAC   SEQ ID NO:60  Upstream
          T C T              TG     C
```

Degenerate primer PCR is performed as described above using tomato cDNA, and potential products are cloned and sequenced. The sequence analysis reveals two classes of NIM-like fragments: the first is identical to the tomato sequence shown in SEQ ID NO:37, and the second is unique in tomato and 88% identical to the tobacco sequences shown in SEQ ID NO:31 and 33. The sequence of this new tomato sequence is presented in SEQ ID NO:61.

Example 8

Full-length NIM-like cDNA's

Corresponding cDNA sequences upstream and downstream from NIM-like PCR fragments are preferably obtained by RACE PCR using the SMART RACE cDNA Amplification Kit (Clontech, Palo Alto, Calif.). Preferably, at least three independent RACE products are sequenced for each 5'- or 3'-end in order to eliminate PCR errors. Resulting full-length cDNA sequences for Sugarbeet, Sunflower B, and Tobacco B NIM1 homologues, which correspond to the NIM-like PCR fragments shown in SEQ ID NO:39, 43, and 31 are presented as SEQ ID NO:63, 65, and 73 respectively.

NIM-like *Arabidopsis thaliana* cDNA's corresponding to the NIM-like genomic sequences AtNMLc2 (SEQ ID NO:15), AtNMLc4–1 (SEQ ID NO:17), and AtNMLc4–2 (SEQ ID NO:19), are preferably cloned by RT-PCR. Total RNA From *Arabidopsis thaliana* is reverse transcribed using oligo dT primer. The resulting first strand cDNA is amplified by PCR using specific sense and antisense oligonucleotide primers designed based on the 5' and 3' ends of the coding region of each genomic sequence (SEQ ID NO:15, 17, and 19). PCR fragments of the predicted sizes are cloned into a vector and sequenced to confirm that these cDNA clones correspond to the NIM-like genomic sequences. A cDNA sequence corresponding to the NIM-like genomic sequence AtNMLc2 (SEQ ID NO:15) is presented as SEQ ID NO:67; a full-length cDNA sequence corresponding to the NIM-like genomic sequence AtNMLc4–1 (SEQ ID NO:17) is presented as SEQ ID NO:69; and a full-length cDNA sequence corresponding to the NIM-like genomic sequence AtNMLc4–2 (SEQ ID NO:19) is presented as SEQ ID NO:71.

Example 9

Northern Analysis

Northern data shows that expression of the sugarbeet NIM-like clone (SEQ ID NO:39 and 63) increases three to seven fold after 100 $\mu$M or 300 $\mu$M BTH (benzo(1, 2, 3)thiadiazole-7-carbothioic acid S-methyl ester) treatment. Also, Northern data shows that expression of the Sunflower A NIM-like clone (SEQ ID NO:41) is constitutive. Furthermore, Northern data shows that expression of the Sunflower B NIM-like clone (SEQ ID NO:43 and 65) increases two fold after 100 $\mu$M or 300 $\mu$M BTH treatment.

II. Expression of the Gene Sequences of the Invention in Plants

A NIM1 homologue of the present invention can be incorporated into plant cells using conventional recombinant DNA technology. Generally, this involves inserting a coding sequence of the invention into an expression system to which the coding sequence is heterologous (i.e., not normally present) using standard cloning procedures known in the art. The vector contains the necessary elements for the transcription and translation of the inserted protein-coding sequences. A large number of vector systems known in the art can be used, such as plasmids, bacteriophage viruses and other modified viruses. Suitable vectors include, but are not limited to, viral vectors such as lambda vector systems λgt1 1, λgt10 and Charon 4; plasmid vectors such as pBI121, pBR322, pACYC177, pACYC184, pAR series, pKK223-3, pUC8, pUC9, pUC18, pUC19, pLG339, pRK290, pKC37, pKC101, pCDNAII; and other similar systems. The components of the expression system may also be modified to increase expression. For example, truncated sequences, nucleotide substitutions or other modifications may be employed. The expression systems described herein can be used to transform virtually any crop plant cell under suitable conditions. Transformed cells can be regenerated into whole plants such that the NIM1 homologue increases SAR gene expression and enhances disease resistance in the transgenic plants.

Example 10

Construction of Plant Expression Cassettes

Coding sequences intended for expression in transgenic plants are first assembled in expression cassettes behind a suitable promoter expressible in plants. The expression cassettes may also comprise any further sequences required or selected for the expression of the transgene. Such sequences include, but are not restricted to, transcription terminators, extraneous sequences to enhance expression such as introns, vital sequences, and sequences intended for the targeting of the gene product to specific organelles and cell compartments. These expression cassettes can then be easily transferred to the plant transformation vectors described below. The following is a description of various components of typical expression cassettes.
1. Promoters The selection of the promoter used in expression cassettes will determine the spatial and temporal expression pattern of the transgene in the transgenic plant. Selected promoters will express transgenes in specific cell types (such as leaf epidermal cells, mesophyll cells, root cortex cells) or in specific tissues or organs (roots, leaves or flowers, for example) and the selection will reflect the desired location of accumulation of the gene product. Alternatively, the selected promoter may drive expression of the gene under various inducing conditions. Promoters vary in their strength, i.e., ability to promote transcription. Depending upon the host cell system utilized, any one of a number of suitable promoters can be used, including the gene's native promoter. The following are non-limiting examples of promoters that may be used in expression cassettes.
a. Constitutive Expression, the Ubiquitin Promoter:

Ubiquitin is a gene product known to accumulate in many cell types and its promoter has been cloned from several species for use in transgenic plants (e.g. sunflower—Binet et al., 1991; maize—Christensen et al., 1989; and Arabidopsis—Norris et al., 1993). The maize ubiquitin promoter has been developed in transgenic monocot systems and its sequence and vectors constructed for monocot transformation are disclosed in the patent publication EP 0 342 926 (to Lubrizol). Taylor et al. (1993) describe a vector (pAHC25) that comprises the maize ubiquitin promoter and first intron and its high activity in cell suspensions of numerous monocotyledons when introduced via microprojectile bombardment. The Arabidopsis ubiquitin promoter is especially preferred for use with the NIM1 homologues of the present invention. The ubiquitin promoter is suitable for gene expression in transgenic plants, both monocotyledons and dicotyledons. Suitable vectors are derivatives of pAHC25 or any of the transformation vectors described in this application, modified by the introduction of the appropriate ubiquitin promoter and/or intron sequences.
b. Constitutive Expression, the CaMV 35S Promoter:

Construction of the plasmid pCGN1761 is described in the published patent application EP 0 392 225 (Example 23). pCGN1761 contains the "double" CaMV 35S promoter and the tml transcriptional terminator with a unique EcoRI site between the promoter and the terminator and has a pUC-type backbone. A derivative of pCGN1761 is constructed which has a modified polylinker which includes NotI and XhoI sites in addition to the existing EcoRI site. This derivative is designated pCGN1761ENX. pCGN1761ENX is useful for the cloning of cDNA sequences or coding sequences (including microbial ORF sequences) within its polylinker for the purpose of their expression under the control of the 35S promoter in transgenic plants. The entire 35S promoter-coding sequence-tml terminator cassette of such a construction can be excised by HindIII, SphI, SalI, and AbaI sites 5' to the promoter and XbaI, BamHI and BglI sites 3' to the terminator for transfer to transformation vectors such as those described below. Furthermore, the double 35S promoter fragment can be removed by 5' excision with HindIII, SphI, SalI, XbaI, or PstI, and 3' excision with any of the polylinker restriction sites (EcoRI, NotI or XhoI ) for replacement with another promoter. If desired, modifications around the cloning sites can be made by the introduction of sequences that may enhance translation. This is particularly useful when overexpression is desired. For example, pCGN1761ENX may be modified by optimization of the translational initiation site as described in Example 37 of U.S. Pat. No. 5,639,949.
c. Constitutive Expression, the Actin Promoter:

Several isoforms of actin are known to be expressed in most cell types and consequently the actin promoter is a good choice for a constitutive promoter. In particular, the promoter from the rice ActI gene has been cloned and characterized (McElroy et al., 1990). A 1.3 kb fragment of the promoter was found to contain all the regulatory elements required for expression in rice protoplasts. Furthermore, numerous expression vectors based on the ActI promoter have been constructed specifically for use in monocotyledons (McElroy et al., 1991). These incorporate the ActI-intron 1, AdhI 5' flanking sequence and AdhI-intron 1 (from the maize alcohol dehydrogenase gene) and sequence from the CaMV 35S promoter. Vectors showing highest expression were fusions of 35S and ActI intron or the ActI 5' flanking sequence and the ActI intron. Optimization of sequences around the initiating ATG (of the GUS reporter gene) also enhanced expression. The promoter expression cassettes described by McElroy et al. (1991) can be easily modified for gene expression and are particularly suitable for use in monocotyledonous hosts. For example, promoter-containing fragments is removed from the McElroy constructions and used to replace the double 35S promoter in pCGN1761ENX, which is then available for the insertion of specific gene sequences. The fusion genes thus constructed can then be transferred to appropriate transformation vectors. In a separate report, the rice ActI promoter with its first intron has also been found to direct high expression in cultured barley cells (Chibbar et al., 1993).

d. Inducible Expression, the PR-1 Promoter:

The double 35S promoter in pCGN1761ENX may be replaced with any other promoter of choice that will result in suitably high expression levels. By way of example, one of the chemically regulatable promoters described in U.S. Pat. No. 5,614,395 may replace the double 35S promoter. The promoter of choice is preferably excised from its source by restriction enzymes, but can alternatively be PCR-amplified using primers that carry appropriate terminal restriction sites. Should PCR-amplification be undertaken, then the promoter should be re-sequenced to check for amplification errors after the cloning of the amplified promoter in the target vector. The chemically/pathogen regulatable tobacco PR-1a promoter is cleaved from plasmid pCIB1004 (for construction, see example 21 of EP 0 332 104) and transferred to plasmid pCGN1761ENX (Uknes et al., 1992). pCIB1004 is cleaved with NcoI and the resultant 3' overhang of the linearized fragment is rendered blunt by treatment with T4 DNA polymerase. The fragment is then cleaved with HindIII and the resultant PR-1a promoter-containing fragment is gel purified and cloned into pCGN1761ENX from which the double 35S promoter has been removed. This is done by cleavage with AhoI and blunting with T4 polymerase, followed by cleavage with HindIII and isolation of the larger vector-terminator containing fragment into which the pCIB1004 promoter fragment is cloned. This generates a pCGN1761ENX derivative with the PR-1a promoter and the tml terminator and an intervening polylinker with unique EcoRI and NotI sites. The selected coding sequence can be inserted into this vector, and the fusion products (i.e. promoter-gene-terminator) can subsequently be transferred to any selected transformation vector, including those described infra. Various chemical regulators may be employed to induce expression of the selected coding sequence in the plants transformed according to the present invention, including the benzothiadiazole, isonicotinic acid, and salicylic acid compounds disclosed in U.S. Pat. Nos. 5,523,311 and 5, 614, 395.

e. Inducible Expression, an Ethanol-Inducible Promoter:

A promoter inducible by certain alcohols or ketones, such as ethanol, may also be used to confer inducible expression of a coding sequence of the present invention. Such a promoter is for example the alcA gene promoter from *Aspergillus nidulans* (Caddick et al., 1998). *A. nidulans,* the alcA gene encodes alcohol dehydrogenase I, the expression of which is regulated by the AlcR transcription factors in presence of the chemical inducer. For the purposes of the present invention, the CAT coding sequences in plasmid palcA:CAT comprising a alcA gene promoter sequence fused to a minimal 35S promoter (Caddick et al., 1998) are replaced by a coding sequence of the present invention to form an expression cassette having the coding sequence under the control of the alcA gene promoter. This is carried out using methods well known in the art.

f. Inducible Expression, a Glucocorticoid-Inducible Promoter:

Induction of expression of a NIM1 homologue of the present invention using systems based on steroid hormones is also contemplated. For example, a glucocorticoid-mediated induction system is used (Aoyama and Chua, 1997) and gene expression is induced by application of a glucocorticoid, for example a synthetic glucocorticoid, preferably dexamethasone, preferably at a concentration ranging from 0.1 mM to 1 mM, more preferably from 10 mM to 100 mM. For the purposes of the present invention, the luciferase gene sequences are replaced by a gene sequence encoding a NIM1 homologue to form an expression cassette having the gene sequence encoding a NIM1 homologue under the control of six copies of the GAL4 upstream activating sequences fused to the 35S minimal promoter. This is carried out using methods well known in the art. The trans-acting factor comprises the GAL4 DNA-binding domain (Keegan et al., 1986) fused to the transactivating domain of the herpes viral protein VP16 (Triezenberg et al., 1988) fused to the hormone-binding domain of the rat glucocorticoid receptor (Picard et al., 1988). The expression of the fusion protein is controlled by any promoter suitable for expression in plants known in the art or described here. This expression cassette is also comprised in the plant comprising the gene sequence encoding a NIM1 homologue fused to the 6xGAL4/minimal promoter. Thus, tissue- or organ-specificity of the fusion protein is achieved leading to inducible tissue- or organ-specificity of the NIM1 homologue.

g. Root Specific Expression:

Another pattern of gene expression is root expression. A suitable root promoter is described by de Framond (1991) and also in the published patent application EP 0 452 269. This promoter is transferred to a suitable vector such as pCGN1 761ENX for the insertion of a selected gene and subsequent transfer of the entire promoter-gene-terminator cassette to a transformation vector of interest.

h. Wound-Inducible Promoters:

Wound-inducible promoters may also be suitable for gene expression. Numerous such promoters have been described (e.g. Xu et al., 1993); Logemann et al., 1989; Rohrmeier & Lehle, 1993; Firek et al., 1993; Warner et al., 1993) and all are suitable for use with the instant invention. Logemann et al. describe the 5' upstream sequences of the dicotyledonous potato wunI gene. Xu et al. show that a wound-inducible promoter from the dicotyledon potato (pin2) is active in the monocotyledon rice. Further, Rohrmeier & Lehle describe the cloning of the maize WipI cDNA which is wound induced and which can be used to isolate the cognate promoter using standard techniques. Similar, Firek et al. and Warner et al. have described a wound-induced gene from the monocotyledon *Asparagus officinalis,* which is expressed at local wound and pathogen invasion sites. Using cloning techniques well known in the art, these promoters can be transferred to suitable vectors, fused to the genes pertaining to this invention, and used to express these genes at the sites of plant wounding.

i. Pith-Preferred Expression:

Patent Application WO 93/07278 describes the isolation of the maize trpa gene, which is preferentially expressed in pith cells. The gene sequence and promoter extending up to −1726 bp from the start of transcription are presented. Using standard molecular biological techniques, this promoter, or parts thereof, can be transferred to a vector such as pCGN1761 where it can replace the 35S promoter and be used to drive the expression of a foreign gene in a pith-preferred manner. In fact, fragments containing the pith-preferred promoter or parts thereof can be transferred to any vector and modified for utility in transgenic plants.

j. Leaf-Specific Expression:

A maize gene encoding phosphoenol carboxylase (PEPC) has been described by Hudspeth & Grula (1989). Using standard molecular biological techniques the promoter for this gene can be used to drive the expression of any gene in a leaf-specific manner in transgenic plants.

k. Pollen-Specific Expression:

WO 93/07278 describes the isolation of the maize calcium-dependent protein kinase (CDPK) gene which is expressed in pollen cells. The gene sequence and promoter extend up to 1400 bp from the start of transcription. Using standard molecular biological techniques, this promoter or parts thereof, can be transferred to a vector such as pCGN1761 where it can replace the 35S promoter and be used to drive the expression of a NIM1 homologue of the present invention in a pollen-specific manner.

2. Transcriptional Terminators

A variety of transcriptional terminators are available for use in expression cassettes. These are responsible for the termination of transcription beyond the transgene and its correct polyadenylation. Appropriate transcriptional terminators are those that are known to function in plants and include the CaMV 35S terminator, the tml terminator, the nopaline synthase terminator and the pea rbcS E9 terminator. These can be used in both monocotyledons and dicotyledons. In addition, a gene's native transcription terminator may be used.

3. Sequences for the Enhancement or Regulation of Expression

Numerous sequences have been found to enhance gene expression from within the transcriptional unit and these sequences can be used in conjunction with the genes of this invention to increase their expression in transgenic plants.

Various intron sequences have been shown to enhance expression, particularly in monocotyledonous cells. For example, the introns of the maize AdhI gene have been found to significantly enhance the expression of the wild-type gene under its cognate promoter when introduced into maize cells. Intron 1 was found to be particularly effective and enhanced expression in fusion constructs with the chloramphenicol acetyltransferase gene (Callis et al., 1987). In the same experimental system, the intron from the maize bronzel gene had a similar effect in enhancing expression. Intron sequences have been routinely incorporated into plant transformation vectors, typically within the non-translated leader.

A number of non-translated leader sequences derived from viruses are also known to enhance expression, and these are particularly effective in dicotyledonous cells. Specifically, leader sequences from Tobacco Mosaic Virus (TMV, the "W-sequence"), Maize Chlorotic Mottle Virus (MCMV), and Alfalfa Mosaic Virus (AMV) have been shown to be effective in enhancing expression (e.g. Gallie et al, 1987; Skuzeski et al., 1990).

4. Targeting of the Gene Product Within the Cell

Various mechanisms for targeting gene products are known to exist in plants and the sequences controlling the functioning of these mechanisms have been characterized in some detail. For example, the targeting of gene products to the chloroplast is controlled by a signal sequence found at the amino terminal end of various proteins which is cleaved during chloroplast import to yield the mature protein (e.g. Comai et al., 1988). These signal sequences can be fused to heterologous gene products to effect the import of heterologous products into the chloroplast (van den Broeck, et al., 1985). DNA encoding for appropriate signal sequences can be isolated from the 5' end of the cDNAs encoding the RUBISCO protein, the CAB protein, the EPSP synthase enzyme, the GS2 protein and many other proteins which are known to be chloroplast localized. See also, the section entitled "Expression With Chloroplast Targeting" in Example 37 of U.S. Pat. No. 5,639,949.

Other gene products are localized to other organelles such as the mitochondrion and the peroxisome (e.g. Unger et al., 1989). The cDNAs encoding these products can also be manipulated to effect the targeting of heterologous gene products to these organelles. Examples of such sequences are the nuclear-encoded ATPases and specific aspartate amino transferase isoforms for mitochondria. Targeting cellular protein bodies has been described by Rogers et al. (1985).

In addition, sequences have been characterized which cause the targeting of gene products to other cell compartments. Amino terminal sequences are responsible for targeting to the ER, the apoplast, and extracellular secretion from aleurone cells (Koehler & Ho, 1990).

Additionally, amino terminal sequences in conjunction with carboxy terminal sequences are responsible for vacuolar targeting of gene products (Shinshi et al., 1990).

By the fusion of the appropriate targeting sequences described above to transgene sequences of interest it is possible to direct the transgene product to any organelle or cell compartment. For chloroplast targeting, for example, the chloroplast signal sequence from the RUBISCO gene, the CAB gene, the EPSP synthase gene, or the GS2 gene is fused in frame to the amino terminal ATG of the transgene. The signal sequence selected should include the known cleavage site, and the fusion constructed should take into account any amino acids after the cleavage site which are required for cleavage. In some cases this requirement may be fulfilled by the addition of a small number of amino acids between the cleavage site and the transgene ATG or, alternatively, replacement of some amino acids within the transgene sequence. Fusions constructed for chloroplast import can be tested for efficacy of chloroplast uptake by in vitro translation of in vitro transcribed constructions followed by in vitro chloroplast uptake using techniques described by Bartlett et al. (1982) and Wasmann et al. (1986). These construction techniques are well known in the art and are equally applicable to mitochondria and peroxisomes.

The above-described mechanisms for cellular targeting can be utilized not only in conjunction with their cognate promoters, but also in conjunction with heterologous promoters so as to effect a specific cell-targeting goal under the transcriptional regulation of a promoter that has an expression pattern different to that of the promoter from which the targeting signal derives.

Example 11

Construction of Plant Transformation Vectors

Numerous transformation vectors available for plant transformation are known to those of ordinary skill in the plant transformation arts, and the genes pertinent to this invention can be used in conjunction with any such vectors. The selection of vector will depend upon the preferred transformation technique and the target species for transformation. For certain target species, different antibiotic or herbicide selection markers may be preferred. Selection markers used routinely in transformation include the nptII gene, which confers resistance to kanamycin and related antibiotics (Messing & Vierra, 1982; Bevan et al., 1983), the bar gene, which confers resistance to the herbicide phosphinothricin (White et al., 1990; Spencer et al., 1990), the hph gene, which confers resistance to the antibiotic hygromycin (Blochinger & Diggelmann), and the dhfr gene, which confers resistance to methatrexate (Bourouis et al, 1983), and the EPSPS gene, which confers resistance to glyphosate (U.S. Patent Nos. 4,940,935 and 5,188,642).

1. Vectors Suitable for Agrobacterium Transformation

Many vectors are available for transformation using *Agrobacterium tumefaciens*. These typically carry at least one T-DNA border sequence and include vectors such as pBIN19

(Bevan, Nucl. Acids Res. (1984)) and pXYZ. Below, the construction of two typical vectors suitable for Agrobacterium transformation is described.

a. pCIB200 and pCIB2001:

The binary vectors pcIB200 and pCIB2001 are used for the construction of recombinant vectors for use with Agrobacterium and are constructed in the following manner. pTJS75kan is created by Nar digestion of pTJS75 (Schmidhauser & Helinski, 1985) allowing excision of the tetracycline-resistance gene, followed by insertion of an AccI fragment from pUC4K carrying an NPTII (Messing & Vierra, 1982; Bevan et al., 1983; McBride et al., 1990). AhoI linkers are ligated to the EcoR V fragment of PCIB7 which contains the left and right T-DNA borders, a plant selectable nos/nptII chimeric gene and the pUC polylinker (Rothstein et al., 1987), and the AhoI-digested fragment are cloned into SalI-digested pTJS75kan to create pCIB200 (see also EP 0 332 104, example 19). pCIB200 contains the following unique polylinker restriction sites: EcoRI, SstI, KpnI, BglII, xbaI, and SalI. pCIB2001 is a derivative of pCIB200 created by the insertion into the polylinker of additional restriction sites. Unique restriction sites in the polylinker of pCIB2001 are EcoRI, SstI, KpnI, BglII, xbaI, SalI, MluI, BclI, AvrII, ApaI, HpaI, and StuI. pCIB2001, in addition to containing these unique restriction sites also has plant and bacterial kanamycin selection, left and right T-DNA borders for Agrobacterium-mediated transformation, the RK2-derived trfA function for mobilization between *E. coli* and other hosts, and the OriT and OriV functions also from RK2. The pCIB2001 polylinker is suitable for the cloning of plant expression cassettes containing their own regulatory signals.

b. pCIB10 and Hygromycin Selection Derivatives thereof:

The binary vector pCIB10 contains a gene encoding kanamycin resistance for selection in plants and T-DNA right and left border sequences and incorporates sequences from the wide host-range plasmid pRK252 allowing it to replicate in both *E. coli* and Agrobacterium. Its construction is described by Rothstein et al. (1987). Various derivatives of pCIB10 are constructed which incorporate the gene for hygromycin B phosphotransferase described by Gritz et al., 1983). These derivatives enable selection of transgenic plant cells on hygromycin only (pCIB743), or hygromycin and kanamycin (pCIB715, pCIB717).

2. Vectors Suitable for non-Agrobacterium Transformation

Transformation without the use of Agrobacterium tumefaciens circumvents the requirement for T-DNA sequences in the chosen transformation vector and consequently vectors lacking these sequences can be utilized in addition to vectors such as the ones described above which contain T-DNA sequences. Transformation techniques that do not rely on Agrobacterium include transformation via particle bombardment, protoplast uptake (e.g. PEG and electroporation) and microinjection. The choice of vector depends largely on the preferred selection for the species being transformed. Below, the construction of typical vectors suitable for non-Agrobacterium transformation is described.

a. pCIB3064:

pCIB3064 is a pUC-derived vector suitable for direct gene transfer techniques in combination with selection by the herbicide basta (or phosphinothricin). The plasmid pCIB246 comprises the CaMV 35S promoter in operational fusion to the *E. coli* GUS gene and the CaMV 35S transcriptional terminator and is described in the PCT published application WO 93/07278. The 35S promoter of this vector contains two ATG sequences 5' of the start site. These sites are mutated using standard PCR techniques in such a way as to remove the ATGs and generate the restriction sites SspI and PvuII The new restriction sites are 96 and 37 bp away from the unique SalI site and 101 and 42 bp away from the actual start site. The resultant derivative of pCIB246 is designated pCIB3025. The GUS gene is then excised from pCIB3025 by digestion with SalI and SacI, the termini rendered blunt and religated to generate plasmid pCIB3060. The plasmid pJIT82 is obtained from the John Innes Centre, Norwich and the a 400 bp SmaI fragment containing the bar gene from *Streptomyces viridochromogenes* is excised and inserted into the HpaI site of pCIB3060 (Thompson et al., 1987). This generated pCIB3064, which comprises the bar gene under the control of the CaMV 35S promoter and terminator for herbicide selection, a gene for ampicillin resistance (for selection in *E. coli*) and a polylinker with the unique sites SphI, PstI, HindIII, and BamHI This vector is suitable for the cloning of plant expression cassettes containing their own regulatory signals.

b. pSOG19 and pSOG35:

pSOG35 is a transformation vector that utilizes the *E. coli* gene dihydrofolate reductase (DFR) as a selectable marker conferring resistance to methotrexate. PCR is used to amplify the 35S promoter (−800 bp), intron 6 from the maize Adhl gene (—550 bp) and 18 bp of the GUS untranslated leader sequence from pSOG10. A 250-bp fragment encoding the *E. coli* dihydrofolate reductase type II gene is also amplified by PCR and these two PCR fragments are assembled with a SacI-PstI fragment from pB1221 (Clontech) which comprises the pUC19 vector backbone and the nopaline synthase terminator. Assembly of these fragments generates pSOG19 which contains the 35S promoter in fusion with the intron 6 sequence, the GUS leader, the DHFR gene and the nopaline synthase terminator. Replacement of the GUS leader in pSOG19 with the leader sequence from Maize Chlorotic Mottle Virus (MCMV) generates the vector pSOG35. pSOG19 and pSOG35 carry the pUC gene for ampicillin resistance and have HindIII, SphI, PstI and EcoRI sites available for the cloning of foreign substances.

Example 12

Transformation

Once the gene sequence of interest has been cloned into an expression system, it is transformed into a plant cell. Methods for transformation and regeneration of plants are well known in the art. For example, Ti plasmid vectors have been utilized for the delivery of foreign DNA, as well as direct DNA uptake, liposomes, electroporation, microinjection, and microprojectiles. In addition, bacteria from the genus Agrobacterium can be utilized to transform plant cells. Below are descriptions of representative techniques for transforming both dicotyledonous and monocotyledonous plants.

1. Transformation of Dicotyledons

Transformation techniques for dicotyledons are well known in the art and include Agrobacterium-based techniques and techniques that do not require Agrobacterium. Non-Agrobacterium techniques involve the uptake of exogenous genetic material directly by protoplasts or cells. This can be accomplished by PEG or electroporation mediated uptake, particle bombardment-mediated delivery, or microinjection. Examples of these techniques are described by Paszkowski et al., 1984; Potrykus et al., 1985; Reich et al., 1986; and Klein et al., 1987. In each case the transformed cells are regenerated to whole plants using standard techniques known in the art.

Agrobacterium-mediated transformation is a preferred technique for transformation of dicotyledons because of its high efficiency of transformation and its broad utility with many different species. Agrobacterium transformation typically involves the transfer of the binary vector carrying the foreign DNA of interest (e.g. pCIB200 or pCIB2001) to an appropriate Agrobacterium strain which may depend of the complement of vir genes carried by the host Agrobacterium strain either on a co-resident Ti plasmid or chromosomally (e.g. strain CIB542 for pCIB200 and pCIB2001 (Uknes et al., 1993). The transfer of the recombinant binary vector to Agrobacterium is accomplished by a triparental mating procedure using E. coli carrying the recombinant binary vector, a helper E. coli strain which carries a plasmid such as pRK2013 and which is able to mobilize the recombinant binary vector to the target Agrobacterium strain. Alternatively, the recombinant binary vector can be transferred to Agrobacterium by DNA transformation (Höfgen & Willmitzer, 1988).

Transformation of the target plant species by recombinant Agrobacterium usually involves co-cultivation of the Agrobacterium with explants from the plant and follows protocols well known in the art. Transformed tissue is regenerated on selectable medium carrying the antibiotic or herbicide resistance marker present between the binary plasmid T-DNA borders.

Another approach to transforming plant cells with a gene involves propelling inert or biologically active particles at plant tissues and cells. This technique is disclosed in U.S. Pat. Nos. 4,945,050, 5,036,006, and 5,100,792. Generally, this procedure involves propelling inert or biologically active particles at the cells under conditions effective to penetrate the outer surface of the cell and afford incorporation within the interior thereof When inert particles are utilized, the vector can be introduced into the cell by coating the particles with the vector containing the desired gene. Alternatively, the target cell can be surrounded by the vector so that the vector is carried into the cell by the wake of the particle. Biologically active particles (e.g., dried yeast cells, dried bacterium or a bacteriophage, each containing DNA sought to be introduced) can also be propelled into plant cell tissue.

2. Transformation of Monocotyledons

Transformation of most monocotyledon species has now also become routine. Preferred techniques include direct gene transfer into protoplasts using PEG or electroporation techniques, and particle bombardment into callus tissue. Transformations can be undertaken with a single DNA species or multiple DNA species (i.e. co-transformation) and both these techniques are suitable for use with this invention. Co-transformation may have the advantage of avoiding complete vector construction and of generating transgenic plants with unlinked loci for the gene of interest and the selectable marker, enabling the removal of the selectable marker in subsequent generations, should this be regarded desirable. However, a disadvantage of the use of co-transformation is the less than 100% frequency with which separate DNA species are integrated into the genome (Schocher et al., 1986).

Patent Applications EP 0 292 435, EP 0 392 225, and WO 93/07278 describe techniques for the preparation of callus and protoplasts from an elite inbred line of maize, transformation of protoplasts using PEG or electroporation, and the regeneration of maize plants from transformed protoplasts. Gordon-Kamm et al. (1990) and Fromm et al. (1990) have published techniques for transformation of Al 88-derived maize line using particle bombardment. Furthermore, WO 93/07278 and Koziel et al. (1993) describe techniques for the transformation of elite inbred lines of maize by particle bombardment. This technique utilizes immature maize embryos of 1.5–2.5 mm length excised from a maize ear 14–15 days after pollination and a PDS-1000He Biolistics device for bombardment.

Transformation of rice can also be undertaken by direct gene transfer techniques utilizing protoplasts or particle bombardment. Protoplast-mediated transformation has been described for Japonica-types and Indica-types (Zhang et al., 1988; Shimamoto et al., 1989; Datta et al., 1990). Both types are also routinely transformable using particle bombardment (Christou et al., 1991). Furthermore, WO 93/21335 describes techniques for the transformation of rice via electroporation.

Patent Application EP 0 332 581 describes techniques for the generation, transformation and regeneration of Pooideae protoplasts. These techniques allow the transformation of Dactylis and wheat. Furthermore, wheat transformation has been described by Vasil et al. (1992) using particle bombardment into cells of type C long-term regenerable callus, and also by Vasil et al. (1993) and Weeks et al. (1993) using particle bombardment of immature embryos and immature embryo-derived callus. A preferred technique for wheat transformation, however, involves the transformation of wheat by particle bombardment of immature embryos and includes either a high sucrose or a high maltose step prior to gene delivery. Prior to bombardment, any number of embryos (0.75–1 mm in length) are plated onto MS medium with 3% sucrose (Murashiga & Skoog, 1962) and 3 mg/l 2, 4-D for induction of somatic embryos, which is allowed to proceed in the dark. On the chosen day of bombardment, embryos are removed from the induction medium and placed onto the osmoticum (i.e. induction medium with sucrose or maltose added at the desired concentration, typically 15%). The embryos are allowed to plasmolyze for 2–3 h and are then bombarded. Twenty embryos per target plate is typical, although not critical. An appropriate gene-carrying plasmid (such as pCIB3064 or pSG35) is precipitated onto micrometer size gold particles using standard procedures. Each plate of embryos is shot with the Dupont Biolistics® helium device using a burst pressure of ~1000 psi using a standard 80 mesh screen. After bombardment, the embryos are placed back into the dark to recover for about 24 h (still on osmoticum). After 24 hrs, the embryos are removed from the osmoticum and placed back onto induction medium where they stay for about a month before regeneration. Approximately one month later the embryo explants with developing embryogenic callus are transferred to regeneration medium (MS+1 mg/liter NAA, 5 mg/liter GA), further containing the appropriate selection agent (10 mg/l basta in the case of pCIB3064 and 2 mg/l methotrexate in the case of pSOG35). After approximately one month, developed shoots are transferred to larger sterile containers known as "GA7s" which contain half-strength MS, 2% sucrose, and the same concentration of selection agent.

Tranformation of monocotyledons using Agrobacterium has also been described. See, WO 94/00977 and U.S. Pat. No. 5,591,616.

III. Breeding and Seed Production

Example 13

Breeding

The plants obtained via tranformation with a gene of the present invention can be any of a wide variety of plant species, including those of monocots and dicots; however, the plants used in the method of the invention are preferably selected from the list of agronomically important target crops set forth supra. The expression of a gene of the present invention in combination with other characteristics important for production and quality can be incorporated into plant lines through breeding. Breeding approaches and techniques are known in the art. See, for example, Welsh J. R. (1981); Wood D. R. (Ed.) (1983); Mayo O. (1987); Singh, D. P. (1986); and Wricke and Weber (1986).

The genetic properties engineered into the transgenic seeds and plants described above are passed on by sexual reproduction or vegetative growth and can thus be maintained and propagated in progeny plants. Generally said maintenance and propagation make use of known agricultural methods developed to fit specific purposes such as tilling, sowing or harvesting. Specialized processes such as hydroponics or greenhouse technologies can also be applied. As the growing crop is vulnerable to attack and damages caused by insects or infections as well as to competition by weed plants, measures are undertaken to control weeds, plant diseases, insects, nematodes, and other adverse conditions to improve yield. These include mechanical measures such a tillage of the soil or removal of weeds and infected plants, as well as the application of agrochemicals such as herbicides, fungicides, gametocides, nematicides, growth regulants, ripening agents and insecticides.

Use of the advantageous genetic properties of the transgenic plants and seeds according to the invention can further be made in plant breeding, which aims at the development of plants with improved properties such as tolerance of pests, herbicides, or stress, improved nutritional value, increased yield, or improved structure causing less loss from lodging or shattering. The various breeding steps are characterized by well-defined human intervention such as selecting the lines to be crossed, directing pollination of the parental lines, or selecting appropriate progeny plants. Depending on the desired properties, different breeding measures are taken. The relevant techniques are well known in the art and include but are not limited to hybridization, inbreeding, backcross breeding, multiline breeding, variety blend, interspecific hybridization, aneuploid techniques, etc. Hybridization techniques also include the sterilization of plants to yield male or female sterile plants by mechanical, chemical, or biochemical means. Cross pollination of a male sterile plant with pollen of a different line assures that the genome of the male sterile but female fertile plant will uniformly obtain properties of both parental lines. Thus, the transgenic seeds and plants according to the invention can be used for the breeding of improved plant lines, that for example, increase the effectiveness of conventional methods such as herbicide or pestidice treatment or allow one to dispense with said methods due to their modified genetic properties. Alternatively new crops with improved stress tolerance can be obtained, which, due to their optimized genetic "equipment", yield harvested product of better quality than products that were not able to tolerate comparable adverse developmental conditions.

Example 14

Seed Production

In seeds production, germination quality and uniformity of seeds are essential product characteristics, whereas germination quality and uniformity of seeds harvested and sold by the farmer is not important. As it is difficult to keep a crop free from other crop and weed seeds, to control seedborne diseases, and to produce seed with good germination, fairly extensive and well-defined seed production practices have been developed by seed producers, who are experienced in the art of growing, conditioning and marketing of pure seed. Thus, it is common practice for the farmer to buy certified seed meeting specific quality standards instead of using seed harvested from his own crop. Propagation material to be used as seeds is customarily treated with a protectant coating comprising herbicides, insecticides, fungicides, bactericides, nematicides, molluscicides, or mixtures thereof. Customarily used protectant coatings comprise compounds such as captan, carboxin, thiram (TMTD®), methalaxyl (Apron®), and pirimiphos-methyl (Actellic®). If desired, these compounds are formulated together with further carriers, surfactants or application-promoting adjuvants customarily employed in the art of formulation to provide protection against damage caused by bacterial, fungal or animal pests. The protectant coatings may be applied by impregnating propagation material with a liquid formulation or by coating with a combined wet or dry formulation. Other methods of application are also possible such as treatment directed at the buds or the fruit.

It is a further aspect of the present invention to provide new agricultural methods, such as the methods exemplified above, which are characterized by the use of transgenic plants, transgenic plant material, or transgenic seed according to the present invention.

The seeds may be provided in a bag, container or vessel comprised of a suitable packaging material, the bag or container capable of being closed to contain seeds. The bag, container or vessel may be designed for either short term or long term storage, or both, of the seed. Examples of a suitable packaging material include paper, such as kraft paper, rigid or pliable plastic or other polymeric material, glass or metal. Desirably the bag, container, or vessel is comprised of a plurality of layers of packaging materials, of the same or differing type. In one embodiment the bag, container or vessel is provided so as to exclude or limit water and moisture from contacting the seed. In one example, the bag, container or vessel is sealed, for example heat sealed, to prevent water or moisture from entering. In another embodiment water absorbent materials are placed between or adjacent to packaging material layers. In yet another embodiment the bag, container or vessel, or packaging material of which it is comprised is treated to limit, suppress or prevent disease, contamination or other adverse affects of storage or transport of the seed. An example of such treatment is sterilization, for example by chemical means or by exposure to radiation. Comprised by the present invention is a commercial bag comprising seed of a transgenic plant comprising a gene of the present invention that is expressed in said transformed plant at higher levels than in a wild type plant, together with a suitable carrier, together with label instructions for the use thereof for conferring broad spectrum disease resistance to plants.

IV. Disease Resistance Evaluation

Disease resistance evaluation is performed by methods known in the art. See, Uknes et al. (1993); Görlach et al. (1996); Alexander et al. (1993). For example, several representative disease resistance assays are described below.

Example 15

*Phytophthora parasitica* (Black Shank) Resistance Assay

Assays for resistance to *Phytophthora parasitica*, the causative organism of black shank, are performed on sixweek-old plants grown as described in Alexander et al. (1993). Plants are watered, allowed to drain well, and then inoculated by applying 10 ml of a sporangium suspension (300 sporangia/ml) to the soil. Inoculated plants are kept in a greenhouse maintained at 23–25° C. day temperature, and 20–22° C. night temperature. The wilt index used for the assay is as follows: 0=no symptoms; 1=no symptoms; 1=some sign of wilting, with reduced turgidity; 2=clear wilting symptoms, but no rotting or stunting; 3=clear wilting symptoms with stunting, but no apparent stem rot; 4=severe wilting, with visible stem rot and some damage to root system; 5=as for 4, but plants near death or dead, and with severe reduction of root system. All assays are scored blind on plants arrayed in a random design.

Example 16

Pseudomonas syringae Resistance Assay

Pseudomonas syringae pv. tabaci strain #551 is injected into the two lower leaves of several 6–7-week-old plants at a concentration of $10^6$ or $3 \times 10^6$ per ml in $H_2O$. Six individual plants are evaluated at each time point. Pseudomonas tabaci infected plants are rated on a 5 point disease severity scale, 5=100% dead tissue, 0=no symptoms. A T-test (LSD) is conducted on the evaluations for each day and the groupings are indicated after the Mean disease rating value. Values followed by the same letter on that day of evaluation are not statistically significantly different.

Example 17

Cercospora nicotianae Resistance Assay

A spore suspension of Cercospora nicotianae (ATCC #18366) (100, 000–150, 000 spores per ml) is sprayed to imminent run-off onto the surface of the leaves. The plants are maintained in 100% humidity for five days. Thereafter the plants are misted with water 5–10 times per day. Six individual plants are evaluated at each time point. Cercospora nicotianae is rated on a % leaf area showing disease symptoms basis. A T-test (LSD) is conducted on the evaluations for each day and the groupings are indicated after the Mean disease rating value. Values followed by the same letter on that day of evaluation are not statistically significantly different.

Example 18

Peronospora parasitica Resistance Assay

Assays for resistance to Peronospora parasitica are performed on plants as described in Uknes et al, (1993). Plants are inoculated with a compatible isolate of P. parasitica by spraying with a conidial suspension (approximately $5 \times 10^4$ spores per milliliter). Inoculated plants are incubated under humid conditions at 17° C. in a growth chamber with a 14-hr day/10-hr night cycle. Plants are examined at 3–14 days, preferably 7–12 days, after inoculation for the presence of conidiophores. In addition, several plants from each treatment are randomly selected and stained with lactophenol-trypan blue (Keogh et al., 1980) for microscopic examination.

The above disclosed embodiments are illustrative. This disclosure of the invention will place one skilled in the art in possession of many variations of the invention. All such obvious and foreseeable variations are intended to be encompassed by the claims.

Reference

The references cited herein are indicative of the current state of the art. Each of the following is incorporated by reference into the instant disclosure.

U.S. Pat. No. 4,940,935
U.S. Pat. No. 4,945,050
U.S. Pat. No. 5,036,006
U.S. Pat. No. 5,100,792
U.S. Pat. No. 5,188,642
U.S. Pat. No. 5,523,311
U.S. Pat. No. 5,591,616
U.S. Pat. No. 5,614,395
U.S. Pat. No. 5,639,949
U.S. Pat. No. 5,792,904
EP 0 292 435
EP0 332 104
EP 0 332 581
EP 0 342 926
EP 0 392 225
EP 0 452 269
International PCT Application WO 93/07278
International PCT Application WO 93/21335
International PCT Application WO 94/00977
International PCT Application WO 94/13822
International PCT Application WO 94/16077
International PCT Application WO 97/49822
International PCT Application WO 98/06748
International PCT Application WO 98/26082
International PCT Application WO 98/29537
Alexander et al., Proc. Natl. Acad. Sci. USA 90: 7327–7331 (1993)
Aoyama and Chua, The Plant Journal 11: 605–612 (1997)
Ausubel, F. M. et al., Current Protocols in Molecular Biology, pub. by Greene Publishing Assoc. and Wiley-Interscience (1987)
Bartlett et al., In: Edelmann et al (Eds.) Methods in Chloroplast Molecular Biology, Elsevier pp 1081–1091 (1982)
Bevan et al., Nature 304:184–187 (1983)
Bevan, Nucl. Acids Res. (1984)
Bi et al., Plant J 8: 235–245 (1995)
Binet et al.
Plant Science 79: 87–94 (1991)
Blochinger & Diggelmann, Mol Cell. Biol. 4: 2929–2931
Bourouis et al., EMBO J 2(7): 1099–1104 (1983)
Boutry et al., Nature 328:340–342 (1987)
Caddick et al., Nat Biotechnol 16:177–180 (1998)
Callis et al., Genes Develop. 1:1183–1200 (1987)
Cameron et al., Plant J 5: 715–725 (1994)
Cao et al., Plant Cell 6, 1583–1592 (1994)
Cao et al., Cell 88: 57–63 (1997)
Casas et al., Proc. Natl. Acad. Sci. USA 90: 11212–11216 (1993)
Century et al., Proc. Natl. Acad. Sci. USA 92: 6597–6601 (1995)
Chibbar et al., Plant Cell Rep. 12: 506–509 (1993)
Chrispeels, Ann. Rev. Plant Physiol. Plant Mol. Biol. 42: 21–53 (1991)
Christou et al., Plant Physiol. 87:671–674 (1988)
Christou et al., Biotechnology 9: 957–962 (1991)
Christensen et al., Plant Molec. Biol. 12: 619–632 (1989)
Comai et al., J Biol. Chem. 263: 15104–15109 (1988)
Crossway et al., BioTechniques 4:320–334 (1986)
Datta et al., Biotechnology 8: 736–740 (1990)
de Framond, FEBS 290: 103–106 (1991)
Delaney et al., Science 266: 1247–1250 (1994)
Delaney et al., Proc. Natl. Acad. Sci. USA 92: 6602–6606 (1995)
Dempsey and Klessig, Bulletin de L'Institut Pasteur 93: 167–186 (1995)
Dietrich et al., Cell 77: 565–577 (1994)
Firek et al., Plant Molec. Biol. 22: 129–142 (1993)

Fromm et al., *Biotechnology* 8: 833–839 (1990)
Gaffney et al., *Science* 261: 754–756 (1993)
Gallie et al., *Nucl. Acids Res.* 15: 8693–8711 (1987)
Glazebrook et al., *Genetics* 143: 973–982 (1996)
Gordon-Kamm et al., *Plant Cell* 2: 603–618 (1990)
Gordon-Kamm et al, in "Transgenic Plants", vol. 2., pp.21–33, pub. by Academic Press (1993)
Gorlach et al., *Plant Cell* 8:629–643 (1996)
Greenberg et al., *Cell* 77: 551–563 (1994)
Gritz et al., *Gene* 25: 179–188 (1983)
Hayashimoto et al., *Plant Physiol.* 93: 857–863 (1990)
Hill et al., *Euphytica* 85:119–123 (1995)
Hinchee et al., *Biotechnology* 6:915–921(1988)
Höfgen & Willmitzer, *Nuc. Acids Res.* 16: 9877 (1988)
Hudspeth & Grula, *Plant Molec. Biol* 12: 579–589 (1989)
Hunt and Ryals, *Crit. Rev. in Plant Sci.* 15: 583–606 (1996)
Innis et al., *PCR Protocols, a Guide to Methods and Applications* eds., Academic Press (1 990)
Ishida et al., *Nature Biotechnology* 14: 745–750 (1996)
Jahne et al., *Theor. Appl. Genet.* 89: 525–533 (1994)
Keegan et al., *Science* 231: 699–704 (1986)
Keogh et al., *Trans. Br. Mycol. Soc.* 74: 329–333 (1980)
Klein et al., *Nature* 327: 70–73 (1987)
Klein et al., *Proc. Natl. Acad. Sci. USA* 85:4305–4309 (1988)
Klein et al., *Bio/Technology* 6:559–563 (1988)
Klein et al., *Plant Physiol.* 91:440–444 (1988)
Koziel et al., *Biotechnology* /1: 194–200 (1993)
Koziel et al., *Annals of the New York Academy of Sciences* 792:164–171 (1996)
Lawton et al., "The molecular biology of systemic aquired resistance" in *Mechanisms of Defence Responses in Plants*, B. Fritig and M. Legrand, eds (Dordrecht, The Netherlands: Kluwer Academic Publishers), pp. 422–432 (1993)
Lawton et al., *Plant J* 10:71–82(1996)
Logemann et al., *Plant Cell* 1:151–158 (1989)
Maher et al., *Proc. Natl. Acad. Sci. USA* 91: 7802–7806 (1994)
Mauch-Mani and Slusarenko, *Mol. Plant-Microbe Interact.* 7: 378–383 (1994)
Mauch-Mani and Slusarenko, *Plant Cell* 8: 203–212 (1996)
Mayo O., *The Theory of Plant Breeding*, Second Edition, Clarendon Press, Oxford (1987)
Mazur et al., *Plant Physiol* 85: 1110 (1987)
McBride et al., *Plant Molecular Biology* 14: 266–276 (1990)
McCabe et al., *Biotechnology* 6:923–926 (1988)
McElroy et al., *Plant Cell* 2: 163–171 (1990)
McElroy et al., *Mol. Gen. Genet.* 231: 150–160 (1991)
Messing & Vierra, *Gene* 19: 259–268 (1982)
Murashiga & Skoog, *Physiologia Plantarum* 15: 473–497 (1962)
Nehra et al., *The Plant Journal* 5: 285–297 (1994)
Neuhaus et al., *Proc. Natl. Acad. Sci. USA* 88: 10362–10366 (1991)
Norris et al., *Plant Mol. Biol.* 21: 895–906 (1993)
Pallas et al., *Plant J* 10: 281–293 (1996)
Parker et al., *Plant Cell* 8: 2033–2046 (1996)
Paszkowski et al., *EMBO J.* 3: 2717–2722 (1984)
Payne et al., *Plant Mol. Biol.* 11:89–94 (1988)
Picard et al., *Cell* 54: 1073–1080 (1988)
Potrykus et al., *Mol. Gen. Genet.* 199: 169–177 (1985)
Reich et al., *Biotechnology* 4: 1001–1004 (1986)
Riggs et al, *Proc. Natl. Acad. Sci. USA* 83:5602–5606 (1986)
Rogers et al., *Proc. Natl. Acad. Sci. USA* 82: 6512–6516 (1985)
Rohrmeier & Lehle, *Plant Molec. Biol.* 22: 783–792 (1993)
Rothstein et al., *Gene* 53: 153–161 (1987)
Ryals et al., *Plant Cell* 8: 1809–1819 (1996)
Ryals et al., *Plant Cell* 9: 425–439 (1997)
Sambrook et al., *Molecular Cloning*, eds., Cold Spring Harbor Laboratory Press (1989) Sanford et al., *Particulate Science and Technology* 5:27–37 (1987)
Schmidhauser & Helinski, *J Bacteriol.* 164: 446–455 (1985)
Schocher et al., *Biotechnology* 4: 1093–1096 (1986)
Shimamoto et al., *Nature* 338: 274–277 (1989)
Shinshi et al., *Plant Molec. Biol.* 14: 357–368 (1990)
Shulaev et al., Plant Cell 7: 1691–1701 (1995)
Silhavy, et al., *Experiments with Gene Fusions*, eds., Cold Spring Harbor Laboratory Press (1984)
Singh, D. P., *Breeding for Resistance to Diseases and Insect Pests*, Springer-Verlag, NY (1986)
Skuzeski et al., *Plant Molec. Biol.* 15: 65–79 (1990)
Somers et al., *Bio/Technology* 10: 1589–1594 (1992)
Spencer et al., *Theor. Appl. Genet.* 79: 625–631 (1990)
Stanford et al., *Mol. Gen. Genet.* 215: 200–208 (1989)
Svab et al., *Proc. Natl. Acad. Sci. USA* 87:8526–8530 (1990)
Taylor et al., *Plant Cell Rep.* 12: 491–495 (1993)
Thompson et al. *EMBO J* 6: 2519–2523 (1987)
Torbert et al., *Plant Cell Reports* 14: 635–640 (1995)
Triezenberg et al., *Genes Devel.* 2: 718–729 (1988)
Uknes et al., *Plant Cell* 4: 645–656 (1992)
Uknes et al *Plant Cell* 5: 159–169 (1993)
Uknes et al., *Molecular Plant Microbe Interactions* 6: 680–685 (1993)
Uknes et al., *Mol. Plant-Microbe Interact.* 6: 6 92–698 (1993)
Umbeck et al., *Bio/Technology* 5: 263–266 (1987)
Unger et al., *Plant Molec. Biol.* 13: 411–418 (1989)
van den Broeck, et al., *Nature* 313: 358–363 (1985)
Vasil et al., *Biotechnology* 10: 667–674 (1992)
Vasil et al., *Biotechnology* 11: 1553–1558 (1993)
Vemooij et al., *Plant Cell* 6: 959–965 (1994)
Vernooij et al., *Mol. Plant-Microbe Interact.* 8: 228–234 (1995)
Von Heijne et al., *Plant Mol. Biol. Rep.* 9:104–126 (1991)
Vorst et al., *Gene* 65: 59 (1988)
Wan et al., *Plant Physiol* 104: 37–48 (1994)
Ward et al., *Plant Cell* 3: 1085–1094 (1991)
Warner et al, *Plant J* 3: 191–201 (1993)
Wasmann et al., *Mol. Gen. Genet.* 205: 446–453 (1986)
Weeks et al, *Plant Physiol* 102: 1077–1084 (1993)
Weissinger et al., *Annual Rev. Genet.* 22:421–477 (1988)
Welsh J. R., *Fundamentals of Plant Genetics and Breeding*, John Wiley & Sons, NY (1981)
Weymann et al., *Plant Cell* 7: 2013–2022 (1995)
White et al., *Nucl. Acids Res.* 18: 1062 (1990)
Wood D. R. (Ed.) *Crop Breeding*, American Society of Agronomy Madison, Wis. (1983)
Wricke and Weber, *Quantitative Genetics and Selection Plant Breeding*, Walter de Gruyter and Co., Berlin (1986)
Xu et al., *Plant Molec. Biol.* 22: 573–588 (1993)
Zhang et al., *Plant Cell Rep.* 7: 379–384 (1988)

What is claimed is:

1. An isolated nucleic acid molecule comprising:
   (a) a nucleotide sequence that encodes SEQ ID NO:4 or SEQ ID NO:38; or
   (b) SEQ ID NO: 3 or SEQ ID NO: 37.

2. An isolated nucleic acid molecule according to claim 1, comprising a nucleotide sequence that encodes SEQ ID NO:4 or 38.

3. An isolated mucleic acid molecule according to claim 1, comprising SEQ ID NO:3 or 37.

4. A chimeric gene comprising a promoter active in plants operatively linked to the nucleic acid molecule of claim 1.

5. A recombinant vector comprising the chimeric gene of claim 4.

6. A host cell comprising the chimeric gene of claim 4.

7. A plant comprising the chimeric gene of claim 4.

8. The plant of claim 6, which is selected from the following: rice, wheat, barley, rye, corn, potato, canola, sunflower, carrot, sweet potato, sugarbeet, bean, pea, chicory, lettuce, cabbage, cauliflower, broccoli, turnip, radish, spinach, asparagus, onion, garlic, eggplant, pepper, celery, squash, pumpkin, cucumber, apple, pear, quince, melon, plum, cherry, peach, nectarine, apricot, strawberry, grape, raspberry, blackberry, pineapple, avocado, papaya, mango, banana, soybean, tobacco, tomato, sorghum and sugarcane.

9. A seed from the plant of claim 7.

10. A PCR primer selected from the group consisting of SEQ ID NO:9–10, 21–22, 24–26, 28 59 and 60.

* * * * *